(12) United States Patent
Tornøe et al.

(10) Patent No.: US 7,601,870 B2
(45) Date of Patent: Oct. 13, 2009

(54) SUBSTITUTED ANILINE DERIVATIVES

(75) Inventors: Christian Wenzel Tornøe, København (DK); Mario Rottländer, Greve (DK); Daniel Rodriguez Greve, Stenløse (DK); Nikolay Khanzhin, Humlebaek (DK); Andreas Ritzén, Vanløse (DK); William Patrick Watson, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 340 days.

(21) Appl. No.: 11/312,664

(22) Filed: Dec. 20, 2005

(65) Prior Publication Data

US 2006/0155121 A1 Jul. 13, 2006

Related U.S. Application Data

(63) Continuation of application No. PCT/DK2005/000560, filed on Sep. 2, 2005.

(60) Provisional application No. 60/609,856, filed on Sep. 13, 2004.

(30) Foreign Application Priority Data

Sep. 13, 2004 (DK) .............................. 2004 01394

(51) Int. Cl.
*C07C 233/05* (2006.01)
*A61K 31/65* (2006.01)

(52) U.S. Cl. ............................ 564/219; 564/48; 564/57; 564/188; 564/189; 564/190; 564/220; 564/221; 514/596; 514/626

(58) Field of Classification Search ................ 564/219, 564/220, 221, 48, 57, 188, 189, 190; 514/596, 514/626
See application file for complete search history.

(56) References Cited

U.S. PATENT DOCUMENTS

| 6,762,320 B2 * | 7/2004 | Jolidon et al. ............... 564/157 |
| 2005/0072962 A1 | 4/2005 | Takaku | |

FOREIGN PATENT DOCUMENTS

| EP | 0285219 A | 10/1988 |
| EP | 0554543 A | 8/1993 |
| JP | 41006578 A | 3/1963 |
| JP | 52014745 A | 2/1977 |
| WO | WO 00/21959 A | 4/2000 |
| WO | WO 01/10380 A | 2/2001 |
| WO | WO 2004/080950 A | 9/2004 |
| WO | 2005/087754 A | 9/2005 |

OTHER PUBLICATIONS

Foye et al, Journal of Pharmaceutical Sciences, 1982, 71(6), 680-686.*
Adams, Harry, et al. (2004) Chembiochem 5(5):657-665.
Dahlbom, R., et al. (1957) Acta Chemica Scandinavica 11(8):1350-1354.
Main, M.J., et al. (Aug. 2000) Molecular Pharmacology 58(2):253-262.
Mukai, Toshihiko, et al. (1977) STN Database Accn. No. 1977:452961.
Ohnmacht, et al. (1996) J Med Chem 39(23):4592-4601.
Okuzu, Masahito, et al. (1966) STN Database Accn. No. 1966:429317.
Starmer, G.A., et al. (1971) Toxicol and Applied Pharm 19(1): 20-28.

* cited by examiner

*Primary Examiner*—Shailendra Kumar
(74) *Attorney, Agent, or Firm*—Stephen G. Kalinchak

(57) ABSTRACT

The present invention relates to aniline derivatives of the general formula I or salts thereof, described therein, and their use.

9 Claims, No Drawings

SUBSTITUTED ANILINE DERIVATIVES

This application is a §365(c) continuation of PCT International Application No. PCT/DK2005/000560, filed Sep. 2, 2005 on behalf of H. Lundbeck A/S, which claims the benefit of priority under 35 U.S.C. §119(e) of U.S. Provisional Application No. 60/609,856, filed Sep. 13, 2004 and claims the benefit of priority under 35 U.S.C. §119(a)-(d) of Danish Application No. PA200401394, filed Sep. 13, 2004, the contents of all of which are hereby incorporated by reference into the subject application.

FIELD OF THE INVENTION

The present invention relates to compounds, which are openers of the KCNQ family potassium ion channels. The compounds are useful in the treatment of disorders and diseases being responsive to opening of the KCNQ family potassium ion channels, one such disease is epilepsy.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction, and cellular secretion.

Humans have over 70 genes encoding potassium channel subtypes (Jentsch *Nature Reviews Neuroscience* 2000, 1, 21-30) with a great diversity with regard to both stucture and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmias, deafness and epilepsy (Jentsch *Nature Reviews Neuroscience* 2000, 1, 21-30).

The KCNQ4 gene is thought to encode the molecular correlate of a potassium channel found in outer hair cells of the cochlea and in Type I hair cells of the vestibular apparatus, in which, mutations can lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 genes are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type, it is dominant in controlling membrane excitability by being the only sustained current in the range of action potential initiation (Marrion *Annual Review Physiology* 1997, 59, 483-504). Modulation of the M-current has dramatic effects on neuronal excitability, for example activation of the current will reduce neuronal excitability. Openers of these KCNQ channels, or activators of the M-current, will reduce excessive neuronal activity and may thus be of use in the treatment of seizures and other diseases and disorders characterised by excessive neuronal activity, such as neuronal hyperexcitability including convulsive disorders, epilepsy and neuropathic pain.

Retigabine (D-23129; N-(2-amino-4-(4-fluorobenzylamino)-phenyl) carbamic acid ethyl ester) and analogues thereof are disclosed in EP554543. Retigabine is an anticonvulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have also been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898).

Retigabine has also been shown to be beneficial in animal models of neuropathic pain (Blackburn-Munro and Jensen *European Journal of Pharmacology* 2003, 460, 109-116), and it is thus suggested that openers of KCNQ channels will be of use in treating pain disorders including neuropathic pain.

The localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society Neuroscience Abstracts* 2003, 53.9).

Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al.

*Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

It is thus suggested that these properties of retigabine and other KCNQ modulators may prevent neuronal damage induced by excessive neuronal activation, and such compounds may be of use in the treatment of neurodegenerative diseases, and be disease modifying (or antiepileptogenic) in patients with epilepsy.

Given that anticonvulsant compounds such as benzodiazepines and chlormethiazole are used clincially in the treatment of the ethanol withdrawal syndrome and that other anticonvulsant compounds e.g. gabapentin, are very effective in animal models of this syndrome (Watson et al. *Neuropharmacology* 1997, 36, 1369-1375), other anticonvulsant compounds such as KCNQ openers are thus expected to be effective in this condition.

mRNA for KCNQ 2 and 3 subunits are found in brain regions associated with anxiety and emotional behaviours such as bipolar disorder e.g. hippocampus and amygdala (Saganich et al. *Journal of Neuroscience* 2001, 21, 4609-4624), and retigabine is reportedly active in some animal models of anxiety-like behaviour (Hartz et al. *Journal of Psychopharmacology* 2003, 17 suppl 3, A28, B16), and other clinically used anticonvulsant compounds are used in the treatment of bipolar disorder. Thus, KCNQ openers may be useful for the treatment of anxiety disorders and bipolar disorder.

WO 200196540 discloses the use of modulators of the M-current formed by expression of KCNQ2 and KCNQ3 genes for insomnia, while WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the treatment of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease; Huntington's chorea; sclerosis such as multiple sclerosis and amyotrophic lateral sclerosis; Creutzfeld-Jakob disease; Parkinson's disease; encephalopathies induced by AIDS or infection by rubella viruses, herpes viruses, borrelia and unknown pathogens; trauma-induced neurodegenerations; neuronal hyperexcitation states such as in medicament withdrawal or intoxication; and neurodegenerative diseases of the peripheral nervous system such as polyneuropathies and polyneuritides.

KCNQ channel openers have also been found to be effective in the treatment of stroke, therefore it can be expected that selective KCNQ openers are effective in the treatment of stroke (Schroder et al., Pflugers Arch., 2003;446(5):607-16; Cooper and Jan, Arch Neurol., 2003, 60(4):496-500; Jensen, CNS Drug Rev., 2002, 8(4):353-60).

KCNQ channels have been shown to be expressed in dopaminergic and cholinergic circuits in the brain that are associated with the brain's reward system, particularly the ventral tegmental area (Cooper et al., J Neurosci, 2001, 21, 9529-9540). Therefore, KCNQ channel openers are expected to be effective in hyperexcitability disorders that involve the brain's reward system such as cocaine abuse, nicotine withdrawal and ethanol withdrawal.

Potassium channels comprised of the KCNQ4 subunits are expressed in the inner ear (Kubisch et al., Cell., 1999 Feb. 5;96(3):437-46) and opening of these channels is therefore expected to treat tinnitus.

Hence, there is a great desire for novel compounds which are potent openers of the KCNQ family of potassium channels.

Also desired are novel compounds with improved properties relative to known compounds, which are openers of the KCNQ family potassium channels, such as retigabine. Improvement of one or more of the following parameters is desired:

half-life, clearance, selectivity, interactions with other medications, bioavailability, potency, formulability, chemical stability, metabolic stability, membrane permeability, solubility and therapeutic index. The improvement of such parameters may lead to improvements such as:
  an improved dosing regime by reducing the number of required doses a day,
  ease of administration to patients on multiple medications,
  reduced side effects,
  enlarged therapeutic index,
  improved tolerability or
  improved compliance.

SUMMARY OF THE INVENTION

One object of the invention is the provision of compounds, which are potent openers of the KCNQ family potassium channels.

The compounds of the invention are substituted aniline derivatives of the below formula I or salts thereof

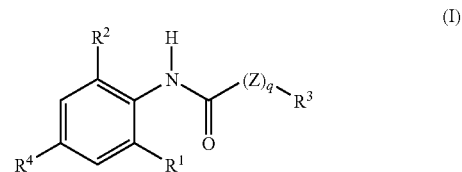

wherein
$R^1$, $R^2$, $R^3$, $R^4$, Z and q are as defined below.

The invention provides a compound of formula I for use as a medicament.

The invention provides a pharmaceutical composition comprising a compound of formula I and a pharmaceutically acceptable carrier or diluent.

The invention provides the use of a compound of formula I for the preparation of a medicament for the treatment of seizure disorders, anxiety disorders, neuropathic pain and migraine pain disorders, neurodegenerative disorders, stroke, cocaine abuse, nicotine withdrawal, ethanol withdrawal or tinnitus.

The invention furthermore concerns the use of a compound of formula I in a method of treatment of seizure disorders, anxiety disorders, neuropathic pain and migraine pain disorders, neurodegenerative disorders, stroke, cocaine abuse, nicotine withdrawal, ethanol withdrawal or tinnitus.

Definition of Substituents

The term heteroatom refers to a nitrogen, oxygen or sulphur atom.

Halogen means fluoro, chloro, bromo or iodo.

Amino means $NH_2$.

The expression "$C_{1-6}$-alk(en/yn)yl" means $C_{1-6}$-alkyl, $C_{2-6}$-alkenyl or $C_{2-6}$-alkynyl. The term "$C_{1-6}$-alkyl" refers to a branched or unbranched alkyl group having from one to six carbon atoms inclusive, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl and hex-3-yl. The term "$C_{2-6}$-alkenyl" designates such groups having from two to six carbon atoms and one double bond, including but not limited to ethenyl, propenyl, and butenyl. The term "$C_{2-6}$-alkynyl" designates such groups having from two to six carbon atoms and one triple bond, including but not limited to ethynyl, propynyl and butynyl.

The expression "$C_{1-8}$-alk(en/yn)yl" means $C_{1-8}$-alkyl, $C_{2-8}$-alkenyl or $C_{2-8}$-alkynyl. The term "$C_{1-8}$-alkyl" refers to a branched or unbranched alkyl group having from one to eight carbon atoms inclusive, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl and hex-3-yl, 1-heptyl, 2-heptyl, 3-heptyl and 4-heptyl. The term "$C_{2-8}$-alkenyl" designates such groups having from two to eight carbon atoms and one double bond, including but not limited to ethenyl, propenyl, and butenyl. The term "$C_{2-8}$-alkynyl" designates such groups having from two to eight carbon atoms and one triple bond, including but not limited to ethynyl, propynyl and butynyl.

The expression "$C_{3-8}$-cycloalk(en)yl" means $C_{3-8}$-cycloalkyl or $C_{3-8}$-cycloalkenyl. The term "$C_{3-8}$-cycloalkyl" designates a monocyclic or bicyclic carbocycle having three to eight C-atoms; including but not limited to cyclopropyl, cyclopentyl, cyclohexyl, bicycloheptyl such as 2-bicyclo[2.2.1]heptyl. The term "$C_{3-8}$-cycloalkenyl" designates a monocyclic or bicyclic carbocycle having three to eight C-atoms and one double bond, including but not limited to cyclopropenyl, cyclopentenyl and cyclohexenyl.

The term "$C_{3-8}$-heterocycloalk(en)yl" means $C_{3-8}$-heterocycloalkyl or $C_{3-8}$-heterocycloalkenyl. The term "$C_{3-8}$-heterocycloalkyl" designates a monocyclic or bicyclic ring system wherein the ring is formed by 3 to 8 atoms selected from 2-7 carbon atoms and 1 or 2 heteroatoms independently selected from N, S, or O. Examples of $C_{3-8}$-heterocycloalkyles are pyrrolidine, azepan, morpholine and piperidine. The term "$C_{3-8}$-heterocycloalkenyl" designates a monocyclic or bicyclic ring system with one double bond, wherein the ring is formed by 3 to 8 atoms selected from 2-7 carbon atoms and 1 or 2 heteroatoms independently selected from N, S, or O.

The term Aryl refers to monocyclic or bicyclic aromatic systems of 5-10 carbon atoms, including but not limited to phenyl and naphthyl. Any Aryl which is mentioned either alone or as a part of a larger substituent is optionally substituted and may thus be substituted with one or more substituents such as with 0, 1, 2, 3 or 4 substituents. Any Aryl which is mentioned either alone or as a part of a larger substituent may thus be substituted with one or more substituents independently selected from the group consisting of amino, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{3-8}$-heterocycloalk(en)yl, $C_{1-6}$-alkyl-$C_{3-8}$-heterocycloalk(en)yl, hydroxy, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, halo-$C_{1-6}$-alk(en/yn)yloxy, halo-$C_{3-8}$-cycloalk(en)yloxy, halo-$C_{3-8}$-cycloalk(en)yl-$C_{1-6}$-alk(en/yn)yloxy, $C_{1-6}$-alk(en/yn)ylamino, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which optionally contains one or two heteroatoms and which is optionally substituted with one or more $C_{1-6}$-alk(en/yn)yl groups. When two adjacent substituents together with the Aryl group to which they are attached form a 4-8 membered ring, which optionally contains one or two heteroatoms, then a ring system is formed by 4-8 atoms selected from 3-8 carbon atoms and 0-2 heteroatoms independently selected from N, S, or O. Such two adjacent substituents may together form: —$(CH_2)_n$—O—, —O—$(CH_2)_m$—O—, —$CH_2$—O—$(CH_2)_p$—O—, —$CH_2$—O—$CH_2$—O—$CH_2$—, —O—C$(CH_3)_2$—$(CH_2)_m$—, —$(CH_2)_n$—S—, —S—$(CH_2)_m$—S—, —$CH_2$—S—$(CH_2)_p$—S— or —$CH_2$—S—$CH_2$—S—$CH_2$—, —S—C$(CH_3)_2$—$(CH_2)_m$—; wherein m is 1, 2 or 3, n is 2, 3 or 4 and p is 1 or 2.

The term "Heteroaryl" refers to monocyclic or bicyclic heteroaromatic systems of 5-10 atoms selected from 1, 2, 3, 4, 5, 6, 7, 8 or 9 carbon atoms and 1, 2, 3 or 4 heteroatoms independently selected from N, S, or O, including but not limited to pyridine, pyrrole, pyrimidine, quinoline, indole, thiophene, furan, imidazoles such as 3H-imidazol and 1H-imidazol, triazoles such as [1,2,3]triazole and [1,2,4]triazole, tetrazoles such as 2H-tetrazole and oxazole. Any Heteroaryl which is mentioned either alone or as a part of a larger substituent is optionally substituted and may thus be substituted with one or more substituents such as with 0, 1, 2, 3 or 4 substituents. Any Heteroaryl which is mentioned either alone or as a part of a larger substituent may thus be substituted with one or more substituents independently selected from the group consisting of halogen, cyano, amino, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yl, $C_{3-8}$-cycloalk(en)yl, $C_{3-8}$-cycloalk(en)yl-$C_{1-6}$-alk(en/yn)yl, Aryl, Aryl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{1-6}$-alk(en/yn)yl-phenoxy, $C_{3-8}$-cycloalk(en)yl-phenoxy, $C_{3-8}$-cycloalk(en)yl-$C_{1-6}$-alk(en/yn)yl-phenoxy, amino-phenoxy, halo-phenoxy, cyano-phenoxy, halo-$C_{1-6}$-alk(en/yn)yl-phenoxy, halo-$C_{3-8}$-cycloalk(en)yl-phenoxy, halo-$C_{3-8}$-cycloalk(en)yl-$C_{1-6}$-alk(en/yn)yl-phenoxy, $C_{3-8}$-heterocycloalk(en)yl-phenoxy, $C_{1-6}$-alkyl-$C_{3-8}$-heterocycloalk(en)yl-phenoxy, hydroxy-phenoxy, $C_{1-6}$-alk(en/yn)yloxy-phenoxy, $C_{3-8}$-cycloalk(en)yloxy-phenoxy, $C_{3-8}$-cycloalk(en)yl-$C_{1-6}$-alk(en/yn)yloxy-phenoxy, halo-$C_{1-6}$-alk(en/yn)yloxy-phenoxy, halo-$C_{3-8}$-cycloalk(en)yloxy-phenoxy, halo-$C_{3-8}$-cycloalk(en)yl-$C_{1-6}$-alk(en/yn)yloxy-phenoxy, $C_{1-6}$-alk(en/yn)ylamino-phenoxy, di-($C_{1-6}$-alk(en/yn)yl)amino-phenoxy, $C_{1-6}$-alk(en/yn)yl-CO—NH-phenoxy and $C_{1-6}$-alk(en/yn)yl-sulfonamide-phenoxy.

The term "halo-$C_{1-6}$-alk(en/yn)yl" designates $C_{1-6}$-alk(en/yn)yl being substituted with one or more halogen atoms, including but not limited to trifluoromethyl and 3,3,3-trifluoro-1-propyl. Similarly, halo-$C_{3-8}$-cycloalk(en)yl designates $C_{3-8}$-cycloalk(en)yl being substituted with one or more halogen atoms and "halo-phenoxy" designates phenoxy being substituted with one or more halogen atoms.

The term "amino-$C_{1-6}$-alk(en/yn)yl" designates $C_{1-6}$-alk(en/yn)yl being substituted with one amino group, including but not limited to 1-amino-2-methyl-prop-1-yl and 1-amino-3-methyl-but-1-yl. Similarly, amino-$C_{3-8}$-cycloalk(en)yl designates $C_{3-8}$-cycloalk(en)yl being substituted with one amino group and amino-$C_{3-8}$-cycloalk(en)yl-$C_{1-6}$-alk(en/yn)yl designates $C_{3-8}$-cycloalk(en)yl-$C_{1-6}$-alk(en/yn)yl being wherein $C_{3-8}$-cycloalk(en)yl is substituted with one amino group.

In the expressions $C_{3-8}$-cycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, Aryl-$C_{3-8}$-heterocycloalk(en)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, halo-$C_{3-8}$-cycloalk(en)yl-$C_{1-6}$-alk(en/yn)yl, halo-$C_{1-6}$-alk(en/yn)yl-$C_{3-8}$-heterocycloalk(en)yl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yloxy, halo-$C_{3-8}$-cycloalk(en)yloxy, halo-$C_{3-8}$-cycloalk(en)yl-$C_{1-6}$-alk(en/yn)yloxy, amino-$C_{1-6}$-alk(en/yn)yl, amino-$C_{3-8}$-cycloalk(en)yl, amino-$C_{3-8}$-cycloalk(en)yl-$C_{1-6}$-alk(en/yn)yl, $R^7NH$—$C_{1-6}$-alk(en/yn)yl, $C_{1-6}$-alk(en/yn)ylamino, di-($C_{1-6}$-alk(en/yn)yl)amino, $C_{1-6}$-alk(en/yn)yl-CO—NH—, $C_{1-6}$-alk(en/yn)yl-sulfonamide $C_{1-6}$-alk(en/yn)yl-phenoxy, $C_{3-8}$-cycloalk(en)yl-phenoxy, $C_{3-8}$-cycloalk(en)yl-$C_{1-6}$-alk(en/yn)yl-phenoxy, halo-phenoxy, halo-$C_{1-6}$-alk(en/yn)yl-phenoxy, halo-$C_{3-8}$-cycloalk(en)yl-phenoxy, halo-$C_{3-8}$-cycloalk(en)yl-$C_{1-6}$-alk(en/yn)yl-phenoxy, $C_{3-8}$-heterocycloalk(en)yl-phenoxy, $C_{1-6}$-alkyl-$C_{3-8}$-heterocycloalk(en)yl-phenoxy, $C_{1-6}$-alk(en/yn)yloxy-phenoxy, $C_{3-8}$-cycloalk(en)yloxy-phenoxy, $C_{3-8}$-cycloalk(en)yl-$C_{1-6}$-alk(en/yn)yloxy-phenoxy, halo-$C_{1-6}$-alk(en/yn)yloxy-phenoxy, halo-$C_{3-8}$-cycloalk(en)yloxy-phenoxy, halo-$C_{3-8}$-cycloalk(en)yl-$C_{1-6}$-alk(en/yn)yloxy-phenoxy, $C_{1-6}$-alk(en/yn)ylamino-phenoxy, di-($C_{1-6}$-alk(en/yn)yl)amino-phenoxy, $C_{1-6}$-alk(en/yn)yl-CO—NH-phenoxy and $C_{1-6}$-alk(en/yn)yl-sulfonamide-phenoxy the terms "$C_{1-6}$-alk(en/yn)yl", "$C_{3-8}$-cycloalk(en)yl", "$C_{3-8}$-heterocycloalk(en)yl", "Aryl", "Heteroaryl", "halo-$C_{1-6}$-alk(en/yn)yl", "halo-$C_{3-8}$-cycloalk(en)yl", "halo-phenoxy", "amino-$C_{1-6}$-alk(en/yn)yl", "amino-$C_{3-8}$-cycloalk(en)yl" and "amino-$C_{3-8}$-cycloalk(en)yl-$C_{1-6}$-alk(en/yn)yl" are as defined above.

Any $C_{1-6}$-alk(en/yn)yl which is mentioned either alone or as a part of a larger substituent independently contains 1, 2, 3, 4, 5 or 6 carbon atoms.

Any $C_{1-8}$-alk(en/yn)yl which is mentioned either alone or as a part of a larger substituent independently contains 1, 2, 3, 4, 5, 6, 7 or 8 carbon atoms.

Any $C_{3-8}$-cycloalk(en)yl which is mentioned either alone or as a part of a larger substituent independently contains 3, 4, 5, 6, 7 or 8 carbon atoms.

Any $C_{3-8}$-heterocycloalk(en)yl which is mentioned either alone or as a part of a larger substituent independently contains 2, 3, 4, 5, 6 or 7 carbon atoms and 1 or 2 heteroatoms.

Any Aryl which is mentioned either alone or as a part of a larger substituent independently contains 5, 6, 7, 8, 9 or 10 carbon atoms.

Any Heteroaryl which is mentioned either alone or as a part of a larger substituent independently contains 5, 6, 7, 8, 9 or 10 atoms selected from 1, 2, 3, 4, 5, 6, 7, 8 or 9 carbon atoms and 1, 2, 3 or 4 heteroatoms.

DESCRIPTION OF THE INVENTION

The present invention relates to substituted aniline derivatives which are potent openers of KCNQ potassium channels.

The present invention relates to a compound represented by the general formula I or salts thereof:

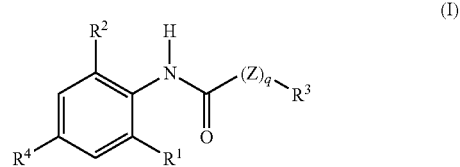

wherein

Z is O or S;

q is 0 or 1;

each of $R^1$ and $R^2$ is independently selected from the group consisting of halogen, cyano, amino, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy;

$R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, amino-$C_{1-6}$-alk(en/yn)yl, amino-$C_{3-8}$-cycloalk(en)yl, amino-$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl;

$R^4$ is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, Aryl-$C_{3-8}$-heterocycloalk(en)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, halo-$C_{1-6}$-alk(en/yn)yl-$C_{3-8}$-heterocycloalk(en)yl-$C_{1-6}$-alk(en/yn)yl, $NR^5R^6$ and $R^7NH$—$C_{1-6}$-alk(en/yn)yl; wherein $R^5$ and $R^6$ are independently selected from the group consisting of hydrogen, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{1-6}$-alk(en/yn)yl, $C_{3-8}$-cycloalk(en)yl, $C_{3-8}$-cycloalk(en)yl-$C_{1-6}$-alk(en/yn)yl, Heteroaryl-$C_{1-6}$-alk(en/yn)yl, Heteroaryl-$C_{3-8}$-cycloalk(en)yl and Heteroaryl-$C_{3-8}$-cycloalk(en)yl-$C_{1-6}$-alk(en/yn)yl with the proviso that $R^5$ and $R^6$ are not hydrogen at the same time; and $R^7$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl and Heteroaryl.

In one embodiment of the compound of formula I $R^1$ is selected from the group consisting of $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy;

in a further embodiment of the compound of formula I, $R^1$ is selected from the group consisting of halogen, cyano, amino, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en) yl, Aryl, Heteroaryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and $C_{1-6}$-alk(en/yn)yloxy;

in a further embodiment of the compound of formula I, $R^1$ is selected from the group consisting of halogen, amino, $C_{1-6}$-alk(en/yn)yl, $C_{3-8}$-heterocycloalk(en)yl, Aryl, Heteroaryl, halo-$C_{1-6}$-alk(en/yn)yl and $C_{1-6}$-alk(en/yn)yloxy.

Typically $R^1$ is selected from the group consisting of halogen, amino, $C_{1-6}$-alk(en/yn)yl, $C_{3-8}$-heterocycloalk(en)yl, Aryl, Heteroaryl and halo-$C_{1-6}$-alk(en/yn)yl.

In one embodiment of the compound of formula I $R^2$ is selected from the group consisting of $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy;

in a further embodiment of the compound of formula I $R^2$ is selected from the group consisting of halogen, cyano, amino, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and $C_{1-6}$-alk(en/yn)yloxy;

in a further embodiment of the compound of formula I, $R^2$ is selected from the group consisting of halogen, amino, $C_{1-6}$-alk(en/yn)yl, $C_{3-8}$-heterocycloalk(en)yl, Aryl, Heteroaryl, halo-$C_{1-6}$-alk(en/yn)yl and $C_{1-6}$-alk(en/yn)yloxy.

Typically $R^2$ is selected from the group consisting of halogen, amino, $C_{1-6}$-alk(en/yn)yl, $C_{3-8}$-heterocycloalk(en)yl, Aryl, Heteroaryl and halo-$C_{1-6}$-alk(en/yn)yl.

To further illustrate without limiting the invention, an embodiment concerns such compounds wherein $R^1$ or $R^2$ is halogen such as chloro, bromo or fluoro;

in a further embodiment $R^1$ and $R^2$ are independently selected halogen atoms such as chloro or bromo;

in a further embodiment $R^1$ and $R^2$ is amino;

in a further embodiment $R^1$ and $R^2$ is $C_{1-6}$-alk(en/yn)yl such as methyl;

in a further embodiment $R^1$ and $R^2$ are $C_{1-6}$-alk(en/yn)yl such as methyl;

in a further embodiment $R^1$ and $R^2$ is $C_{1-6}$-alk(en/yn)yl such as methyl and the remainder of $R^1$ and $R^2$ is halogen such as chloro, or bromo;

in a further embodiment $R^1$ or $R^2$ is $C_{3-8}$-heterocycloalk(en)yl such as morpholinyl;

in a further embodiment $R^1$ or $R^2$ is optionally substituted Aryl such as optionally substituted phenyl;

in a further embodiment $R^1$ or $R^2$ is $C_{1-6}$-alk(en/yn)yl such as methyl and the remainder of $R^1$ and $R^2$ is optionally substituted Aryl such as optionally substituted phenyl;

in a further embodiment $R^1$ or $R^2$ is optionally substituted Heteroaryl such as optionally substituted quinolinyl;

in a further embodiment $R^1$ or $R^2$ is halo-$C_{1-6}$-alk(en/yn)yl such as trifluoromethyl.

In one embodiment of the compound of formula I q is 0; in a further embodiment q is 1.

In one embodiment of the compound of formula I q is 1 and Z is an oxygen atom; in a further embodiment q is 1 and Z is a sulphur atom.

In one embodiment of the compound of formula I $R^3$ is selected from the group consisting of $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl.

In a further embodiment of the compound of formula I $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Heteroaryl-$C_{1-6}$-alk(en/yn)yl, Heteroaryl-$C_{3-8}$-cycloalk(en)yl, Heteroaryl-$C_{3-8}$-cycloalk(en)yl-$C_{1-6}$-alk(en/yn)yl, amino-$C_{1-6}$-alk(en/yn)yl, amino-$C_{3-8}$-cycloalk(en)yl, amino-$C_{3-8}$-cycloalk(en)yl-$C_{1-6}$-alk(en/yn)yl and $C_{1-6}$-alk(en/yn)yloxy-$C_{1-6}$-alk(en/yn)yl.

In a further embodiment of the compound of formula I $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, $C_{3-8}$-heterocycloalk(en)yl-$C_{1-6}$-alk(en/yn)yl, $C_{1-6}$-alk(en/yn)yl-$C_{3-8}$-heterocycloalk(en)yl-$C_{1-6}$-alk(en/yn)yl, Heteroaryl-$C_{1-6}$-alk(en/yn)yl, amino-$C_{1-6}$-alk(en/yn)yl and $C_{1-6}$-alk(en/yn)yloxy-$C_{1-6}$-alk(en/yn)yl.

Typically, $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Heteroaryl-$C_{1-6}$-alk(en/yn)yl and amino-$C_{1-6}$-alk(en/yn)yl.

To further illustrate without limiting the invention, an embodiment concerns such compounds wherein $R^3$ is $C_{1-8}$-alk(en/yn)yl comprising 1, 2, 3, 4, 5, 6, 7 or 8 carbon atoms;

in a further embodiment $R^3$ is $C_{3-8}$-cycloalk(en)yl such as cyclohexyl;

in a further embodiment $R^3$ is $C_{3-8}$-cycloalk(en)yl-$C_{1-6}$-alk(en/yn)yl such as cyclopentyl-methyl, cyclohexyl-ethyl or bicycloheptyl-methyl;

in a further embodiment $R^3$ is Aryl-$C_{1-6}$-alk(en/yn)yl wherein Aryl is optionally substituted, such as phenyl-methyl wherein phenyl is optionally substituted;

in a further embodiment $R^3$ is Aryl-$C_{3-8}$-cycloalk(en)yl wherein Aryl is optionally substituted, such as phenyl-cyclopropyl wherein phenyl is optionally substituted;

in a further embodiment $R^3$ is Heteroaryl-$C_{1-6}$-alk(en/yn)yl wherein Heteroaryl is optionally substituted, such as thiophenyl-methyl wherein thiophenyl is optionally substituted;

in a further embodiment $R^3$ is amino-$C_{1-6}$-alk(en/yn)yl such as 1-amino-2-methyl-prop-1-yl or 1-amino-3-methyl-but-1-yl.

To further illustrate without limiting the invention an embodiment concerns such compounds of formula I wherein $R^3$ is not $C_{3-8}$-heterocycloalk(en)yl-$C_{1-6}$-alk(en/yn)yl such as $C_{3-8}$-heterocycloalk(en)yl-methyl;

in a further embodiment $R^3$ is not halo-methyl wherein halo refers to eg. chloro or bromo;

in a further embodiment $R^3$ is not methyl;

in a further embodiment q is 1, Z is O and $R^3$ is different from 2-methyl-prop-2-yl.

In a further embodiment of the compound of formula I $R^4$ is selected from the group consisting of halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and halo-$C_{1-6}$-alk(en/yn)yl-$C_{3-8}$-heterocycloalk(en)yl-$C_{1-6}$-alk(en/yn)yl;

in a further embodiment $R^4$ is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, Aryl-$C_{3-8}$-heterocycloalk(en)yl, halo-$C_{1-6}$-alk(en/yn)yl-$C_{3-8}$-heterocycloalk(en)yl-$C_{1-6}$-alk(en/yn)yl, $NR^5R^6$ and $R^7NH$—$C_{1-6}$-alk(en/yn)yl;

in a further embodiment $R^4$ is selected from the group consisting of halogen, $C_{1-6}$-alk(en/yn)yl, $C_{3-8}$-heterocycloalk(en)yl, Heteroaryl, Aryl-$C_{3-8}$-heterocycloalk(en)yl, halo-$C_{1-6}$-alk(en/yn)yl-$C_{3-8}$-heterocycloalk(en)yl-$C_{1-6}$-alk(en/yn)yl, $NR^5R^6$ and $R^7NH$—$C_{1-6}$-alk(en/yn)yl.

Typically, $R^4$ is selected from the group consisting of halogen, $C_{1-6}$-alk(en/yn)yl, $C_{3-8}$-heterocycloalk(en)yl, Heteroaryl, Aryl-$C_{3-8}$-heterocycloalk(en)yl, $NR^5R^6$ and $R^7NH$—$C_{1-6}$-alk(en/yn)yl.

To further illustrate without limiting the invention, an embodiment concerns such compounds wherein $R^4$ is halogen, such as bromo, chloro or fluoro;

in a further embodiment $R^4$ is $C_{1-6}$-alk(en/yn)yl, such as methyl;

in a further embodiment $R^4$ is $C_{3-8}$-heterocycloalk(en)yl, such as azepanyl;

in a further embodiment $R^4$ is Heteroaryl, such as pyrrolyl;

in a further embodiment $R^4$ is Aryl-$C_{3-8}$-heterocycloalk(en)yl wherein Aryl is optionally substituted, such as phenyl-pyrrolidinyl wherein phenyl is optionally substituted;

in a further embodiment $R^4$ is $NR^5R^6$;

in a further embodiment $R^4$ is $R^7NH$—$C_{1-6}$-alk(en/yn)yl.

To further illustrate without limiting the invention an embodiment concerns such compounds of formula I wherein no more than two of the three substituents $R^1$, $R^2$ and $R^4$ are identical.

In a further embodiment of the compound of formula I $R^5$ and $R^6$ are independently selected from the group consisting of Aryl-$C_{3-8}$-cycloalk(en)yl, Aryl-$C_{3-8}$-cycloalk(en)yl-$C_{1-6}$-alk(en/yn)yl, $C_{3-8}$-cycloalk(en)yl, $C_{3-8}$-cycloalk(en)yl-$C_{1-6}$-alk(en/yn)yl, Heteroaryl-$C_{3-8}$-cycloalk(en)yl and Heteroaryl-$C_{3-8}$-cycloalk(en)yl-$C_{1-6}$-alk(en/yn)yl;

in a further embodiment $R^5$ or $R^6$ is selected from the group consisting of Aryl-$C_{3-8}$-cycloalk(en)yl, Aryl-$C_{3-8}$-cycloalk(en)yl-$C_{1-6}$-alk(en/yn)yl, $C_{3-8}$-cycloalk(en)yl, $C_{3-8}$-cycloalk(en)yl-$C_{1-6}$-alk(en/yn)yl, Heteroaryl-$C_{3-8}$-cycloalk(en)yl and Heteroaryl-$C_{3-8}$-cycloalk(en)yl-$C_{1-6}$-alk(en/yn)yl and the remainder of $R^5$ and $R^6$ is selected from the group consisting of hydrogen, Aryl-$C_{1-6}$-alk(en/yn)yl, $C_{1-6}$-alk(en/yn)yl and Heteroaryl-$C_{1-6}$-alk(en/yn)yl.

Typically $R^5$ and $R^6$ are independently selected from the group consisting of hydrogen, Aryl-$C_{1-6}$-alk(en/yn)yl, $C_{1-6}$-alk(en/yn)yl and Heteroaryl-$C_{1-6}$-alk(en/yn)yl with the proviso that $R^5$ and $R^6$ are not hydrogen at the same time.

To further illustrate without limiting the invention, an embodiment concerns such compounds wherein $R^5$ or $R^6$ is hydrogen;

in a further embodiment $R^5$ or $R^6$ is Aryl-$C_{1-6}$-alk(en/yn)yl, such as phenyl-methyl;

in a further embodiment $R^5$ or $R^6$ is $C_{1-6}$-alk(en/yn)yl, such as methyl;

in a further embodiment $R^5$ or $R^6$ is Heteroaryl-$C_{1-6}$-alk(en/yn)yl, such as thiophenyl-methyl, pyrimidinyl-methyl or pyridinyl-methyl;

in a further embodiment one of $R^5$ and $R^6$ is hydrogen or $C_{1-6}$-alk(en/yn)yl such as methyl and the remainder of $R^5$ and $R^6$ is Aryl-$C_{1-6}$-alk(en/yn)yl such as phenyl-methyl or Heteroaryl-$C_{1-6}$-alk(en/yn)yl such as thiophenyl-methyl, pyrimidinyl-methyl or pyridinyl-methyl.

In a further embodiment of the compound of formula I $R^7$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl and Heteroaryl.

Typically, $R^7$ is selected from the group consisting of Aryl, halo-$C_{1-6}$-alk(en/yn)yl, Aryl-$C_{1-6}$-alk(en/yn)yl and Heteroaryl.

To further illustrate without limiting the invention, an embodiment concerns such compounds wherein $R^7$ is Aryl, such as phenyl.

In further embodiments of the compound of formula I any Aryl which is mentioned either alone or as a part of a larger substituent is optionally substituted with one or more substituents independently selected from the group consisting of $C_{3-8}$-cycloalk(en)yl, $C_{3-8}$-cycloalk(en)yl-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{3-8}$-heterocycloalk(en)yl, $C_{1-6}$-alkyl-$C_{3-8}$-heterocycloalk(en)yl, $C_{3-8}$-cycloalk(en)yloxy, $C_{3-8}$-cycloalk(en)yl-$C_{1-6}$-alk(en/yn)yloxy, halo-$C_{3-8}$-cycloalk(en)yloxy, halo-$C_{3-8}$-cycloalk(en)yl-$C_{1-6}$-alk(en/yn)yloxy, $C_{1-6}$-alk(en/yn)ylamino.

Typically, any Aryl which is mentioned either alone or as a part of a larger substituent is optionally substituted with one or more substituents independently selected from the group consisting of amino, halogen, cyano, $C_{1-6}$-alk(en/yn)yl, halo-$C_{1-6}$-alk(en/yn)yl, hydroxy, $C_{1-6}$-alk(en/yn)yloxy, halo-$C_{1-6}$-alk(en/yn)yloxy, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which optionally contains one or two heteroatoms and which is optionally substituted with one or more $C_{1-6}$-alk(en/yn)yl groups.

In further embodiments of the compound of formula I, any Aryl which is mentioned either alone or as a part of a larger substituent is unsubstituted;

in further embodiments; any Aryl which is mentioned either alone or as a part of a larger substituent is monosubstituted;

in further embodiments, any Aryl which is mentioned either alone or as a part of a larger substituent is disubstituted;

in further embodiments any Aryl which is mentioned either alone or as a part of a larger substituent is trisubstituted.

In further embodiments of the compound of formula I, any Aryl which is mentioned either alone or as a part of a larger substituent is phenyl which is optionally substituted;

in further embodiments, any phenyl which is mentioned either alone or as a part of a larger substituent is unsubstituted;

in further embodiments, any phenyl which is mentioned either alone or as a part of a larger substituent is monosubstituted such as in the ortho position or in the meta position or in the para position;

in further embodiments, any phenyl which is mentioned either alone or as a part of a larger substituent is disubstituted such as in the meta position and in the para position or in both meta positions;

in further embodiments, any phenyl which is mentioned either alone or as a part of a larger substituent is trisubstituted.

To further illustrate without limiting the invention, embodiments concern such compounds wherein any Aryl which is mentioned either alone or as a part of a larger substituent in any of substituents $R^1$ and $R^2$ is optionally substituted with one or more substituents independently selected from the group consisting of amino, halogen such as fluoro or cyano, $C_{1-6}$-alk(en/yn)yl such as methyl, ethenyl or isopropyl, halo-$C_{1-6}$-alk(en/yn)yl such as trifluoromethyl, hydroxy, $C_{1-6}$-alk(en/yn)yloxy such as methoxy, halo-$C_{1-6}$-alk(en/yn)yloxy such as trifluoromethoxy, di-($C_{1-6}$-alk(en/yn)yl)amino such as dimethylamino, $C_{1-6}$-alk(en/yn)yl-CO—NH— such as $CH_3$—CO—NH—, $C_{1-6}$-alk(en/yn)yl-sulfonamide such as methylsulfonamide; or two adjacent substituents may together with the Aryl group to which they are attached form a 4-8 membered ring which optionally contains one or two heteroatoms and which is optionally substituted with one or more $C_{1-6}$-alk(en/yn)yl groups, such two adjacent substituents may together form eg. —O—$CH_2$—$CH_2$—O— or —O—$C(CH_3)_2$—$CH_2$—.

To further illustrate without limiting the invention, embodiments concern such compounds wherein any Aryl which is mentioned either alone or as a part of a larger substituent in $R^3$ is optionally substituted with one or more halogen atoms such as fluoro or chloro atoms.

To further illustrate without limiting the invention, embodiments concern such compounds wherein any Aryl which is mentioned either alone or as a part of a larger substituent in $R^5$ or $R^6$ is optionally substituted with one or more substituents independently selected from the group consisting of halogen such as fluoro and halo-$C_{1-6}$-alk(en/yn)yl such as trifluoromethyl.

To further illustrate without limiting the invention, embodiments concerns such compounds wherein any Aryl which is mentioned either alone or as a part of a larger substituent in $R^7$ is optionally substituted with one or more substituents independently selected from the group consisting of halogen such as fluoro or chloro, $C_{1-6}$-alk(en/yn)yl such as methyl, halo-$C_{1-6}$-alk(en/yn)yl such as trifluoromethyl and $C_{1-6}$-alk(en/yn)yloxy such as methoxy.

In further embodiments of the compound of formula I any Heteroaryl which is mentioned either alone or as a part of a larger substituent is optionally substituted with one or more substituents independently selected from the group consisting of cyano, amino, halo-$C_{3-8}$-cycloalk(en)yl, halo-$C_{3-8}$-cycloalk(en)yl-$C_{1-6}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, $C_{3-8}$-cycloalk(en)yloxy, $C_{3-8}$-cycloalk(en)yl-$C_{1-6}$-alk(en/yn)yloxy, $C_{3-8}$-cycloalk(en)yl-phenoxy, $C_{3-8}$-cycloalk(en)yl-$C_{1-6}$-alk(en/yn)yl-phenoxy, amino-phenoxy, halo-phenoxy, cyano-phenoxy, halo-$C_{1-6}$-alk(en/yn)yl-phenoxy, halo-$C_{3-8}$-cycloalk(en)yl-phenoxy, halo-$C_{3-8}$-cycloalk(en)yl-$C_{1-6}$-alk(en/yn)yl-phenoxy, $C_{3-8}$-heterocycloalk(en)yl-phenoxy, $C_{1-6}$-alkyl-$C_{3-8}$-heterocycloalk(en)yl-phenoxy, hydroxy-phenoxy, $C_{1-6}$-alk(en/yn)yloxy-phenoxy, $C_{3-8}$-cycloalk(en)yloxy-phenoxy, $C_{3-8}$-cycloalk(en)yl-$C_{1-6}$-alk(en/yn)yloxy-phenoxy, halo-$C_{1-6}$-alk(en/yn)yloxy-phenoxy, halo-$C_{3-8}$-cycloalk(en)yloxy-phenoxy, halo-$C_{3-8}$-cycloalk(en)yl-$C_{1-6}$-alk(en/yn)yloxy-phenoxy, $C_{1-6}$-alk(en/yn)ylamino-phenoxy, di-($C_{1-6}$-alk(en/yn)yl)amino-phenoxy, $C_{1-6}$-alk(en/yn)yl-CO—NH-phenoxy and $C_{1-6}$-alk(en/yn)yl-sulfonamide-phenoxy.

Typically, any Heteroaryl which is mentioned either alone or as a part of a larger substituent is optionally substituted with one or more substituents independently selected from the group consisting of halogen, halo-$C_{1-6}$-alk(en/yn)yl, $C_{1-6}$-alk(en/yn)yl, Aryl, $C_{1-6}$-alk(en/yn)yloxy and $C_{1-6}$-alk(en/yn)yl-phenoxy.

To further illustrate without limiting the invention, embodiments of formula I concern such compounds wherein any Heteroaryl which is mentioned either alone or as a part of a larger substituent is unsubstituted;

in further embodiments any Heteroaryl which is mentioned either alone or as a part of a larger substituent is monosubstituted;

in further embodiments any Heteroaryl which is mentioned either alone or as a part of a larger substituent is disubstituted;

in further embodiments any Heteroaryl which is mentioned either alone or as a part of a larger substituent is trisubstituted.

To further illustrate without limiting the invention, an embodiment concerns such compounds wherein any Heteroaryl which is mentioned either alone or as a part of a larger substituent in $R^5$ or $R^6$ is optionally substituted with one or more substituents independently selected from the group consisting of halogen such as chloro, halo-$C_{1-6}$-alk(en/yn)yl such as trifluoromethyl, $C_{1-6}$-alk(en/yn)yl such as methyl, Aryl such as phenyl, $C_{1-6}$-alk(en/yn)yloxy such as methoxy and $C_{1-6}$-alk(en/yn)yl-phenoxy such as methyl-phenoxy.

To further illustrate without limiting the invention, an embodiment of formula I relates to a compound having the general formula XXVI or salts thereof:

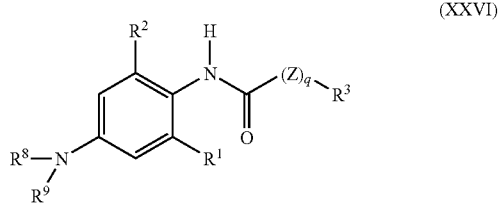

(XXVI)

wherein Z, q, $R^1$, $R^2$ and $R^3$ are as defined above;

and $R^8$ and $R^9$ are independently selected from the group consisting of hydrogen, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{1-6}$-alk(en/yn)yl, $C_{3-8}$-cycloalk(en)yl, $C_{3-8}$-cycloalk(en)yl-$C_{1-6}$-alk(en/yn)yl, Heteroaryl-$C_{1-6}$-alk(en/yn)yl, Heteroaryl-$C_{3-8}$-cycloalk(en)yl and Heteroaryl-$C_{3-8}$-cycloalk(en)yl-$C_{1-6}$-alk(en/yn)yl with the proviso that $R^8$ and $R^9$ are not hydrogen at the same time.

In one embodiment of the compound of formula XXVI $R^1$ and $R^2$ are independently selected from the group consisting of halogen, amino, $C_{1-6}$-alk(en/yn)yl, $C_{3-8}$-heterocycloalk(en)yl, Aryl, Heteroaryl and halo-$C_{1-6}$-alk(en/yn)yl.

In one embodiment of the compound of formula XXVI q is 0.

In one embodiment of the compound of formula XXVI q is 1.

In one embodiment of the compound of formula XXVI Z is an oxygen atom.

In one embodiment of the compound of formula XXVI $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Heteroaryl-$C_{1-6}$-alk(en/yn)yl and amino-$C_{1-6}$-alk(en/yn)yl.

In one embodiment of the compound of formula XXVI any Aryl which is mentioned either alone or as a part of a larger substituent is optionally substituted with one or more substituents independently selected from the group consisting of amino, halogen, cyano, $C_{1-6}$-alk(en/yn)yl, halo-$C_{1-6}$-alk(en/yn)yl, hydroxy, $C_{1-6}$-alk(en/yn)yloxy, halo-$C_{1-6}$-alk(en/yn)yloxy, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which optionally contains one or two heteroatoms and which is optionally substituted with one or more $C_{1-6}$-alk(en/yn)yl groups.

In one embodiment of the compound of formula XXVI any Heteroaryl which is mentioned either alone or as a part of a larger substituent is optionally substituted with one or more substituents independently selected from the group consisting of halogen, halo-$C_{1-6}$-alk(en/yn)yl, $C_{1-6}$-alk(en/yn)yl, Aryl, $C_{1-6}$-alk(en/yn)yloxy and $C_{1-6}$-alk(en/yn)yl-phenoxy.

To further illustrate without limiting the invention, an embodiment of formula I relates to a compound having the general formula XXVII or salts thereof:

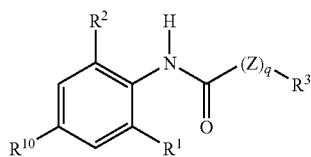

(XXVII)

wherein Z, q, $R^1$, $R^2$ and $R^3$ are as defined above;

and $R^{10}$ is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, Aryl-$C_{3-8}$-heterocycloalk(en)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and halo-$C_{1-6}$-alk(en/yn)yl-$C_{3-8}$-heterocycloalk(en)yl-$C_{1-6}$-alk(en/yn)yl.

In one embodiment of the compound of formula XXVII $R^1$ and $R^2$ are independently selected from the group consisting of halogen, amino, $C_{1-6}$-alk(en/yn)yl, $C_{3-8}$-heterocycloalk(en)yl, Aryl, Heteroaryl and halo-$C_{1-6}$-alk(en/yn)yl.

In one embodiment of the compound of formula XXVII q is 0.

In one embodiment of the compound of formula XXVII q is 1.

In one embodiment of the compound of formula XXVII Z is an oxygen atom.

In one embodiment of the compound of formula XXVII $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Heteroaryl-$C_{1-6}$-alk(en/yn)yl and amino-$C_{1-6}$-alk(en/yn)yl.

In one embodiment of the compound of formula XXVII $R^{10}$ is selected from the group consisting of cyano, halogen, preferably bromo or chloro and $C_{1-6}$-alk(en/yn)yl, preferably methyl.

In one embodiment of the compound of formula XXVII $R^{10}$ is selected from the group consisting of $C_{3-8}$-cycloalk(en)yl, $C_{3-8}$-cycloalk(en)yl-$C_{1-6}$-alk(en/yn)yl, $C_{3-8}$-heterocycloalk(en)yl, Aryl, Heteroaryl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, Aryl-$C_{3-8}$-heterocycloalk(en)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and halo-$C_{1-6}$-alk(en/yn)yl-$C_{3-8}$-heterocycloalk(en)yl-$C_{1-6}$-alk(en/yn)yl.

In one embodiment of the compound of formula XXVII any Aryl which is mentioned either alone or as a part of a larger substituent is optionally substituted with one or more substituents independently selected from the group consisting of amino, halogen, cyano, $C_{1-6}$-alk(en/yn)yl, halo-$C_{1-6}$-alk(en/yn)yl, hydroxy, $C_{1-6}$-alk(en/yn)yloxy, halo-$C_{1-6}$-alk(en/yn)yloxy, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which optionally contains one or two heteroatoms and which is optionally substituted with one or more $C_{1-6}$-alk(en/yn)yl groups.

In one embodiment of the compound of formula XXVII any Heteroaryl which is mentioned either alone or as a part of a larger substituent is optionally substituted with one or more substituents independently selected from the group consisting of halogen, halo-$C_{1-6}$-alk(en/yn)yl, $C_{1-6}$-alk(en/yn)yl, Aryl, $C_{1-6}$-alk(en/yn)yloxy and $C_{1-6}$-alk(en/yn)yl-phenoxy.

To further illustrate without limiting the invention, an embodiment of formula I relates to a compound having the general formula XXVIII or salts thereof:

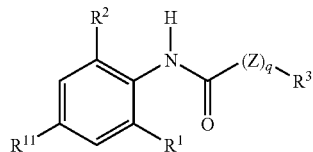

(XXVIII)

wherein Z, q, $R^1$, $R^2$ and $R^3$ are as defined above;

and $R^{11}$ is $R^7$NH—$C_{1-6}$-alk(en/yn)yl; wherein $R^7$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl and Heteroaryl.

In one embodiment of the compound of formula XXVIII $R^1$ and $R^2$ are independently selected from the group consisting of halogen, amino, $C_{1-6}$-alk(en/yn)yl, $C_{3-8}$-heterocycloalk(en)yl, Aryl, Heteroaryl and halo-$C_{1-6}$-alk(en/yn)yl.

In one embodiment of the compound of formula XXVIII q is 0.

In one embodiment of the compound of formula XXVIII q is 1.

In one embodiment of the compound of formula XXVIII Z is an oxygen atom.

In one embodiment of the compound of formula XXVIII $R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Heteroaryl-$C_{1-6}$-alk(en/yn)yl and amino-$C_{1-6}$-alk(en/yn)yl.

In one embodiment of the compound of formula XXVIII $R^7$ is Aryl.

In one embodiment of the compound of formula XXVIII any Aryl which is mentioned either alone or as a part of a larger substituent is optionally substituted with one or more substituents independently selected from the group consisting of amino, halogen, cyano, $C_{1-6}$-alk(en/yn)yl, halo-$C_{1-6}$-alk(en/yn)yl, hydroxy, $C_{1-6}$-alk(en/yn)yloxy, halo-$C_{1-6}$-alk(en/yn)yloxy, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which optionally contains one or two heteroatoms and which is optionally substituted with one or more $C_{1-6}$-alk(en/yn)yl groups.

In one embodiment of the compound of formula XXVIII any Heteroaryl which is mentioned either alone or as a part of a larger substituent is optionally substituted with one or more substituents independently selected from the group consisting of halogen, halo-$C_{1-6}$-alk(en/yn)yl, $C_{1-6}$-alk(en/yn)yl, Aryl, $C_{1-6}$-alk(en/yn)yloxy and $C_{1-6}$-alk(en/yn)yl-phenoxy.

In a further embodiment of the compound of formula I said compound is selected from the following list of compounds

| Example no. | Name |
|---|---|
| 1a | Hexanoic acid (4-bromo-2,6-dimethyl-phenyl)-amide |
| 1b | N-(4-Bromo-2,6-dimethyl-phenyl)-2-(4-fluoro-phenyl)-acetamide |
| 1c | N-(2-Bromo-4,6-dimethyl-phenyl)-2-(4-fluoro-phenyl)-acetamide |
| 1d | N-(2-Bromo-4,6-dimethyl-phenyl)-3,3-dimethyl-butyramide |
| 1e | N-(2-Bromo-4,6-dimethyl-phenyl)-2-cyclopentyl-acetamide |
| 1f | N-(2-Bromo-4,6-dichloro-phenyl)-3,3-dimethyl-butyramide |
| 1g | N-(2-Bromo-4,6-dichloro-phenyl)-2-(4-fluoro-phenyl)-acetamide |
| 1h | N-(2-Bromo-4,6-dichloro-phenyl)-2-cyclopentyl-acetamide |
| 1i | Heptanoic acid (4-bromo-2,6-dimethyl-phenyl)-amide |
| 1j | Cyclohexanecarboxylic acid (4-bromo-2,6-dimethyl-phenyl)-amide |
| 1k | N-(4-Bromo-2,6-dimethyl-phenyl)-2-thiophen-2-yl-acetamide |
| 1l | 2-Phenyl-cyclopropanecarboxylic acid (4-bromo-2,6-dimethyl-phenyl)-amide |
| 1m | N-(4-Bromo-2,6-dimethyl-phenyl)-2-(4-chloro-phenyl)-acetamide |
| 1n | Pentanoic acid (4-bromo-2,6-dimethyl-phenyl)-amide |
| 1o | Octanoic acid (4-bromo-2,6-dimethyl-phenyl)-amide |
| 1p | N-(4-Bromo-2,6-dimethyl-phenyl)-2-cyclopentyl-acetamide |
| 1q | 2-Bicyclo[2.2.1]hept-2-yl-N-(2,4-difluoro-6-morpholin-4-yl-phenyl)-acetamide |
| 1r | (S)-2-Amino-N-{2,6-dimethyl-4-[methyl-(4-trifluoromethyl-benzyl)-amino]-phenyl}-3-methyl-butyramide |
| 1s | (S)-2-Amino-4-methyl-pentanoic acid {2,6-dimethyl-4-[methyl-(4-trifluoromethyl-benzyl)-amino]-phenyl}-amide |
| 1t | (4-Bromo-2,6-dimethyl-phenyl)-carbamic acid ethyl ester |
| 1u | (4-Bromo-2,6-dimethyl-phenyl)-carbamic acid propyl ester |
| 1v | N-(2-Amino-4-bromo-6-methyl-phenyl)-3,3-dimethyl-butyramide |
| 1w | (R)-2-Amino-4-methylpentanoic acid [2,6-dimethyl-4-(4-trifluoromethylbenzylamino)-phenyl]-amide |
| 1x | [2-Amino-6-methyl-4-(4-trifluoromethylbenzylamino)-phenyl]-carbamic acid ethyl ester |
| 2a | 2-Cyclopentyl-N-{2,6-dimethyl-4-[2-(4-trifluoromethyl-phenyl)-pyrrolidin-1-yl]-phenyl}-acetamide |
| 2b | N-(4-Azepan-1-yl-2,6-dimethyl-phenyl)-2-cyclopentyl-acetamide |
| 2c | 2-Cyclopentyl-N-(2,6-dimethyl-4-pyrrol-1-yl-phenyl)-acetamide |
| 2d | 3,3-Dimethyl-N-[2-methyl-6-morpholin-4-yl-4-(4-trifluoromethylbenzylamino)-phenyl]-butyramide |
| 3a | N-(3'-Amino-3,5-dimethyl-biphenyl-2-yl)-2-(4-fluoro-phenyl)-acetamide |
| 3b | N-(4'-Dimethylamino-3,5-dimethyl-biphenyl-2-yl)-2-(4-fluoro-phenyl)-acetamide |
| 3c | N-(2,4-Dimethyl-6-quinolin-3-yl-phenyl)-2-(4-fluoro-phenyl)-acetamide |
| 3d | 2-(4-Fluoro-phenyl)-N-(4'-hydroxy-3'-methoxy-3,5-dimethyl-biphenyl-2-yl)-acetamide |
| 3e | 2-(4-Fluoro-phenyl)-N-(3'-hydroxy-3,5-dimethyl-biphenyl-2-yl)-acetamide |
| 3f | 2-(4-Fluoro-phenyl)-N-(2'-methanesulfonylamino-3,5-dimethyl-biphenyl-2-yl)-acetamide |
| 3g | N-(4'-Isopropyl-3,5-dimethyl-biphenyl-2-yl)-3,3-dimethyl-butyramide |
| 3h | 2-Cyclopentyl-N-(3,5-dimethyl-biphenyl-2-yl)-acetamide |
| 3i | N-(4'-Fluoro-3,5-dimethyl-biphenyl-2-yl)-2-(4-fluoro-phenyl)-acetamide |
| 3j | N-(3,5-Dimethyl-3',5'-bis-trifluoromethyl-biphenyl-2-yl)-2-(4-fluoro-phenyl)-acetamide |
| 3k | N-(3'-Acetylamino-3,5-dimethyl-biphenyl-2-yl)-2-(4-fluoro-phenyl)-acetamide |
| 3l | 2-(4-Fluoro-phenyl)-N-(2'-methoxy-3,5-dimethyl-biphenyl-2-yl)-acetamide |
| 3m | N-(3,5-Dimethyl-4'-vinyl-biphenyl-2-yl)-2-(4-fluoro-phenyl)-acetamide |
| 3n | N-(3'-Cyano-3,5-dimethyl-biphenyl-2-yl)-2-(4-fluoro-phenyl)-acetamide |
| 3o | N-(3,5-Dimethyl-3'-trifluoromethoxy-biphenyl-2-yl)-2-(4-fluoro-phenyl)-acetamide |
| 3p | N-[2-(2,3-Dihydro-benzo[1,4]dioxin-6-yl)-4,6-dimethyl-phenyl]-2-(4-fluoro-phenyl)-acetamide |
| 3q | N-[2,4-Dimethyl-6-(2,2,5-trimethyl-2,3-dihydro-benzofuran-7-yl)-phenyl]-2-(4-fluoro-phenyl)-acetamide |
| 4a | N-[2,6-Dimethyl-4-(4-trifluoromethyl-benzylamino)-phenyl]-acetamide |
| 4b | N-{2,6-Dimethyl-4-[methyl-(4-trifluoromethyl-benzyl)-amino]-phenyl}-acetamide |
| 4c | {4-[(5-Chloro-thiophen-2-ylmethyl)-amino]-2,6-dimethyl-phenyl}-carbamic acid propyl ester |
| 4d | [4-(4-Fluoro-benzylamino)-2,6-dimethyl-phenyl]-carbamic acid propyl ester |
| 4e | [2,6-Dimethyl-4-(4-trifluoromethyl-benzylamino)-phenyl]-carbamic acid propyl ester |
| 4f | [4-(3-Fluoro-4-trifluoromethyl-benzylamino)-2,6-dimethyl-phenyl]-carbamic acid propyl ester |
| 4g | {2,6-Dimethyl-4-[(4-methyl-2-phenyl-pyrimidin-5-ylmethyl)-amino]-phenyl}-carbamic acid propyl ester |
| 4h | {2,6-Dimethyl-4-[(6-p-tolyloxy-pyridin-3-ylmethyl)-amino]-phenyl}-carbamic acid propyl ester |
| 4i | {4-[(6-Methoxy-pyridin-3-ylmethyl)-amino]-2,6-dimethyl-phenyl}-carbamic acid propyl ester |
| 4j | {4-[(3-Fluoro-4-trifluoromethyl-benzyl)-methyl-amino]-2,6-dimethyl-phenyl}-carbamic acid propyl ester |
| 4k | 2-Cyclopentyl-N-[2,6-dimethyl-4-(4-trifluoromethyl-benzylamino)-phenyl]-acetamide |
| 4l | 2-Cyclopentyl-N-{2,6-dimethyl-4-[methyl-(4-trifluoromethyl-benzyl)-amino]-phenyl}-acetamide |
| 4m | 2-Cyclopentyl-N-{2,6-dimethyl-4-[(6-trifluoromethyl-pyridin-3-ylmethyl)-amino]-phenyl}-acetamide |
| 4n | N-{2,6-Dimethyl-4-[(6-trifluoromethyl-pyridin-3-ylmethyl)-amino]-phenyl}-3,3-dimethyl-butyramide |
| 4o | N-{2-Bromo-4-[(5-chloro-thiophen-2-ylmethyl)-amino]-6-trifluoromethyl-phenyl}-3-cyclohexyl-propionamide |
| 4p | N-{2-Chloro-6-methyl-4-[(6-trifluoromethyl-pyridin-3-ylmethyl)-amino]-phenyl}-2-(3-fluoro-phenyl)-acetamide |
| 4q | N-[2-Chloro-6-trifluoromethyl-4-(4-trifluoromethylbenzyl-amino)-phenyl]-2-cyclopentylacetamide |
| 5a | {4-[(3-Fluoro-phenylamino)-methyl]-2,6-dimethyl-phenyl}-carbamic acid ethyl ester |
| 5b | {2,6-Dimethyl-4-[(4-trifluoromethyl-phenylamino)-methyl]-phenyl}-carbamic acid ethyl ester |
| 5c | 2-Cyclopentyl-N-{4-[(3-fluoro-phenylamino)-methyl]-2,6-dimethyl-phenyl}-acetamide |
| 5d | N-{4-[(3-Chloro-phenylamino)-methyl]-2,6-dimethyl-phenyl}-2-cyclopentyl-acetamide |
| 5e | 2-Cyclopentyl-N-{4-[(3-methoxy-phenylamino)-methyl]-2,6-dimethyl-phenyl}-acetamide |
| 5f | N-{4-[(4-Chloro-phenylamino)-methyl]-2,6-dimethyl-phenyl}-2-cyclopentyl-acetamide |
| 5g | 2-Cyclopentyl-N-{4-[(3,4-difluoro-phenylamino)-methyl]-2,6-dimethyl-phenyl}-acetamide |
| 5h | 2-Cyclopentyl-N-{2,6-dimethyl-4-[(4-trifluoromethyl-phenyl-amino)-methyl]-phenyl}-acetamide |
| 5i | 2-Cyclopentyl-N-[2,6-dimethyl-4-(p-tolylamino-methyl)-phenyl]-acetamide |
| 5j | 2-Cyclopentyl-N-{2,6-dimethyl-4-[(3-trifluoromethyl-phenyl-amino)-methyl]-phenyl}-acetamide |
| 5k | 2-Cyclopentyl-N-{4-[(3,5-difluoro-phenylamino)-methyl]-2,6-dimethyl-phenyl}-acetamide |
| 5l | {4-[(4-Fluoro-phenylamino)-methyl]-2,6-dimethyl-phenyl}-carbamic acid propyl ester |
| 5m | {4-[(4-Chloro-phenylamino)-methyl]-2,6-dimethyl-phenyl}-carbamic acid propyl ester |
| 5n | {2,6-Dimethyl-4-[(4-trifluoromethyl-phenylamino)-methyl]-phenyl}-carbamic acid propyl ester |
| 5o | {4-[(3,5-Difluoro-phenylamino)-methyl]-2,6-dimethyl-phenyl}-carbamic acid propyl ester |
| 5p | {4-[(3-Fluoro-phenylamino)-methyl]-2,6-dimethyl-phenyl}-carbamic acid propyl ester |
| 5q | {4-[(4-Methoxyphenylamino)-methyl]-2,6-dimethylphenyl}-carbamic acid propyl ester |
| 5r | Pentanoic acid {4-[(4-chlorophenylamino)-methyl]-2,6-dimethylphenyl}-amide |

-continued

| Example no. | Name |
|---|---|
| 5s | 2-(4-Chlorophenyl)-N-{4-[(4-chlorophenylamino)-methyl]-2,6-dimethylphenyl}-acetamide |
| 5t | {2,6-Dimethyl-4-[(4-trifluoromethylphenylamino)-methyl]-phenyl}-carbamic acid 2-methoxyethyl ester |
| 5u | N-{4-[(5-Chloro-pyridin-2-ylamino)-methyl]-2,6-dimethyl-phenyl}-2-cyclopentylacetamide |
| 5v | 2-Cyclopentyl-N-{4-[(2,6-dichloro-pyridin-4-ylamino)-methyl]-2,6-dimethylphenyl}-acetamide |
| 5w | 2-Cyclopentyl-N-{2,6-dichloro-4-[(4-fluoro-phenylamino)-methyl]-phenyl}-acetamide |
| 5x | 2-Cyclopentyl-N-{2,6-dichloro-4-[(5-trifluoromethylpyridin-2-ylamino)-methyl]-phenyl}-acetamide |
| 6a | N-(4-Bromo-2-methyl-6-morpholin-4-yl-phenyl)-3,3-dimethyl-butyramide | or a salt thereof. Each of these compounds is considered a specific embodiment and may be subjected to individual claims.

The present invention also comprises salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Also intended as acid addition salts are the hydrates, which the present compounds, are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomers, are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the invention have affinity for the KCNQ2 receptor subtype with an $EC_{50}$ of less than 15000 nM such as less than 10000 nM as measured by the test "Relative efflux through the KCNQ2 channel" which is described below. One embodiment concerns such compounds of formula I having affinity for the KCNQ2 receptor subtype with an $EC_{50}$ of less than 2000 nM such as less than 1500 nM as measured by the test "Relative efflux through the KCNQ2 channel" which is described below. To further illustrate without limiting the invention an embodiment concerns such compounds having affinity for the KCNQ2 receptor subtype with an $EC_{50}$ of less than 200 nM such as less than 150 nM as measured by the test "Relative efflux through the KCNQ2 channel" which is described below.

One embodiment concerns such compounds of formula I having an $ED_{50}$ of less than 15 mg/kg in the test "Maximum electroshock" which is described below. To further illustrate without limiting the invention an embodiment concerns such compounds having an $ED_{50}$ of less than 5 mg/kg in the test "Maximum electroshock" which is described below.

One embodiment concerns such compounds of formula I having an $ED_{50}$ of less than 5 mg/kg in the "Electrical seizure-threshold test" and "Chemical seizure-threshold test" which is described below.

One embodiment concerns such compounds of formula I having few or clinically insignificant side effects. Some of the compounds according to the invention are thus tested in models of the unwanted sedative, hypothermic and ataxic actions.

One embodiment concerns such compounds of formula I having a large therapeutic index between anticonvulsant efficacy and side-effects such as impairment of locomotor activity or ataxic effects as measured by performance on a rotating rod. Such compounds will expectedly be well tolerated in patients permitting high doses to be used before side effects are seen. Thereby compliance with the therapy will expectedly be good and administration of high doses may be permitted making the treatment more efficacious in patients who would otherwise have side effects with other medications.

As already mentioned, the compounds according to the invention have effect on potassium channels of the KCNQ family, in particular the KCNQ2 subunit, and they are thus considered useful for increasing ion flow in a voltage-dependent potassium channel in a mammal such as a human. The compounds of the invention are considered applicable in the treatment of a disorder or disease being responsive to an increased ion flow in a potassium channel such as the KCNQ family potassium ion channels. Such disorder or disease is preferably a disorder or disease of the central nervous system.

In one aspect, the compounds of the invention may be administered as the only therapeutically effective compound.

In another aspect the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include but not be limited to activities on:

- ion channels such as sodium, potassium, or calcium channels
- the excitatory amino acid systems e.g. blockade or modulation of NMDA receptors
- the inhibitory neurotransmitter systems e.g. enhancement of GABA release, or blockade of GABA-uptake or
- membrane stabilisation effects.

Current anti-convulsive medications include, but are not limited to, tiagabine, carbamazepine, sodium valproate, lamotrigine, gabapentin, pregabalin, ethosuximide, levetiracetam, phenyloin, topiramate, zonisamide as well as members of the benzodiazepine and barbiturate class.

An aspect of the invention provides a compound of formula I or a salt thereof for use as a medicament.

In one embodiment, the invention relates to the use of a compound of formula I or a salt thereof in a method of treatment.

An embodiment of the invention provides a pharmaceutical composition comprising a compound of formula I or a salt thereof and one or more pharmaceutically acceptable carrier or diluent. The composition may comprise any of the embodiments of formula I as described above.

A further embodiment of the invention relates to the use of a compound of formula I or a salt thereof for the preparation of a pharmaceutical composition for the treatment of a disease or disorder wherein a KCNQ potassium channel opener such as a KCNQ2 potassium channel opener is beneficial. Typically, such disorder or disease is selected from the group consisting of seizure disorders, anxiety disorders, neuropathic pain and migraine pain disorders or neurodegenerative disorders.

A further embodiment of the invention relates to the use of a compound of formula I or a salt thereof for the preparation of a pharmaceutical composition for the treatment of seizure disorders.

Typically, the seizure disorders to be treated are selected from the group consisting of acute seizures, convulsions, status epilepticus and epilepsy such as epileptic syndromes and epileptic seizures.

A further embodiment of the invention relates to the use of a compound of formula I or a salt thereof for the preparation of a pharmaceutical composition for the treatment of anxiety disorders.

Typically, the anxiety disorders to be treated are selected from the group consisting of anxiety and disorders and diseases related to panic attack, agoraphobia, panic disorder with agoraphobia, panic disorder without agoraphobia, agoraphobia without history of panic disorder, specific phobia, social phobia and other specific phobias, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders, performance anxiety, hypochondriacal disorders, anxiety disorder due to general medical condition and substance-induced anxiety disorder and anxiety disorder not otherwise specified.

A further embodiment of the invention relates to the use of a compound of formula I or a salt thereof for the preparation of a pharmaceutical composition for the treatment of neuropathic pain and migraine pain disorders.

Typically, the neuropathic pain and migraine pain disorders to be treated are selected from the group consisting of allodynia, hyperalgesic pain, phantom pain, neuropathic pain related to diabetic neuropathy, neuropathic pain related to trigeminal neuralgia and neuropathic pain related to migraine.

A further embodiment of the invention relates to the use of a compound of formula I or a salt thereof for the preparation of a pharmaceutical composition for the treatment of neurodegenerative disorders.

Typically the neurodegenerative disorders to be treated are selected from the group consisting of Alzheimer's disease, Huntington's chorea, multiple sclerosis, amyotrophic lateral sclerosis, Creutzfeld-Jakob disease, Parkinson's disease, encephalopathies induced by AIDS or infection by rubella viruses, herpes viruses, borrelia and unknown pathogens, trauma-induced neurodegenerations, neuronal hyperexcitation states such as in medicament withdrawal or intoxication and neurodegenerative diseases of the peripheral nervous system such as polyneuropathies and polyneuritides.

A further embodiment of the invention relates to the use of a compound of formula I or a salt thereof for the preparation of a pharmaceutical composition for the treatment of stroke, cocaine abuse, nicotine withdrawal, ethanol withdrawal or tinnitus.

The term "treatment" as used herein in connection with a disease or disorders includes also prevention, inhibition and amelioration as the case may be.

The invention provides compounds showing effect in one or more of the following tests:

"Relative efflux through the KCNQ2 channel"
Which is a measure of the potency of the compound at the target channel
"Maximum electroshock"
Which is a measure of seizures induced by non-specific CNS stimulation by electrical means "Pilocarpine induced seizures"
Seizures induced by pilocarpine are often difficult to treat with many existing antiseizure medications and so reflect a model of "drug resistant seizures"

"Electrical seizure-threshold tests" and "Chemical seizure-threshold tests"
These models measure the threshold at which seizures are initiated, thus being models that detect whether compounds could delay seizure initiation.

"Amygdala kindling"
Which is used as a measure of disease progression, as in normal animals the seizures in this model get more severe as the animal receives further stimulations.

Pharmaceutical Compositions

The present invention also relates to a pharmaceutical composition. The compounds of the invention or salts thereof may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa. 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the disorder or disease to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the disorder or disease treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | | |
|---|---|---|
| | Compound of the invention | 5.0 mg |
| | Lactose | 60 mg |
| | Maize starch | 30 mg |
| | Hydroxypropylcellulose | 2.4 mg |
| | Microcrystalline cellulose | 19.2 mg |
| | Croscarmellose Sodium Type A | 2.4 mg |
| | Magnesium stearate | 0.84 mg |

2) Tablets containing 0.5 mg of a compound of the invention calculated as the free base:

| | | |
|---|---|---|
| | Compound of the invention | 0.5 mg |
| | Lactose | 46.9 mg |
| | Maize starch | 23.5 mg |
| | Povidone | 1.8 mg |
| | Microcrystalline cellulose | 14.4 mg |
| | Croscarmellose Sodium Type A | 1.8 mg |
| | Magnesium stearate | 0.63 mg |

3) Syrup containing per milliliter :

| | | |
|---|---|---|
| | Compound of the invention | 25 mg |
| | Sorbitol | 500 mg |
| | Hydroxypropylcellulose | 15 mg |
| | Glycerol | 50 mg |
| | Methyl-paraben | 1 mg |
| | Propyl-paraben | 0.1 mg |
| | Ethanol | 0.005 mL |
| | Flavour | 0.05 mg |
| | Saccharin sodium | 0.5 mg |
| | Water | ad 1 mL |

4) Solution for injection containing per milliliter :

| | | |
|---|---|---|
| | Compound of the invention | 0.5 mg |
| | Sorbitol | 5.1 mg |
| | Acetic Acid | 0.05 mg |
| | Saccharin sodium | 0.5 mg |
| | Water | ad 1 mL |

By the expression a compound of the invention is meant any one of the embodiments of formula I as described herein.

In a further aspect the present invention relates to a method of preparing a compound of the invention as described in the following.

METHODS OF PREPARATION OF THE COMPOUNDS OF THE INVENTION

The compounds of the invention of the general formula I, wherein q, Z, $R^1$, $R^2$, $R^3$, $R^4$, $R^5$, $R^6$ and $R^7$ are as defined above may be prepared by the methods as represented in the schemes and as described below.

In the compounds of the general formulae I-XXV, q, Z, $R^1$, $R^2$, $R^3$, $R^4$, $R^5$, $R^6$ and $R^7$ are as defined under formula I.

Compounds of the general formulae II, III, V, VII, XV, XXI, XXII, XXIII, XXIV and XXV are either obtained from commercial sources, or prepared by standard methods known to chemists skilled in the art.

General Methods

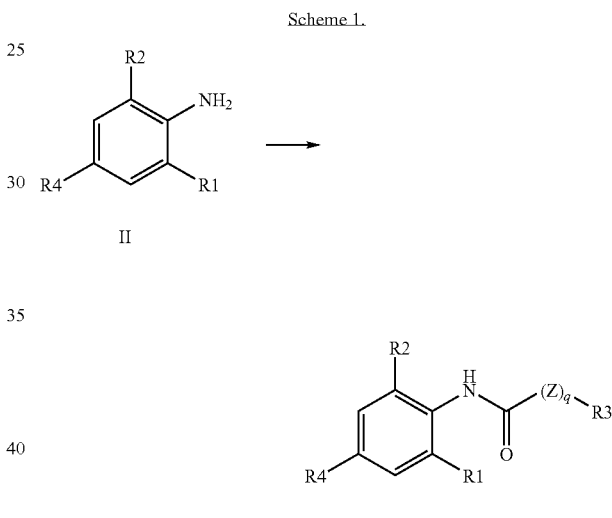

Compounds of the general formula I (scheme 1) may be prepared by reacting compounds of the general formula II with suitable electrophilic reagents, such as, but not limited to, suitably substituted carboxylic acid fluorides, carboxylic acid chlorides, carboxylic acid bromides, carboxylic acid iodides, carboxylic acid anhydrides, activated esters, chloro formates, chloro thioformates, and with or without the addition of bases, such as pyridine, trialkyl amines, potassium carbonate, sodium hydrogen carbonate, magnesium oxide or lithium-, sodium-, or potassium alcoholates, in a suitable solvent, such as ethyl acetate, dioxane, tetrahydrofuran, acetonitrile or diethyl ether, at suitable temperatures, such as room temperature or reflux temperature. Activated esters and carboxylic acid anhydrides can be prepared from suitably substituted carboxylic acids under conditions known to chemists skilled in the art, as described by F. Albericio and L. A. Carpino, "Coupling reagents and activation" in *Methods in enzymology: Solid-phase peptide synthesis*, pp. 104-126, Academic Press, New York, 1997. Carboxylic acid halides can be prepared from suitably substituted carboxylic acids by activation with reagents such as, but not limited to, thionyl chloride, oxalyl chloride, phosphorus tribromide or phosphorus triiodide under conditions well known to chemists skilled in the art.

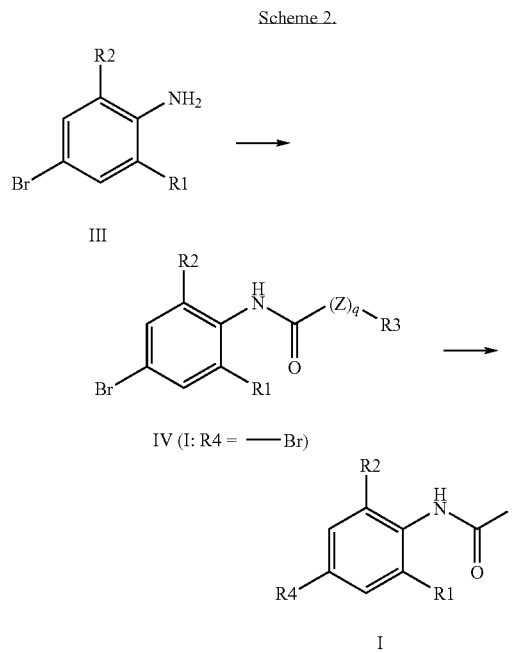

Compounds of the general formula IV (scheme 2) may be prepared by reacting compounds of the general formula III with suitable electrophilic reagents as described under scheme 1 for the preparation of compounds of the general formula I.

Compounds of the general formula I, wherein $R^4$ is $C_{3-8}$-heterocycloalk(en)yl, Ar—$C_{3-8}$-heterocycloalk(en)yl, Het or $NR^5R^6$ (scheme 2), may be prepared by reacting compounds of the general formula IV with suitably substituted nitrogen-containing compounds in the presence of a palladium or copper catalyst, such as bis(dibenzylideneacetone)palladium or copper(II) trifluoromethanesulfonate with the addition of a suitable ligand, such as (2'-dicyclohexylphosphanyl-biphenyl-2-yl)-dimethyl-amine or 1,10-phenanthroline in the presence of a base, such as potassium carbonate or lithium-, sodium-, or potassium alcoholates, in a suitable solvent, such as toluene or tetrahydrofuran, at suitable temperatures, such as room temperature or reflux temperature as described by S. L. Buchwald et al. (M. C. Harris, X. Hang and S. L. Buchwald, *Org. Lett.*, 2002, 4, 2885 and A. Kiyomori, J. F. Marcoux and S. L. Buchwald, *Tet. Lett.*, 1999, 40, 2657).

Additionally, compounds of the general formula I, wherein $R^4$ is Ar or Het (scheme 2), can be prepared from compounds of the general formula IV, by means of cross-coupling reactions known to chemists skilled in the art, such as Suzuki coupling, Stille coupling, or other transition metal catalyzed cross-coupling reactions (D. W. Knight, "Coupling reactions between sp2 carbon centers" in *Comprehensive Organic Synthesis*, v. 3, pp. 481-520, Pergamon Press, 1991).

Additionally, compounds of the general formula I, wherein $R^4$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Ar—$C_{1-6}$-alk(en/yn)yl, Ar—$C_{3-8}$-cycloalk(en)yl or Ar—$C_{3-8}$-cycloalk(en)yl-$C_{1-6}$-alk(en/yn)yl (scheme 2), may be prepared from compounds of the general formula IV, by means of cross-coupling reactions known to chemists skilled in the art, such as Negishi coupling (E.-I. Negishi, A. O. King and N. Okukado, *J. Org. Chem.*, 1977, 42, 1821), Sonogashira coupling (K. Sonogashira, Y. Tohda and N. Hagihara, *Tet. Lett.*, 1975, 16, 4467), or other transition metal catalyzed cross-coupling reactions such as copper catalyzed reactions (W. Dohle, D. M. Lindsay and P. Knochel, *Org. Lett.*, 2001, 3, 2871).

Additionally, compounds of the general formula I, wherein $R^4$ is cyano (scheme 2), may be prepared from compounds of the general formula IV, by means of nickel-catalyzed cyanation reactions known to chemists skilled in the art as described by L. Cassar, *J. Organomet. Chem.*, 1973, 54, C57-C58.

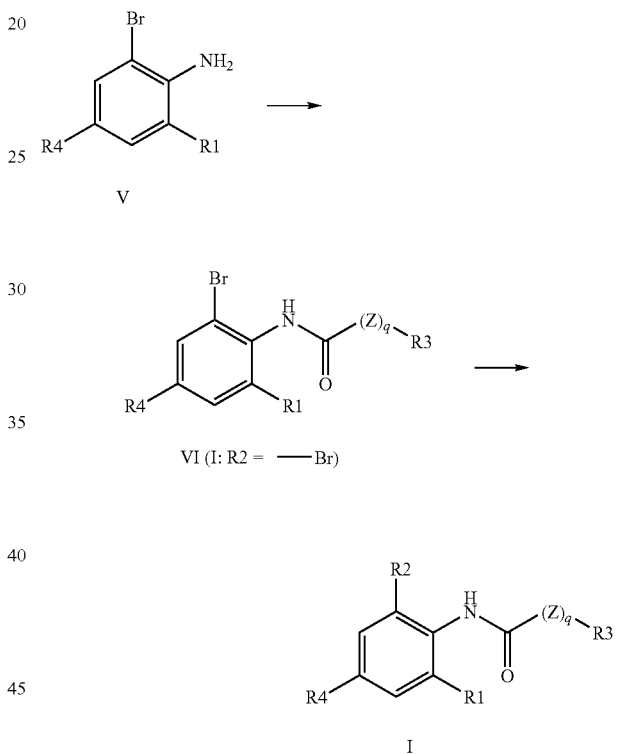

Compounds of the general formula VI (scheme 3) may be prepared by reacting compounds of the general formula V with suitable electrophilic reagents as described under scheme 1 for the preparation of compounds of the general formula I.

Compounds of the general formula I (scheme 3) may be prepared from compounds of the general formula VI, by means of cross-coupling reactions or cyanation reactions as described under scheme 2 for the preparation of compounds of the general formula I.

Compounds of the general formula I, wherein $R^1$=$R^2$ (scheme 3), may be prepared from compounds of the general formula VI, wherein $R^1$=$R^2$=Br, by means of cross-coupling reactions or cyanation reactions as described under scheme 2 for the preparation of compounds of the general formula I.

Scheme 4.

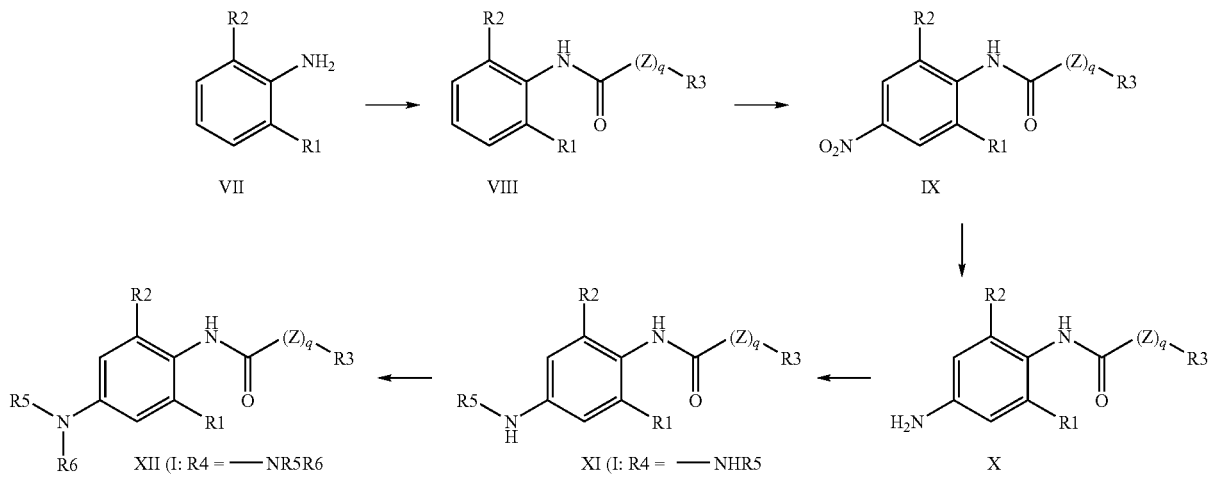

Compounds of the general formula VIII (scheme 4) may be prepared by reacting compounds of the general formula VII with suitable electrophilic reagents as described under scheme 1 for the preparation of compounds of the general formula I.

Compounds of the general formula IX (scheme 4) may be prepared from compounds of the general formula VIII by nitration reactions known to chemists skilled in the art, such as reaction with concentrated nitric acid or sodium nitrite, in a suitable solvent, such as glacial acetic acid, acetic anhydride, trifluoroacetic acid or mixtures thereof, at appropriate temperatures, as described by P. B. D. de la Mare and J. H. Ridd, "Preparative methods of nitration" in *Aromatic substitutions*, pp. 48-56, Butterworths Scientific Publications, London, 1959.

Compounds of the general formula X (scheme 4) may be prepared from compounds of the general formula IX, by reducing the nitro group to an amino group, with suitable reducing agents such as zinc or iron powder in the presence of acid such as acetic acid or aqueous hydrochloric acid, or by hydrogen gas or ammonium formiate in the presence of a suitable hydrogenation catalyst such as palladium on activated carbon in suitable solvents such as methanol, ethanol or tetrahydrofuran, at suitable temperatures or under ultrasonic irradiation. Alternatively, tin (II) chloride or sodium dithionite can be used as reducing agents under conditions well known to chemists skilled in the art.

Compounds of the general formula XI (scheme 4) may be prepared from compounds of the general formula X, by means of reductive alkylation reactions, known to chemists skilled in the art, with suitably substituted aldehydes or ketones using reducing agents, such as sodium borohydride, sodium cyanoborohydride or hydrogen gas in the presence of a suitable hydrogenation catalyst such as palladium on activated carbon in a suitable solvent, such as methanol, ethanol, THF, water, dioxane or mixtures thereof, with or without addition of catalytic amounts of acid, such as acetic acid, at suitable temperatures.

Alternatively, compounds of the general formula X (scheme 4) may be reacted with suitably substituted aldehydes or ketones in a suitable solvent, such as methanol, ethanol, THF, dioxane, xylene, or mixtures thereof, with or without addition of catalytic amounts of acid, such as acetic acid or acidic ion exchange resin, at suitable temperatures, to form imines, that can be isolated by crystallisation or by evaporation of the solvent. The imines can then be reduced using reducing reagents as described above, to form compounds of the general formula XI.

Compounds of the general formula XII (scheme 4) may be prepared from compounds of the general formula XI, by means of reductive alkylation reactions or imine formation followed by reduction as described above.

Alternatively, compounds of the general formula XII (scheme 4) may be prepared from compounds of the general formula X, by means of reductive alkylation reactions with a suitably substituted aldehyde or ketone (to introduce $R^5$) followed by addition of another suitably substituted aldehyde or ketone (to introduce $R^6$) in the presence of excess reducing agent.

Scheme 5.

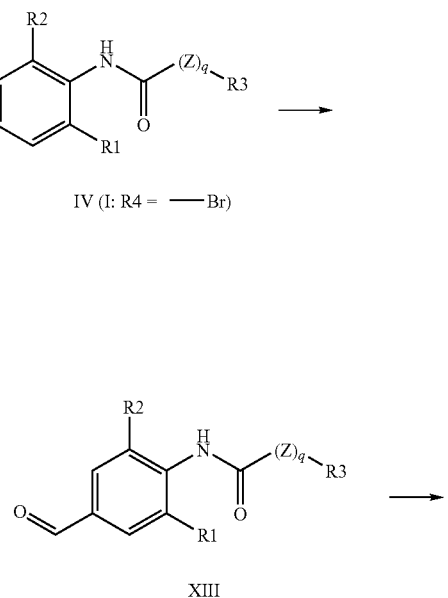

-continued

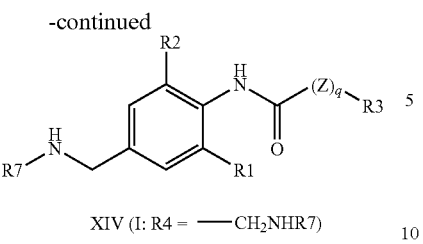

XIV (I: R4 = —CH₂NHR7)

Compounds of the general formula XIII (scheme 5) may be prepared by reacting compounds of the general formula IV with a suitable base such as isopropylmagnesium chloride or methyl lithium followed by addition of an alkyl or aryl lithium derivative, such as tert-butyllithium and quenching with a suitable electrophile, such as N,N-dimethylformamide at suitable temperatures as described by L. E. Overman and S. E. Angle, *J. Org. Chem.*, 1985, 50, 4021.

Compounds of the general formula XIV (scheme 5) may be prepared from compounds of the general formula XIII, by means of reductive alkylation reactions, known to chemists skilled in the art, with suitably substituted amines using reducing agents, such as sodium borohydride, sodium cyanoborohydride or hydrogen gas in the presence of a suitable hydrogenation catalyst such as palladium on activated carbon in a suitable solvent, such as methanol, ethanol, THF, water, dioxane or mixtures thereof, with or without addition of catalytic amounts of acid, such as acetic acid, at suitable temperatures.

Alternatively, compounds of the general formula XIII (scheme 5) may be reacted with suitably substituted amines in a suitable solvent, such as methanol, ethanol, THF, dioxane, xylene, or mixtures thereof, with or without addition of catalytic amounts of acid, such as acetic acid or acidic ion exchange resin, at suitable temperatures, to form imines, that can be isolated by crystallisation or by evaporation of the solvent. The imines can then be reduced using reducing reagents as described above, to form compounds of the general formula XIV.

-continued

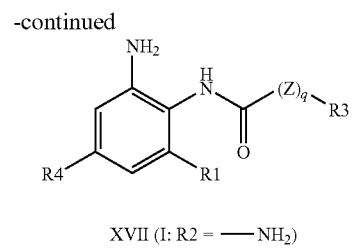

XVII (I: R2 = —NH₂)

↓

R2, R4, R1, (Z)q, R3

I

Compounds of the general formula XVI (scheme 6) may be prepared by reacting compounds of the general formula XV with suitable electrophilic reagents as described under scheme 1 for the preparation of compounds of the general formula I.

Compounds of the general formula XVII (scheme 6) may be prepared from compounds of the general formula XVI, by reducing the nitro group as described under scheme 4 for the preparation of compounds of the general formula X.

Compounds of the general formula I, wherein R² is 4-morpholinyl (scheme 6), may be prepared by reacting compounds of the general formula XVII with suitably substituted bis-(2-haloethyl)ethers and with or without the addition of bases, such as trialkyl amines, potassium carbonate or lithium-, sodium-, or potassium alcoholates, in a suitable solvent, such as dimethyl sulfoxide or N,N-dimethylformamide, at suitable temperatures, such as reflux temperature.

Scheme 6.

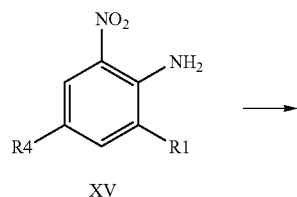

XV

Scheme 7.

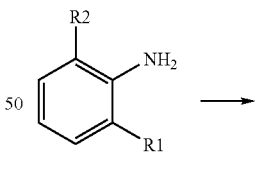

VII

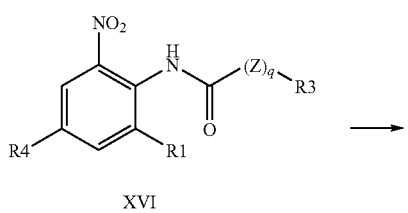

XVI

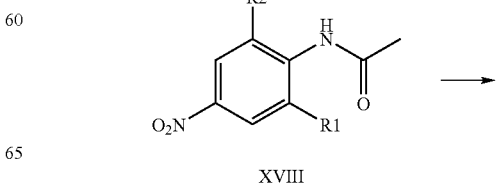

XVIII

-continued

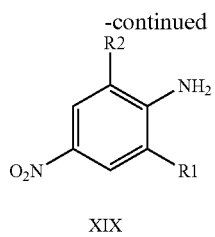

XIX

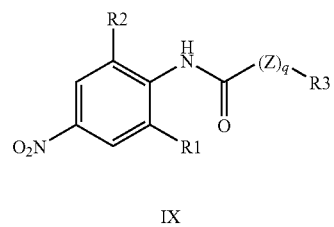

IX

Compounds of the general formula XVIII (scheme 7) may be prepared from compounds of the general formula VII, by means of nitration in acetic anhydride as described under scheme 4 for the preparation of compounds of the general formula IX.

Compounds of the general formula XIX (scheme 7) may be prepared from compounds of the general formula XVIII, by means of amide hydrolysis with a suitable strong acid, such as concentrated hydrochloric acid at suitable temperatures, such as room temperature or reflux temperature.

Compounds of the general formula IX (scheme 7) may be prepared by reacting compounds of the general formula XIX with suitable electrophilic reagents as described under scheme 1 for the preparation of compounds of the general formula I.

Scheme 8.

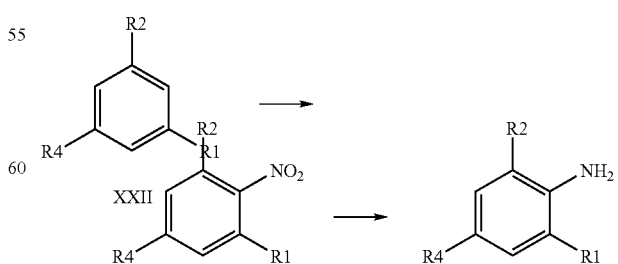

XX (I: q = 0, R3 = —CH₃)

-continued

II

Compounds of the general formula H (scheme 8) may be prepared from compounds of the general formula XX, by means of amide hydrolysis with a suitable strong acid as described under scheme 7 for the preparation of compounds of the general formula XIX.

Scheme 9.

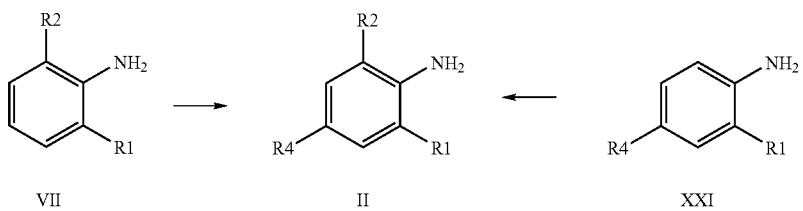

VII     II     XXI

Compounds of the general formula II, wherein $R^4$ is Cl, Br or I (scheme 9), may be prepared from compounds of the general formula VII, by means of electrophilic aromatic substitution well known to chemists skilled in the art, with appropriate electrophiles such as N-chlorosuccinimide, N-bromosuccinimide, N-iodosuccinimide, chlorine, bromine, iodine or iodochloride in a suitable solvent such as acetic acid, as described by P. B. D. de la Mare and J. H. Ridd, "Preparative methods of aromatic halogenation" in *Aromatic substitutions*, pp. 105-115, Butterworths Scientific Publications, London, 1959.

Alternatively, compounds of the general formula II, wherein $R^2$ is Cl, Br or I (scheme 9) may be prepared from compounds of the general formula XXI, by means of electrophilic aromatic substitution as described above.

Scheme 10.

Compounds of the general formula XXIII (scheme 10) may be prepared from compounds of the general formula XXII, by means of nitration reactions as described under scheme 4 for the preparation of compounds of the general formula IX.

Compounds of the general formula II (scheme 10) may be prepared from compounds of the general formula XXIII, by reducing the nitro group as described under scheme 4 for the preparation of compounds of the general formula X.

Scheme 11.

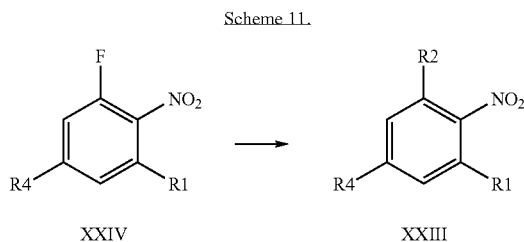

Compounds of the general formula XXIII, wherein $R^2$ is $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy or $C_{3-8}$-heterocycloalk(en)yl (scheme 11), may be prepared from compounds of the general formula XXIV, by means of nucleophilic aromatic substitution, with a suitable nucleophile such as alcohols, phenols, amines or anilines in their neutral or deprotonated form, and with or without the addition of bases, such as pyridine, trialkyl amines, potassium carbonate, magnesium oxide or lithium-, sodium-, or potassium alcoholates, in a suitable solvent, such as dimethyl sulfoxide or N,N-dimethylformamide, at suitable temperatures, such as room temperature or reflux temperature.

Scheme 12.

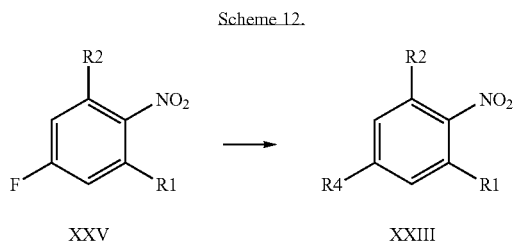

Compounds of the general formula XXIII, wherein $R^4$ is $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, $C_{3-8}$-heterocycloalk(en)yloxy or $C_{3-8}$-heterocycloalk(en)yl (scheme 12), may be prepared from compounds of the general formula XXV, by means of nucleophilic aromatic substitution as described under scheme 11 for the preparation of compounds of the general formula XXIII.

Additionally, for further variation of $R^1$, $R^2$, Ar and Het-groups, compounds containing a methoxy-group, can be demethylated by methods known to chemists skilled in the art, such as treatment with boron tribromide in a suitable solvent, such as dichloromethane, at suitable temperatures, such as 0° C. or room temperature. The resulting phenols can then be alkylated or arylated by methods known to chemists skilled in the art. Such methods include: (a) the reaction with electrophiles, such as alkyl chlorides, alkyl bromides, alkyl iodides, benzyl chlorides, benzyl bromides, benzyl iodides, carbonic acid chlorides, carbonic acid bromides; or carbonic acid anhydrides in the presence of suitable bases, such as potassium carbonate, in a suitable solvent, such as tetrahydrofuran, N,N-dimethylformamide, or 1,2-dichloroethane, at suitable temperatures, such as room temperature or reflux temperature; (b) the reaction with alkyl, benzylic, or heteroarylalkyl alcohols under conditions known as the Mitsunobu reaction (O. Mitsunobu, *Synthesis* 1981, 1).

Compounds containing functional groups, such as hydroxy and amino groups, not compatible with suggested reaction conditions, can be protected and deprotected by methods known to chemists skilled in the art, as described by T. W. Greene and P. G. M. Wuts, *Protective groups in organic synthesis*, $2^{nd}$ edition, Wiley Interscience, 1991. In particular, amino groups can be protected by groups such as, but not limited to, tert-butoxycarbonyl, trifluoroacetyl, fluorenylmethyloxycarbonyl or masked as a nitro group, and hydroxy groups can be protected as, but not limited to, methyl-, tert-butyl-, trialkylsilyl-, triarylsilyl-, allyl- or trityl ethers.

Alkynes prepared by Sonogashira reactions may be reduced to alkenes or alkanes by reduction with hydrogen gas or ammonium formiate in the presence of a suitable hydrogenation catalyst such as palladium on activated carbon or platinum on activated carbon in suitable solvents such as methanol, ethanol or tetrahydrofuran, at suitable temperatures as described by S. Siegel, "Heterogeneous catalytic hydrogenation of C=C and alkynes" in *Comprehensive Organic Synthesis*, v. 8, pp. 417-442, Pergamon Press, 1991.

Suitably substituted aryl halides can be converted to boronic acids or boronic esters by methods known to chemists skilled in the art as described by W. Gerrard, *The chemistry of boron*, Academic Press, New York, 1961 and T. Ishiyama, M. Murata, N. Miyaura, *J. Org. Chem.*, 1995, 60, 7508.

Suitably substituted carboxylic acids can be converted to aldehydes by methods known to chemists skilled in the art as described by R. A. W. Johnstone, "Reduction of carboxylic acids to aldehydes by metal hydrides" in *Comprehensive Organic Synthesis*, v. 8, pp. 259-281, Pergamon Press, 1991.

Suitably substituted carboxylic acids can be converted to alcohols by methods known to chemists skilled in the art as described by A. G. M. Barrett, "Reduction of carboxylic acid derivatives to alcohols, ethers and amines" in *Comprehensive Organic Synthesis*, v. 8, pp. 235-257, Pergamon Press, 1991.

Suitably substituted alcohols can be converted to aldehydes by methods known to chemists skilled in the art as described by T. V. Lee, "Oxidation adjacent to oxygen of alcohols by activated DMSO methods" in *Comprehensive Organic Synthesis*, v. 7, pp. 291-303, Pergamon Press, 1991.

Preperation of Intermediates

Analytical LC-MS data were obtained on a PE Sciex API 150EX instrument equipped with athmospheric pressure photo ionisation and a Shimadzu LC-8A/SLC-10A LC system. Column: 30×4.6 mm Waters Symmetry C18 column with 3.5 µm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with athmospheric pressure chemical ionisation. Column: 50×20 mm YMC ODS-A with 5 µm particle size; Method: Linear gradient elution with 80% A to 100% B in 7 minutes and with a flow rate of 22.7 mL/minute. Fraction collection was performed by split-flow MS detection.

Analytical LC-MS-TOF (TOF=time of flight) data were obtained on a micromass LCT 4-ways MUX equipped with a Waters 2488/Sedex 754 detector system. Column: 30×4.6 mm Waters Symmetry C18 column with 3.5 µm particle size;

Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

GC-MS data were obtained on a Varian CP 3800 gaschromatograph fitted with a Phenomenex column (Zebron ZB-5, length: 15 meter s, internal diameter: 0.25 mm) coupled to a Varian Saturn 2000 iontrap mass spectrometer. Method: Duration 15 minutes, column flow 1.4 mL/minute (carrier gas was helium), oven gradient: 0-1 minute, 60° C.; 1-13 minutes, 60-300° C.; 13-15 minutes, 300° C.

$^1$H NMR spectra were recorded at 500.13 MHz on a Bruker Avance DRX500 instrument. Deuterated chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and b=broad singlet.

Preparation of Intermediates (4-Formyl-2,6-dimethyl-phenyl)-carbamic acid ethyl ester To (4-bromo-2,6-dimethyl-phenyl)-carbamic acid ethyl ester (1t, 1.0 g) dissolved in dry tetrahydrofuran (25 mL) under argon was added isopropylmagnesium chloride (2 M in tetrahydrofuran, 1.9 mL) over 5 minutes and then stirred for 30 minutes. The reaction mixture was cooled to −78° C. and tert-butyllithium (1.7 M in heptane, 4.5 mL) was added dropwise while keeping the internal temperature below −65° C. The temperature of the reaction was raised to −10° C. after complete addition, and then cooled to −78° C. again followed by addition of N,N-dimethylformamide (0.6 mL). The reaction was stirred for 30 minutes at −78° C., 30 minutes at 25° C. and then poured onto crushed ice mixed with acetic acid (25 mL). The mixture was stirred for 30 minutes, extracted with ethyl acetate (3×100 mL), dried over magnesium sulfate, and concentrated in vacuo. The crude product was subjected to flash chromatography to furnish 0.60 g (73% yield) of the title compound as a white solid. LC-MS (m/z) 222 (MH$^+$); $t_R$=2.14, (UV, ELSD) 86%, 99%. $^1$H NMR (500 MHz, CDCl$_3$): 1.30 (t, 3H), 2.34 (s, 6H), 4.21 (q, 2H), 6.28 (b, 1H), 7.59 (s, 2H), 9.92 (s, 1H).

The following compounds were prepared analogously:

(4-Formyl-2,6-dimethyl-phenyl)-carbamic acid propyl ester

Yield: 60%. LC-MS (m/z) 236 (MH$^+$); $t_R$=2.42, (UV, ELSD) 96%, 99%. $^1$H NMR (500 MHz, DMSO-d$_6$): 0.92 (t, 3H), 1.63 (m, 2H), 2.25 (s, 6H), 4.02 (t, 2H), 7.62 (s, 2H), 9.02 (b, 1H), 9.91 (s, 1H).

2-Cyclopentyl-N-(4-formyl-2,6-dimethyl-phenyl)-acetamide

Yield: 66%. LC-MS (m/z) 260 (MH$^+$); $t_R$=2.52, (UV, ELSD) 97%, 97%. $^1$H NMR (500 MHz, DMSO-d$_6$): 1.23 (m, 2H), 1.53 (m, 2H), 1.63 (m, 2H), 1.79 (m, 2H), 2.22 (s, 6H), 2.27 (m, 1H), 2.35 (d, 2H), 7.61 (s, 2H), 9.46 (s, 1H), 9.91 (s, 1H).

Pentanoic acid (4-formyl-2,6-dimethyl-phenyl)-amide

Yield: 94%. LC-MS (m/z) 234 (MH$^+$); $t_R$=2.27, (UV, ELSD) 95%, 99%. $^1$H NMR (500 MHz, DMSO-d$_6$): 0.92 (t, 3H), 1.45 (m, 2H), 1.63 (m, 2H), 2.20 (s, 6H), 2.35 (t, 2H), 7.60 (s, 2H), 9.45 (s, 1H), 9.90 (s, 1H).

2-(4-Chloro-phenyl)-N-(4-formyl-2,6-dimethyl-phenyl)-acetamide

Yield: 53%. LC-MS (m/z) 302 (MH$^+$); $t_R$=2.72, (UV, ELSD) 96%, 95%. $^1$H NMR (500 MHz, DMSO-d$_6$): 2.17 (s, 6H), 3.70 (s, 2H), 7.40 (m, 4H), 7.60 (s, 2H), 9.75 (s, 1H), 9.90 (s, 1H).

(4-Formyl-2,6-dimethyl-phenyl)-carbamic acid 2-methoxy-ethyl ester

Yield: 47%. LC-MS (m/z) 252 (MH$^+$); $t_R$=1.81, (UV, ELSD) 93%, 99%. $^1$H NMR (500 MHz, CDCl$_3$): 2.35 (m, 6H), 3.35 (m, 3H), 3.65 (m, 2H), 4.35 (m, 2H), 6.35 (broad s, 1H), 7.60 (s, 2H), 9.95 (s, 1H).

2-Cyclopentyl-N-(2,6-dichloro-4-formyl-phenyl)-acetamide

Yield: 85%. LC-MS (m/z) 300 (MH$^+$); $t_R$=2.89, (UV, ELSD) 96%, 98%. $^1$H NMR (500 MHz, CDCl$_3$): 1.25 (m, 2H), 1.63 (m, 4H), 1.95 (m, 2H), 2.45 (m, 1H), 2.50 (d, 2H), 7.17 (broad, 1H), 7.83 (s, 2H), 9.90 (s, 1H).

(4-Bromo-2,6-dimethyl-phenyl)-carbamic acid 2-methoxy-ethyl ester

4-Bromo-2,6-dimethyl-aniline (2.00 g) and chloroformic acid 2-methoxyethyl ester (1.52 g) were dissolved in acetonitrile (25 mL) and heated to 130° C. for 15 minutes in a sealed microwave process vial. Water (25 mL) was added to the reaction mixture, and the product was collected by filtration and washed with water (25 mL) and heptane (25 mL) to furnish 2.48 g (82% yield) of the title compound as a white solid. LC-MS (m/z) 304 (MH$^+$); $t_R$=2.93, (UV, ELSD) 96%, 97%. $^1$H NMR (500 MHz, CDCl$_3$): 2.36 (m, 6H), 3.40 (m, 3H), 3.60 (m, 2H), 4.35 (m, 2H), 6.55 (broad s, 1H), 7.45 (s, 2H).

N-(4-Bromo-2,6-dichloro-phenyl)-2-cyclopentyl-acetamide

4-Bromo-2,6-dichloroaniline (12.1 g) and cyclopentylacetyl chloride (8.1 g) were dissolved in tetrahydrofuran (100 mL) and sodiumcarbonate (6.4 g) is added, followed by heating to reflux for 6 hours. The reaction mixture was cooled to ambient temperature and filtered and diluted with water (250 ml). After extraction, the combined organic phase was concentrated in vacuo to furnish 14.0 g (80% yield) of the title compound as a white solid. LC-MS (m/z) 352 (MH$^+$); $t_R$=3.47, (UV, ELSD) 96%, 99%. $^1$H NMR (500 MHz, DMSO-d$_6$): 1.12 (m, 2H), 1.50 (m, 4H), 1.80 (m, 2H), 2.15 (m, 1H), 2.50 (d, 2H), 5.70 (broad s, 1H), 7.45 (s, 2H).

N-(2,6-Dimethyl-4-nitro-phenyl)-acetamide 2,6-Dimethylaniline (30.2 g) was added slowly to acetic anhydride (200 mL) cooled to 0° C. over 10 minutes. After 30 minutes, acetic acid (40 mL) and fuming nitric acid (15 mL)

were added to the reaction mixture and the cooling was removed. The reaction mixture was filtered after 1 hour and the crystals were washed with water and dried in vacuo to furnish 5.20 g (30% yield) of the title compound as a yellow solid. $^1$H NMR (500 MHz, DMSO-d$_6$): 2.10 (s, 3H), 2.26 (s, 6H), 7.98 (s, 2H), 9.61 (s, 1H).

N-(4-Amino-2,6-dimethyl-phenyl)-acetamide

Zinc dust (30 g) was added in portions over 10 minutes to N-(2,6-dimethyl-4-nitro-phenyl)-acetamide (5.09 g) in tetrahydrofuran (200 mL) and acetic acid (60 mL) cooled to 0° C. The reaction mixture was filtered after 30 minutes through silica-(50 g), which was washed with methanol/ethyl acetate (20:80, 100 mL). The organic phase was washed with saturated aqueous sodium bicarbonate (100 mL) and treated with heptane until the title compound precipitated, which was collected, washed with heptane and dried in vacuo to furnish 1.20 g (28% yield) of the title compound as a pale red solid. $^1$H NMR (500 MHz, DMSO-d$_6$): 1.95 (s, 3H), 1.96 (s, 6H), 4.82 (s, 2H), 6.23 (s, 2H), 8.79 (s, 1H).

2,6-Dimethyl-4-nitro-phenylamine

Concentrated hydrochloric acid (17.5 mL) was added to N-(2,6-dimethyl-4-nitro-phenyl)-acetamide (5.05 g) and heated to 140° C. for 30 minutes in a sealed microwave process vial. The reaction mixture was neutralized with solid sodium carbonate in water and the precipitated product was collected by filtration and washed with water (100 mL) to furnish 3.93 g (97% yield) of the title compound as a yellow solid. $^1$H NMR (500 MHz, DMSO-d$_6$): 2.15 (s, 6H), 6.15 (b, 2H), 7.79 (s, 2H).

2-Cyclopentyl-N-(2,6-dimethyl-4-nitro-phenyl)-acetamide 2,6-Dimethyl-4-nitro-phenylamine (0.98 g) and cyclopentylacetyl chloride (0.99 mL) were dissolved in acetonitrile (10 mL) and heated to 150° C. for 5 minutes in a sealed microwave process vial. Water (10 mL) was added to the reaction mixture, and the product was collected by filtration and washed with water (20 mL) and heptane (20 mL) to furnish 1.45 g (89% yield) of the title compound as a yellow solid. $^1$H NMR (500 MHz, DMSO-d$_6$): 1.24 (m, 2H), 1.54 (m, 2H), 1.63 (m, 2H), 1.79 (m, 2H), 2.25 (s, 6H), 2.27 (m, 1H), 2.36 (d, 2H), 7.98 (s, 2H), 9.56 (s, 1H).

The following compound was prepared analogously:

N-(2,6-Dimethyl-4-nitro-phenyl)-3,3-dimethyl-butyramide

Yield: 96%. $^1$H NMR (500 MHz, DMSO-d$_6$): 1.07 (s, 9H), 2.26 (s, 2H), 2.27 (s, 6H), 7.98 (s, 2H), 9.52 (s, 1H).

N-(2-Chloro-6-methyl-4-nitro-phenyl)-2-(4-fluoro-phenyl)-acetamide

LC-MS (m/z) 323 (MH$^+$); t$_R$=2.85, (UV, ELSD) 57%, 98%

N-(2-Chloro-4-nitro-6-trifluoromethyl-phenyl)-2-cyclopentyl-acetamide

LC-MS (m/z) 351 (MH$^+$); t$_R$=3.10, (UV, ELSD) 97%, 98%. $^1$H NMR (500 MHz, CDCl$_3$): 1.20 (m, 2H), 1.60 (m, 4H), 1.90 (m, 2H), 2.35 (m, 1H), 2.50 (d, 2H), 7.1 (broad, 1H), 8.45 (d, 1H), 8.55 (d, 1H).

N-(4-Amino-2,6-dimethyl-phenyl)-2-cyclopentyl-acetamide

Zinc dust (10 g) was added in portions over 10 minutes to 2-cyclopentyl-N-(2,6-dimethyl-4-nitro-phenyl)-acetamide (1.45 g) in tetrahydrofuran (40 mL) and acetic acid (10 mL) cooled to 0° C. The reaction mixture was stirred 2 hours at 25° C., neutralized with solid sodium carbonate and filtered through silica (50 g), which was washed with ethyl acetate (200 mL). The organic phase was concentrated in vacuo to furnish 1.15 g (89% yield) of the title compound as a light orange solid. $^1$H NMR (500 MHz, DMSO-d$_6$): 1.20 (m, 2H), 1.51 (m, 2H), 1.60 (m, 2H), 1.75 (m, 2H), 1.96 (s, 6H), 2.22 (m, 1H), 2.23 (d, 2H), 4.81 (b, 2H), 6.23 (s, 2H), 8.74 (s, 1H).

The following compound was prepared analogously:

N-(4-Amino-2,6-dimethyl-phenyl)-3,3-dimethyl-butyramide

Yield: 96%. $^1$H NMR (500 MHz, DMSO-d$_6$): 1.04 (s, 9H), 1.98 (s, 6H), 2.13 (s, 2H), 4.81 (b, 2H), 6.24 (s, 2H), 8.69 (s, 1H).

N-(4-Amino-2-chloro-6-methyl-phenyl)-2-(4-fluoro-phenyl)-acetamide

LC-MS (m/z) 293 (MH$^+$); t$_R$=1.77, (UV, ELSD) 98%, 99%.

N-(4-Amino-2-chloro-6-trifluoromethyl-phenyl)-2-cyclopentyl-acetamide

LC-MS (m/z) 321 (MH$^+$); t$_R$=2.52, (UV, ELSD) 92%, 96%. $^1$H NMR (500 MHz, DMSO-d$_6$): 1.15 (m, 2H), 1.55 (m, 4H), 1.75 (m, 2H), 2.20 (m, 2H), 2.40 (m, 1H), 5.80 (s, 2H), 6.85 (d, 1H), 6.95 (d, 1H), 9.20 (s, 1H).

N-(4-Bromo-2-methyl-6-nitro-phenyl)-3,3-dimethyl-butyramide

4-Bromo-2-methyl-6-nitro-phenylamine (2.22 g) and tert-butylacetyl chloride (1.30 g) were mixed in acetonitrile (3 mL) and heated to 140° C. for 40 minutes in a sealed microwave process vial. Water (5 mL) was added and the product was collected by filtration and washed with water and heptane to furnish 2.80 g (86% yield) of the title compound as a yellow solid. LC-MS (m/z) 329 (MH$^+$); t$_R$=3.07, (UV, ELSD) 96%, 99%. $^1$H NMR (500 MHz, DMSO-d$_6$): 1.01 (s, 9H), 2.21 (s, 2H), 2.29 (s, 3H), 7.87 (d, 1H), 7.95 (d, 1H), 9.77 (s, 1H).

2,6,N'-Trimethyl-N'-(4-trifluoromethyl-benzyl)-benzene-1,4-diamine

Concentrated aqueous hydrochloric acid (2 mL) was added to N-{2,6-dimethyl-4-[methyl-(4-trifluoromethyl-benzyl)-amino]-phenyl}-acetamide (0.20 g) and heated to 130° C. for 80 minutes in a sealed microwave process vial. The crude mixture was poured onto solid potassium hydroxide (2 g) mixed with ice. The product was extracted with 1,2-dichloroethane (100 mL), and the organic phase was filtered through solid sodium carbonate (5 g), dried over magnesium sulfate and concentrated in vacuo to furnish 0.10 g (57% yield) of the title compound as a pale brown oil. LC-MS (m/z) 309 (MH$^+$); t$_R$=2.11, (UV, ELSD) 99%, 98%. $^1$H NMR (500 MHz, DMSO-d$_6$): 2.03 (s, 6H), 2.76 (s, 3H), 3.94 (b, 2H), 4.41 (s, 2H), 6.39 (s, 2H), 7.42 (d, 2H), 7.65 (d, 2H).

(2,6-Dimethyl-phenyl)-carbamic acid propyl ester 2,6-Dimethyl-aniline (3.0 mL) and propyl chloroformate (4.1 mL) were dissolved in acetonitrile (15 mL) and heated to 150° C. for 10 minutes in a sealed microwave process vial. The reaction mixture was concentrated in vacuo to furnish 4.79 g (95% yield) of the title compound as a brown solid. The crude product was used without further purification.
$^1$H NMR (500 MHz, CDCl$_3$): 0.98 (t, 3H), 1.70 (m, 2H), 2.26 (s, 6H), 4.10 (t, 2H), 6.02 (s, 1H), 7.07 (m, 3H).

(2,6-Dimethyl-4-nitro-phenyl)-carbamic acid propyl ester

To a solution of concentrated nitric acid (6.4 mL) in water (30 mL) was added (2,6-dimethyl-phenyl)-carbamic acid propyl ester (2.72 g), acetic acid (30 mL) and sodium nitrite (1.0 g). The reaction mixture was refluxed for 16 hours, water (200 mL) was added and the mixture was cooled to 0° C. The product was collected by filtration and dried in vacuo to furnish 1.40 g (42% yield) of the title compound as a yellow solid. The crude product was used without further purification. $^1$H NMR (500 MHz, DMSO-d$_6$): 0.92 (t, 3H), 1.63 (m, 2H), 2.29 (s, 6H), 4.04 (t, 2H), 7.98 (s, 2H), 9.11 (b, 1H).

(4-Amino-2,6-dimethyl-phenyl)-carbamic acid propyl ester

Aqueous hydrochloric acid (6 M, 8.3 mL) was added slowly to a mixture of zinc dust (4.9 g) and (2,6-dimethyl-4-nitro-phenyl)-carbamic acid propyl ester (1.26 g) in tetrahydrofuran (50 mL) cooled to 0° C. The reaction mixture was then stirred for 5 hours at 25° C., and the pH adjusted to 10 with 25% aqueous ammonia. The product was extracted with ethyl acetate (3×50 mL), the combined organic phases were dried over magnesium sulfate and concentrated in vacuo to furnish 1.1 g (99% yield) of the title compound as a dark oil. The crude product was used without further purification. $^1$H NMR (500 MHz, DMSO-d$_6$): 0.91 (t, 3H), 1.60 (m, 2H), 1.99 (s, 6H), 3.95 (t, 2H), 4.82 (s, 2H), 6.23 (s, 2H), 8.14 (s, 1H).

4-(3,5-Difluoro-2-nitro-phenyl)-morpholine 2,4,6-Trifluoronitrobenzene (4.95 g) and potassium carbonate (4.63 g) were mixed in dry dimethyl sulfoxide (40 mL) and cooled to 10° C. under argon. Morpholine (2.56 mL) was added and the reaction mixture was allowed to warm to 25° C. and stirred under argon for 16 hours. The reaction mixture was concentrated in vacuo, brine (50 mL) was added and the product was extracted with ethyl acetate (3×50 mL), the combined organic phases were dried over magnesium sulfate and concentrated in vacuo. The crude material was purified by flash chromatography to furnish 3.69 g (54% yield) of the title compound as a yellow oil.
$^1$H NMR (500 MHz, DMSO-d$_6$): 3.02 (t, 4H), 3.66 (t, 4H), 7.08 (dt, 1H), 7.22 (m, 1H).

2,4-Difluoro-6-morpholin-4-yl-phenylamine

Concentrated hydrochloric acid (6.3 mL) was added slowly to a mixture of zinc dust (4.9 g) and 4-(3,5-difluoro-2-nitro-phenyl)-morpholine (3.69 g) in tetrahydrofuran (40 mL) cooled to 0° C. The reaction mixture was then stirred for 1 hour at 0° C. and 2 hours at 25° C. The reaction mixture was filtered through Celite (10 g), concentrated in vacuo and purified by flash chromatography to furnish 1.76 g (54% yield) of the title compound as an orange solid. GC-MS (m/z) 215 (M$^+$); t$_R$=5.11. $^1$H NMR (500 MHz, DMSO-d$_6$): 2.81 (t, 4H), 3.76 (t, 4H), 4.52 (s, 2H), 6.66 (dt, 1H), 6.82 (m, 1H).

2-Bromo-4-nitro-6-trifluoromethyl-phenylamine

Bromine (0.60 mL) dissolved in acetic acid (11 mL) was added dropwise to a solution of 4-nitro-2-trifluoromethyl-phenylamine (2.4 g) in acetic acid (12 mL). The reaction mixture was heated to 120° C. for 2½ hours, poured into water (400 mL) and filtered. The collected solid was washed with water (200 mL) and dried in vacuo to furnish 3.03 g (91% yield) of the title compound as a yellow solid. $^1$H NMR (500 MHz, DMSO-d$_6$): 7.08 (s, 2H), 8.23 (d, 1H), 8.51 (d, 1H).

N-(2-Bromo-4-nitro-6-trifluoromethyl-phenyl)-3-cyclohexyl-propionamide

2-Bromo-4-nitro-6-trifluoromethyl-phenylamine (2.0 g) and cyclohexylpropionyl chloride (1.30 mL) were mixed in acetonitrile (10 mL) and heated to 150° C. for 10 minutes in a sealed microwave process vial. The reaction was cooled to 0° C., the product filtered off and washed with cold acetonitrile (50 mL) affording 0.97 g (33% yield) of the title compound as a yellow solid. The crude product was used without further purification. LC-MS (m/z) 424 (MH$^+$); t$_R$=3.53, (UV, ELSD) 95%, 99%. $^1$H NMR (500 MHz, DMSO-d$_6$): 0.88 (m, 2H), 1.17 (m, 3H), 1.28 (m, 1H), 1.51 (m, 2H), 1.68 (m, 5H), 2.38 (t, 2H), 8.45 (d, 1H), 8.82 (d, 1H), 10.17 (s, 1H).

N-(4-Amino-2-bromo-6-trifluoromethyl-phenyl)-3-cyclohexyl-propionamide

Acetic acid (3.70 mL) was added slowly to a mixture of zinc dust (7.88 g) and N-(2-bromo-4-nitro-6-trifluoromethyl-phenyl)-3-cyclohexyl-propionamide (1.99 g) in tetrahydrofuran (40 mL). The reaction mixture was then stirred for 1½ hours at 25° C. The reaction mixture was filtered, diluted with saturated aqueous sodium bicarbonate (400 mL) and extracted with ethyl acetate (3×100 mL). The combined organic phases were washed with water (100 mL), brine (100 mL), dried over sodium sulfate and concentrated in vacuo to furnish 1.85 g (100% yield) of the title compound as a yellow solid. LC-MS (m/z) 394 (MH$^+$); t$_R$=3.22, (UV, ELSD) 92%, 99%. $^1$H NMR (500 MHz, DMSO-d$_6$): 0.86 (q, 2H), 1.17 (m, 3H), 1.26 (m, 1H), 1.46 (q, 2H), 1.67 (m, 5H), 2.40 (t, 2H), 5.83 (s, 2H), 6.88 (d, 1H), 7.07 (d, 1H), 9.27 (s, 1H).

[2-Methyl-6-nitro-4-(4-trifluoromethyl-benzylamino)-phenyl]-carbamic acid ethyl ester (4-Amino-2-methyl-6-nitro-phenyl)-carbamic acid ethyl ester (0.50 g) and 4-trifluoromethyl-benzaldehyde (0.29 mL) were dissolved in ethanol (10 mL) and refluxed for 16 h. The reaction mixture was poured into water (75 mL) and the precipitate collected by filtration. Sodium cyanoborohydride (0.3 g) and acetic acid (0.5 mL) were added to the precipitate dispersed in methanol (10 mL) and stirred for 60 minutes. The reaction mixture was filtered, water (50 mL) was added and the organic solvent was removed in vacuo. The product was allowed to precipitate at 25° C. and collected by filtration and washed with water (100 mL) to furnish 0.47 g (75% yield) of the title compound as a yellow solid. LC-MS (m/z) 398 (MH$^+$); t$_R$=3.18, (UV, ELSD) 86%, 94%. $^1$H NMR (500 MHz, DMSO-d$_6$): 1.20 (1,3H), 2.10 (s, 3H), 4.05 (m, 2H), 4.45 (m, 2H), 6.75 (m, 1H), 6.90 (m, 1H), 7.55 (m, 2H), 7.73 (m, 2H), 8.75 (s, 1H).

(4-Amino-3,5-dimethyl-phenyl)-(4-trifluoromethyl-benzyl)-carbamic acid tert-butyl ester To (3,5-Dimethyl-4-nitro-phenyl)-(4-trifluoromethyl-benzyl)-carbamic acid tert-butyl ester (9.5 g) in ethanol (150 mL) was added zinc dust (22 g) and acetic acid (13 mL). The reaction mixture was stirred 3 hours and then filtered. The solution was concentrated in vacuo, redissolved in ethyl acetate (100 mL) and extracted with water (2×50 mL). The organic phase was dried (MgSO$_4$), filtered and concentrated in vacuo to give the title compound as an off white compound. Yield. 6.5 g (78%). LC-MS (m/z) 395 (MH$^+$); $t_R$=3.06, (UV, ELSD) 89%, 96%. $^1$H NMR (500 MHz, CDCl$_3$): 1.40 (s, 9H), 2.10 (s, 6H), 3.50 (broad, 2H), 4.75 (s, 2H), 6.70 (s, 2H), 7.35 (d, 2H), 7.55 (d, 2H).

(3,5-Dimethyl-4-nitro-phenyl)-(4-trifluoromethyl-benzyl)-carbamic acid tert-butyl ester To (3,5-Dimethyl-4-nitro-phenyl)-(4-trifluoromethyl-benzyl)-amine (7.7 g) in acetonitrile (150 mL) was added 4-dimethylaminopyridine (1.45 g), triethylamine (4.95 mL) and di-tert-butyl dicarbonate (5.71 g). The reaction mixture was stirred for 12 hours, and purified by flash chromatography to furnish 9.6 g (95% yield) of the title compound as a white solid. LC-MS (m/z) 299 (MH$^+$); $t_R$=3.09, (UV, ELSD) 100%, 99%. $^1$H NMR (500 MHz, CDCl$_3$): 0.93 (t, 3H), 1.39 (m, 4H), 1.76 (qui, 2H), 2.20 (s, 6H), 2.40 (t, 2H), 6.57 (b, 1H), 7.23 (s, 2H).

(3,5-Dimethyl-4-nitro-phenyl)-(4-trifluoromethyl-benzyl)-amine 3,5-Dimethyl-4-nitro-phenylamine (3.95 g) and 4-trifluoromethyl-benzaldehyde (4.87 mL) were dissolved in ethanol (50 mL) and refluxed for 16 h. The reaction mixture was poured into water (75 mL) and the precipitate collected by filtration. Sodium cyanoborohydride (3.1 g) and acetic acid (7.0 mL) were added to the precipitate dispersed in methanol (130 mL) and stirred for 60 minutes. The reaction mixture was filtered, water (350 mL) was added and the organic solvent was removed in vacuo. The product was allowed to precipitate at 25° C. and collected by filtration and washed with water (300 mL) to furnish 6.7 g (85% yield) of the title compound as a yellow solid. LC-MS (m/z) 325 (MH$^+$); $t_R$=2.00, (UV, ELSD) 92%, 93%. $^1$H NMR (500 MHz, CDCl$_3$): 2.30 (s, 6H), 4.45 (broad, 3H), 6.25 (s, 2H), 7.45 (d, 2H), 7.60 (d, 2H).

2-Chloro-4-nitro-6-trifluoromethylaniline

4-Nitro-2-trifluoromethylaniline (15 g) and N-chlorosuccinimide (10.7 g) dissolved in acetonitril (100 ml) was heated to 150° C. for 15 minutes in a sealed microwave process vial. The reaction mixture was cooled to ambient temperature and poured into 5% sodium hydroxide (500 ml) and ethylacetate (400 ml). After seperation the organic phase was dried (MgSO$_4$), filtered and concentrated in vacuo, followed by purification by flash chromatography to furnish 17.0 g (97% yield) of the title compound as a yellow solid. LC-MS (m/z) 240 (MH$^+$); $t_R$=4.76, (UV, ELSD) 97%, 96%. $^1$H NMR (500 MHz, DMSO-d$_6$): 7.15 (s, 2H), 8.15 (d, 1H), 8.40 (d, 1H).

The following compound was prepared analogously:

2-Chloro-6-methyl-4-nitro-phenylamine

LC-MS (m/z) 186 (MH$^+$); $t_R$=6.40, (UV, ELSD) 97%, 98%. $^1$H NMR (500 MHz, DMSO-d$_6$): 2.20 (s, 3H), 6.55 (s, 2H), 7.90 (d, 1H), 8.00 (d, 1H).

Compounds of the Invention

Acid addition salts of the compounds of the invention may easily be formed by methods known to the person skilled in the art.

EXAMPLE 1

1a Hexanoic acid (4-bromo-2,6-dimethyl-phenyl)-amide

4-Bromo-2,6-dimethyl-aniline (0.50 g) and hexanoyl chloride (0.45 mL) were dissolved in acetonitrile (4 mL) and heated to 150° C. for 10 minutes in a sealed microwave process vial. The reaction mixture was concentrated in vacuo and purified by flash chromatography to furnish 0.37 g (50% yield) of the title compound as a white solid. LC-MS (m/z) 299 (MH$^+$); $t_R$=3.09, (UV, ELSD) 100%, 99%. $^1$H NMR (500 MHz, CDCl$_3$): 0.93 (t, 3H), 1.39 (m, 4H), 1.76 (qui, 2H), 2.20 (s, 6H), 2.40 (t, 2H), 6.57 (b, 1H), 7.23 (s, 2H).

The following compound was prepared analogously:

1b N-(4-Bromo-2,6-dimethyl-phenyl)-2-(4-fluoro-phenyl)-acetamide

Yield: 24%. LC-MS (m/z) 337 (MH$^+$); $t_R$=3.04, (UV, ELSD) 97%, 98%. $^1$H NMR (500 MHz, DMSO-d$_6$): 2.05 (s, 6H), 3.63 (s, 2H), 7.16 (t, 2H), 7.27 (t, 2H), 7.38 (t, 2H), 9.46 (s, 1H).

1c N-(2-Bromo-4,6-dimethyl-phenyl)-2-(4-fluoro-phenyl)-acetamide

2-Bromo-4,6-dimethyl-aniline (600 mg) and (4-fluoro-phenyl)-acetyl chloride (543 mg) were dissolved in acetonitrile (6 mL) and heated to 150° C. for 10 minutes in a sealed microwave process vial. The reaction was cooled to 0° C., the product filtered off and washed with cold acetonitrile (50 mL) affording 665 mg (66% yield) of the title compound as a white solid. LC-MS (m/z) 337 (MH$^+$); $t_R$=2.93, (UV, ELSD) 90%, 98%. $^1$H NMR (500 MHz, DMSO-d$_6$): 2.05 (s, 6H), 2.25 (s, 3H), 3.63 (s, 2H), 7.05 (b, 1H), 7.15 (dt, 2H), 7.32 (b, 1H), 7.40 (dt, 2H), 9.67 (s, 1H).

The following compounds were prepared analogously:

1d N-(2-Bromo-4,6-dimethyl-phenyl)-3,3-dimethyl-butyramide

Yield: 98%. LC-MS (m/z) 299 (MH$^+$); $t_R$=3.06, (UV, ELSD) 77%, 97%.

1e N-(2-Bromo-4,6-dimethyl-phenyl)-2-cyclopentyl-acetamide

Yield: 75%. LC-MS (m/z) 311 (MH$^+$); $t_R$=3.08, (UV, ELSD) 77%, 99%.

1f N-(2-Bromo-4,6-dichloro-phenyl)-3,3-dimethyl-butyramide

Yield: 70%. LC-MS (m/z) 340 (MH$^+$); $t_R$=3.17, (UV, ELSD) 82%, 98%.

1g N-(2-Bromo-4,6-dichloro-phenyl)-2-(4-fluoro-phenyl)-acetamide

Yield: 80%. LC-MS (m/z) 378 (MH$^+$); $t_R$=3.07, (UV, ELSD) 99%, 98%.

1h N-(2-Bromo-4,6-dichloro-phenyl)-2-cyclopentyl-acetamide

Yield: 66%. LC-MS (m/z) 352 (MH$^+$); t$_R$=3.18, (UV, ELSD) 94%, 99%.

1i Heptanoic acid (4-bromo-2,6-dimethyl-phenyl)-amide

Heptanoyl chloride (16 mg) was added to 4-bromo-2,6-dimethyl-aniline (20 mg) dissolved in acetonitrile and heated to 70° C. for 16 hours. The reaction mixture was concentrated in vacuo, redissolved in dimethyl sulfoxide/methanol (1:1, 0.5 mL) and subjected to preparative LC-MS purification to furnish 10 mg (33% yield) of the title compound as an oil. LC-MS (m/z) 313 (MH$^+$); t$_R$=3.33, (UV, ELSD) 93%, 100%.

The following compounds were prepared analogously:

1j Cyclohexanecarboxylic acid (4-bromo-Z 6-dimethyl-phenyl)-amide

Yield: 22%. LC-MS (m/z) 311 (H+); t$_R$=3.06, (UV, ELSD) 97%, 100%.

1k N-(4-Bromo-2,6-dimethyl-phenyl)-2-thiophen-2-yl-acetamide

Yield: 14%. LC-MS (m/z) 325 (MH$^+$); t$_R$=2.85, (UV, ELSD) 97%, 100%.

1l 2-Phenyl-cyclopropanecarboxylic acid (4-bromo-2,6-dimethyl-phenyl)-amide

Yield: 15%. LC-MS (m/z) 345 (MH$^+$); t$_R$=3.22, (UV, ELSD) 97%, 100%.

1m N-(4-Bromo-2,6-dimethyl-phenyl)-2-(4-chloro-phenyl)-acetamide

Yield: 49%. LC-MS (m/z) 353 (MH$^+$); t$_R$=3.16, (UV, ELSD) 99%, 100%.

1n Pentanoic acid (4-bromo-2,6-dimethyl-phenyl)-amide

Yield: 54%. LC-MS (m/z) 285 (MH$^+$); t$_R$=2.81, (UV, ELSD) 99%, 100%.

1o Octanoic acid (4-bromo-2,6-dimethyl-phenyl)-amide

Yield: 44%. LC-MS (m/z) 327 (MH$^+$); t$_R$=3.58, (UV, ELSD) 100%, 100%.

1p N-(4-Bromo-2,6-dimethyl-phenyl)-2-cyclopentyl-acetamide

4-Bromo-2,6-dimethyl-aniline (4.3 g) and cyclopentylacetyl chloride (3.46 g) were mixed in acetonitrile (50 mL) and tetrahydrofuran (20 mL) and the reaction mixture was heated to reflux for 1 hour. Potassium carbonate (4.5 g) was added and the reaction mixture was refluxed for 1 hour and then poured onto crushed ice and saturated aqueous potassium carbonate (50 mL). The product was collected by filtration and washed with water (100 mL) to furnish 6.6 g (100% yield) of the title compound as a solid. LC-MS (m/z) 311 (MH$^+$); t$_R$=3.07, (UV, ELSD) 100%, 100%. $^1$H NMR (500 MHz, DMSO-d$_6$): 1.21 (m, 2H), 1.52 (m, 2H), 1.61 (m, 2H), 1.77 (m, 2H), 2.11 (s, 6H), 2.25 (m, 1H), 2.31 (d, 2H), 7.27 (s, 2H), 9.23 (s, 1H).

1q 2-Bicyclo[2.2.1]hept-2-yl-N-(2,4-difluoro-6-morpholin-4-yl-phenyl)-acetamide.

Bicyclo[2.2.1]hept-2-yl-acetic acid (0.20 mL), N,N-diisopropyl-ethylamine (0.50 mL) and N-[(dimethylamino)-1H-1,2,3-triazolo-[4,5-b]pyridin-1-yl-methylene]-N-methyl-methanaminium hexafluoro-phosphate N-oxide (0.55 g) were mixed in dry N,N-dimethylformamide (3 mL) and stirred under argon for 2 minutes. 2,4-Difluoro-6-morpholin-4-yl-phenylamine (0.20 g) dissolved in dry N,N-dimethylformamide (2 mL) was added to the reaction mixture, which was stirred at 60° C. under argon for 16 hours. Ethyl acetate (20 mL) was added and the organic phase was washed with saturated aqueous ammonium chloride/water (1:1, 20 mL), water (20 mL), brine/water (1:1, 20 mL), dried over magnesium sulfate, concentrated in vacuo and purified by flash chromatography to furnish 0.17 g (51% yield) of the title compound as a white solid. LC-MS (m/z) 351 (MH$^+$); t$_R$=2.94, (UV, ELSD) 96%, 99%. $^1$H NMR (500 MHz, DMSO-d$_6$): 1.12 (m, 4H), 1.41 (m, 4H), 1.87 (m, 1H), 1.99 (d, 2H), 2.13 (dd, 1H), 2.20 (m, 1H), 2.27 (dd, 1H), 2.88 (t, 4H), 3.70 (t, 4H), 6.72 (m, 1H), 6.89 (dt, 1H), 9.10 (s, 1H).

1r (S)-2-Amino-N-{2,6-dimethyl-4-[methyl-(4-trifluoromethyl-benzyl)-amino]-phenyl}-3-methyl-butyramide Tert-butyloxycarbonyl-L-valine (21.7 mg), N,N-diisopropyl-ethylamine (35 uL), N-[(dimethylamino)-1H-1,2,3-triazolo-[4,5-b]pyridin-1-yl-methylene]-N-methyl-methanaminium hexafluoro-phosphate N-oxide (0.38 g) and 2,6,N'-trimethyl-N'-(4-trifluoromethyl-benzyl)-benzene-1,4-diamine (15.4 mg) were mixed in dry N,N-dimethylformamide (0.2 mL) and stirred under argon for 2 hours. Brine (2 mL) was added and the reaction mixture was extracted with ethyl acetate (2×2 mL). The combined organic phases were dried over sodium sulfate, concentrated in vacuo and purified by flash chromatography. 15.4 mg (61% yield) of the N-Boc-protected title compound was isolated and it was dissolved in trifluoroacetic acid/dichloromethane (1:1, 2 mL) and stirred at 25° C. for 30 minutes. The reaction mixture was concentrated in vacuo to furnish 18 mg (96% yield) of the title compound. LC-MS-TOF (m/z) 408 (MH$^+$); t$_R$=2.19, (UV, ELSD) 93%, 98%.

The following compound was prepared analogously:

1s (S)-2-Amino-4-methyl-pentanoic acid {2,6-dimethyl-4-[methyl-(4-trifluoromethyl-benzyl)-amino]-phenyl}-amide Yield: 59%. LC-MS-TOF (m/z) 422 (MH$^+$); t$_R$=2.34, (UV, ELSD) 97%, 99%.

1w (R)-2-Amino-4-methylpentanoic acid [2,6-dimethyl-4-(4-trifluoromethylbenzylamino)-phenyl]-amide Yield: 43%. %. LC-MS-TOF (m/z) 408 (MH$^+$); t$_R$=2.14, (UV, ELSD) 96%, 97%.

1t (4-Bromo-2,6-dimethyl-phenyl)-carbamic acid ethyl ester

4-Bromo-2,6-dimethyl-aniline (10 g), ethyl chloroformate (5.4 g) and potassium carbonate (10.4 g) were mixed in tetrahydrofuran (100 mL) and heated to reflux for 16 hours, cooled, filtered and concentrated in vacuo. Heptane (200 mL) was added to the crude product, which was stirred for 30 minutes at 70° C. The mixture was filtered and concentrated in vacuo to furnish 12 g (88% yield) of the title compound as a solid. LC-MS (m/z) 273 (MH$^+$); $t_R$=2.95, (UV, ELSD) 99%, 99%. $^1$H NMR (500 MHz, CDCl$_3$): 1.31 (t, 3H), 2.24 (s, 6H), 4.19 (q, 2H), 5.92 (b, 1H), 7.22 (s, 2H).

1u (4-Bromo-2,6-dimethyl-phenyl)-carbamic acid propyl ester

4-Bromo-2,6-dimethyl-aniline (4.3 g) and propyl chloroformate (2.70 mL) were mixed in acetonitrile (50 mL) and tetrahydrofuran (20 mL) and the reaction mixture was heated to reflux for 1 hour. Potassium carbonate (4.5 g) was added and the reaction mixture was refluxed for 1 hour and then poured onto crushed ice and saturated aqueous potassium carbonate (50 mL). The product was collected by filtration and washed with water (100 mL) to furnish 5.26 g (86% yield) of the title compound as a solid. LC-MS (m/z) 287 (MH$^+$); $t_R$=3.18, (UV, ELSD) 99%, 95%. $^1$H NMR (500 MHz, CDCl$_3$): 0.93 (t, 3H), 1.62 (m, 2H), 2.15 (s, 6H), 4.00 (t, 2H), 7.28 (s, 2H), 8.74 (b, 1H).

1v N-(2-Amino-4-bromo-6-methyl-phenyl)-3,3-dimethyl-butyramide

Zinc dust (16 g) was added in portions over 2 hours to N-(4-bromo-2-methyl-6-nitro-phenyl)-3,3-dimethyl-butyramide (2.74 g) in tetrahydrofuran (50 mL) and acetic acid (12 mL) cooled to 0° C., and then stirred 30 minutes at 25° C. The reaction mixture was poured into a suspension of sodium carbonate (16 g) in tetrahydrofuran and filtered through silica (50 g), which was washed with ethyl acetate (100 mL). The organic phase was concentrated in vacuo to furnish 2.47 g (100% yield) of the title compound as a pale red solid. LC-MS (m/z) 300 (MH$^+$); $t_R$=2.54, (UV, ELSD) 96%, 99%. $^1$H NMR (500 MHz, DMSO-d$_6$): 1.04 (s, 9H), 2.05 (s, 3H), 2.21 (s, 2H), 4.94 (s, 2H), 6.59 (d, 1H), 6.74 (d, 1H), 8.85 (s, 1H).

1x [2-Amino-6-methyl-4-(4-trifluoromethylbenzylamino)-phenyl]-carbamic acid ethyl ester To [2-Methyl-6-nitro-4-(4-trifluoromethyl-benzylamino)-phenyl]-carbamic acid ethyl ester (0.45 g) in tetrahydrofuran (5 mL) was added sodium-dithionite (1.8 g) in water (5 mL). The reaction mixture was stirred 3 hours at 50° C. The reaction mixture was concentrated in vacuo and purified by flash chromatography, to furnish the title compounds as a pale yellow solid. LC-MS (m/z) 368 (MH$^+$); $t_R$=2.39, (UV, ELSD) 95%, 99%. $^1$H NMR (500 MHz, DMSO-d$_6$): 1.20 (t, 3H), 1.90 (s, 3H), 4.00 (m, 2H), 4.30 (d, 2H), 4.40 (s, 2H), 5.75 (s, 2H), 6.00 (t, 1H), 7.50 (d, 2H), 7.65 (d, 2H), 7.85 (s, 1H).

EXAMPLE 2

2a 2-Cyclopentyl-N-{2,6-dimethyl-4-[2-(4-trifluoromethyl-phenyl)-pyrrolidin-1-yl]-phenyl}-acetamide Bis(dibenzylideneacetone)palladium (3.6 mg) and (2'-dicyclohexylphosphanyl-biphenyl-2-yl)-dimethyl-amine (3.7 mg) were mixed in dry toluene (2 mL) under argon for 5 minutes. To this mixture were added cesium carbonate (41 mg), 2-[4-(trifluoromethyl)phenyl]pyrrolidine (15 mg) and N-(4-bromo-2,6-dimethyl-phenyl)-2-cyclopentyl-acetamide (1p, 20 mg) and the reaction was heated to 110° C. in a sealed 4 mL vial under argon for 48 hours. Aqueous sodium bicarbonate (5 mL) was added and the mixture was extracted with ethyl acetate (3×3 mL). The combined organic phases were dried over magnesium sulfate and concentrated in vacuo. The crude product was purified by vacuum liquid chromatography to furnish 7.6 mg (27% yield) of the title compound as an oil. LC-MS-TOF (m/z) 445 (MH$^+$); $t_R$=3.91, (UV, ELSD) 98%, 99%.

2b N-(4-Azepan-1-yl-2,6-dimethyl-phenyl)-2-cyclopentyl-acetamide

Bis(dibenzylideneacetone)palladium (2.8 mg) and (2'-dicyclohexylphosphanyl-biphenyl-2-yl)-dimethyl-amine (3.8 mg) were mixed in dry toluene (2.5 mL) under argon for 5 minutes. To this mixture were added sodium tert-butoxide (6 mg), azacycloheptane (7.5 mg) and N-(4-bromo-2,6-dimethyl-phenyl)-2-cyclopentyl-acetamide (1p, 15 mg) and the reaction was heated to 110° C. in a sealed 4 mL vial under argon for 48 hours. The reaction mixture was concentrated in vacuo, sodium hydroxide (2 M, 1.5 mL) was added and the product was extracted with isopropyl acetate (3×1.5 mL). The combined organic phases were dried over magnesium sulfate, concentrated in vacuo and purified by flash chromatography to furnish 7.9 mg (50% yield) of the title compound as an oil. LC-MS-TOF (m/z) 329 (MH$^+$); $t_R$=2.08, (UV, ELSD) 90%, 99%.

2c 2-Cyclopentyl-N-(2,6-dimethyl-4-pyrrol-1-yl-phenyl)-acetamide

Dibenzylideneacetone (1.1 mg) and 1,10-phenanthroline (17 mg) were mixed in dry toluene (1 mL) under argon for 5 minutes, followed by addition of copper(II) trifluoromethanesulfonate (1.8 mg), cesium carbonate (35 mg), pyrrole (10 mg) and N-(4-bromo-2,6-dimethyl-phenyl)-2-cyclopentyl-acetamide (1p, 30 mg) and the reaction was heated to 110° C. in a sealed 4 mL vial under argon for 48 hours. The reaction mixture was concentrated in vacuo, sodium hydroxide (2 M, 1.5 mL) was added and the product was extracted with isopropyl acetate (3×1.5 mL). The combined organic phases were dried over magnesium sulfate, concentrated in vacuo and redissolved in dimethyl sulfoxide (0.50 mL) of which 0.25 mL was subjected to preparative LC-MS purification to furnish 1.3 mg (9% yield) of the title compound as an oil. LC-MS-TOF (m/z) 297 (MH$^+$); $t_R$=3.11, (UV, ELSD) 97%, 99%.

2d 3,3-Dimethyl-N-[2-methyl-6-morpholin-4-yl-4-(4-trifluoromethylbenzylamino)-phenyl]-butyramide N-(4-Bromo-2-methyl-6-morpholin-4-yl-phenyl)-3,3-dimethyl-butyramide (0.030 g, 6a), 4-trifluorobenzylamine (0.056 g), palladium(II)acetate (0.009 g), rac-2,2'-bis(diphenylphosphino)-1,1'-binaphthyl (0.0028 g) and potassium tert-butoxide (0.010 g) were dissolved in dry dimethylformamide (2 mL) and heated to 180° C. for 15 minutes in a sealed microwave process vial. Saturated aqueous sodium bicarbonate (20 mL) was added and the mixture was extracted with ethyl acetate (3×10 mL), the combined organic phases were dried over sodium sulfate and concentrated in vacuo. The crude product was purified by flash chromatography to furnish 0.014 g (37% yield) of the title compound as a yellow solid. LC-MS (m/z) 464 (MH$^+$); $t_R$=3.02, (UV, ELSD) 89%, 99%.

EXAMPLE 3

3a N-(3'-Amino-3,5-dimethyl-biphenyl-2-yl)-2-(4-fluoro-phenyl)-acetamide

N-(2-Bromo-4,6-dimethyl-phenyl)-2-(4-fluoro-phenyl)-acetamide (1c, 15.1 mg), 3-aminobenzeneboronic acid (30.8 mg), aqueous potassium carbonate (5 M, 90 uL) and palladium(II) acetate (1 mg) were mixed in acetone (2 mL) and heated to 125° C. for 15 minutes in a sealed microwave process vial. The reaction mixture was filtered through silica (500 mg), concentrated in vacuo, redissolved in dimethyl sulfoxide (0.5 mL) and subjected to preparative LC-MS purification to furnish 14.9 mg (95% yield) of the title compound as an oil. LC-MS (m/z) 349 (MH$^+$); $t_R$=1.92, (UV, ELSD) 98%, 99%.

The following compounds were prepared analogously:

3b N-(4'-Dimethylamino-3,5-dimethyl-biphenyl-2-yl)-2-(4-fluoro-phenyl)-acetamide Yield: 12%. LC-MS (m/z) 377 (MH$^+$); $t_R$=2.00, (UV, ELSD) 99%, 99%.

3c N-(2,4-Dimethyl-6-quinolin-3-yl-phenyl)-2-(4-fluoro-phenyl)-acetamide

Yield: 34%. LC-MS (m/z) 384 (MH$^+$); $t_R$=1.95, (UV, ELSD) 97%, 99%.

3d 2-(4-Fluoro-phenyl)-N-(4'-hydroxy-3'-methoxy-3,5-dimethyl-biphenyl-2-yl)-acetamide Yield: 15%. LC-MS (m/z) 380 (MH$^+$); $t_R$=2.71, (UV, ELSD) 91%, 78%.

3e 2-(4-Fluoro-phenyl)-N-(3'-hydroxy-3,5-dimethyl-biphenyl-2-yl)-acetamide

Yield: 52%. LC-MS (m/z) 350 (MH$^+$); $t_R$=2.73, (UV, ELSD) 94%, 90%.

3f 2-(4-Fluoro-phenyl)-N-(2'-methanesulfonylamino-3,5-dimethyl-biphenyl-2-yl)-acetamide Yield: 22%. LC-MS (m/z) 427 (MH$^+$); $t_R$=2.90, (UV, ELSD) 93%, 99%.

3g N-(4'-Isopropyl-3,5-dimethyl-biphenyl-2-yl)-3,3-dimethyl-butyramide

Yield: 19%. LC-MS (m/z) 338 (MH$^+$); $t_R$=3.81, (UV, ELSD) 99%, 99%

3h 2-Cyclopentyl-N-(3,5-dimethyl-biphenyl-2-yl)-acetamide

Yield: 35%. LC-MS (m/z) 308 (MH$^+$); $t_R$=3.32, (UV, ELSD) 98%, 99%.

3i N-(4'-Fluoro-3,5-dimethyl-biphenyl-2-yl)-2-(4-fluoro-phenyl)-acetamide

Yield: 23%. LC-MS (m/z) 352 (MH$^+$); $t_R$=3.20, (UV, ELSD) 99%, 96%.

3j N-(3,5-Dimethyl-3',5'-bis-trifluoromethyl-biphenyl-2-yl)-2-(4-fluoro-phenyl)-acetamide Yield: 9%. LC-MS (m/z) 470 (MH$^+$); $t_R$=3.79, (UV, ELSD) 99%, 99%.

3k N-(3'-Acetylamino-3,5-dimethyl-biphenyl-2-yl)-2-(4-fluoro-phenyl)-acetamide Yield: 23%. LC-MS (m/z) 391 (MH$^+$); $t_R$=2.60, (UV, ELSD) 95%, 99%.

3l 2-(4-Fluoro-phenyl)-N-(2'-methoxy-3,5-dimethyl-biphenyl-2-yl)-acetamide

Yield: 12%. LC-MS (m/z) 364 (MH$^+$); $t_R$=3.20, (UV, ELSD) 95%, 99%.

3m N-(3,5-Dimethyl-4'-vinyl-biphenyl-2-yl)-2-(4-fluoro-phenyl)-acetamide

Yield: 20%. LC-MS (m/z) 360 (MH$^+$); $t_R$=3.41, (UV, ELSD) 99%, 99%.

3n N-(3'-Cyano-3,5-dimethyl-biphenyl-2-yl)-2-(4-fluoro-phenyl)-acetamide

Yield: 6%. LC-MS (m/z) 359 (MH$^+$); $t_R$=3.01, (UV, ELSD) 81%, 95%.

3o N-(3,5-Dimethyl-3'-trifluoromethoxy-biphenyl-2-yl)-2-(4-fluoro-phenyl)-acetamide Yield: 20%. LC-MS (m/z) 418 (MH$^+$); $t_R$=3.55, (UV, ELSD) 99%, 99%.

3p N-[2-(2,3-Dihydro-benzo[1,4]dioxin-6-yl)-4,6-dimethyl-phenyl]-2-(4-fluoro-phenyl)-acetamide Yield: 58%. LC-MS (m/z) 392 (MH$^+$); $t_R$=3.06, (UV, ELSD) 99%, 99%.

3q N-[2,4-Dimethyl-6-(2,2,5-trimethyl-2,3-dihydro-benzofuran-7-yl)-phenyl]-2-(4-fluoro-phenyl)-acetamide Yield: 9%. LC-MS (m/z) 418 (MH$^+$); $t_R$=3.80, (UV, ELSD) 99%, 99%.

EXAMPLE 4

4a N-[2,6-Dimethyl-4-(4-trifluoromethyl-benzylamino)-phenyl]-acetamide

N-(4-Amino-2,6-dimethyl-phenyl)-acetamide (1.2 g) and 4-trifluoromethyl-benzaldehyde (1.3 g) were dissolved in ethanol (100 mL) and refluxed for 16 h. The reaction mixture was poured into water (3 L) and the precipitate collected by filtration. Sodium cyanoborohydride (2 g) and acetic acid (2 mL) were added to the precipitate dispersed in methanol (50 mL) and stirred for 15 minutes. The reaction mixture was filtered, water (100 mL) was added and the organic solvent was removed in vacuo. The product was allowed to precipitate at 25° C. and collected by filtration and washed with water (200 mL) to furnish 0.68 g (30% yield) of the title compound as a pale yellow solid. LC-MS (m/z) 337 (MH$^+$); $t_R$=2.39, (UV, ELSD) 99%, 99%. $^1$H NMR (500 MHz, DMSO-d$_6$): 1.95 (s, 3H), 1.96 (s, 6H), 4.34 (d, 2H), 6.18 (t, 1H), 6.25 (s, 2H), 7.55 (d, 2H), 7.69 (d, 2H), 8.81 (s, 1H).

4b N-{2,6-Dimethyl-4-[methyl-(4-trifluoromethyl-benzyl)-amino]-phenyl}-acetamide To a stirred solution of N-[2,6-dimethyl-4-(4-trifluoromethyl-benzylamino)-phenyl]-acetamide (4a, 1.0 g) and formaldehyde (1 mL) in methanol (20 mL) and acetic acid (1 mL) was slowly added sodium cyanoborohydride (0.30 g). After 15 minutes, the reaction mixture was cooled to 5° C. for 16 hours to precipitate the product, which was collected by filtration and washed with water (100 mL) to furnish 0.63 g (60% yield) of the title compound as a pale yellow solid. LC-MS-TOF (m/z) 351 (MH$^+$); $t_R$=2.58, (UV, ELSD) 99%, 99%. $^1$H NMR (500 MHz, DMSO-d$_6$): 1.97 (s, 3H), 2.02 (s, 6H), 2.97 (s, 3H), 4.63 (s, 2H), 7.41 (d, 2H), 7.68 (d, 2H), 8.88 (s, 1H).

4c {4-[(5-Chloro-thiophen-2-ylmethyl)-amino]-2,6-dimethyl-phenyl}-carbamic acid propyl ester (4-Amino-2,6-dimethyl-phenyl)-carbamic acid propyl ester (84 mg) and 5-chloro-thiophene-2-carbaldehyde (48 uL) were dissolved in methanol (3 mL) and heated to 130° C. for 5 minutes in a sealed microwave process vial. Sodium cyanoborohydride (95 mg) was added and the reaction mixture was heated to 130° C. for 5 minutes in a sealed microwave process vial, followed by addition of water/brine (1:1, 3 mL). The product was extracted with ethyl acetate (3×3 mL) and the combined organic phases were washed with brine (5 mL), dried over magnesium sulfate and concentrated in vacuo. The crude product was purified by flash chromatography to furnish 66 mg (49% yield) of the title compound as an oil. LC-MS (m/z) 353 (MH$^+$); $t_R$=3.06, (UV, ELSD) 87%, 87%.

The following compounds were prepared analogously:

4d [4-(4-Fluoro-benzylamino)-2,6-dimethyl-phenyl]-carbamic acid propyl ester Yield: 71%. LC-MS (m/z) 331 (MH$^+$); $t_R$=2.57, (UV, ELSD) 97%, 99%. $^1$H NMR (500 MHz, DMSO-d$_6$): 0.91 (t, 3H), 1.60 (m, 2H), 2.02 (s, 6H), 3.96 (t, 2H), 4.11 (b, 1H), 4.28 (b, 2H), 6.47 (s, 2H), 7.16 (t, 2H), 7.41 (t, 2H), 8.32 (s, 1H).

4e [2,6-Dimethyl-4-(4-trifluoromethyl-benzylamino)-phenyl]-carbamic acid propyl ester Yield: 73%. LC-MS (m/z) 381 (MH$^+$); $t_R$=3.17, (UV, ELSD) 98%, 95%. $^1$H NMR (500 MHz, DMSO-d$_6$): 0.91 (t, 3H), 1.59 (m, 2H), 2.00 (s, 6H), 3.95 (t, 2H), 4.37 (s, 2H), 4.48 (b, 1H), 6.36 (s, 2H), 7.57 (d, 2H), 7.68 (d, 2H), 8.25 (s, 1H).

4f [4-(3-Fluoro-4-trifluoromethyl-benzylamino)-2,6-dimethyl-phenyl]-carbamic acid propyl ester Yield: 61%. LC-MS (m/z) 399 (MH$^+$); $t_R$=3.46, (UV, ELSD) 95%, 95%. $^1$H NMR (500 MHz, DMSO-d$_6$): 0.91 (t, 3H), 1.59 (m, 2H), 1.99 (s, 6H), 3.57 (s, 2H), 3.95 (t, 2H), 4.35 (b, 1H), 6.26 (s, 2H), 7.37 (d, 1H), 7.42 (d, 1H), 7.73 (t, 1H), 8.19 (s, 1H).

4g {2,6-Dimethyl-4-[(4-methyl-2-phenyl-pyrimidin-5-ylmethyl)-amino]-phenyl}-carbamic acid propyl ester (4-Amino-2,6-dimethyl-phenyl)-carbamic acid propyl ester (22 mg) and 4-methyl-2-phenyl-5-pyrimidinecarbaldehyde (20 mg) were dissolved in methanol (0.5 mL) and heated to 170° C. for 10 minutes in a sealed microwave process vial. Sodium cyanoborohydride (2 M in methanol, 250 uL) and acetic acid (100 uL) were added and the reaction mixture was heated to 50° C. for 2 hours. Aqueous sodium carbonate (10%, 1 mL) was added, the product was extracted with ethyl acetate (2×1 mL), and the combined organic phases were concentrated in vacuo. The crude product was redissolved in dimethyl sulfoxide (0.5 mL) of which 0.25 mL was subjected to preparative LC-MS purification to furnish 6.6 mg (33% yield) of the title compound as an oil. LC-MS (m/z) 405 (MH$^+$); $t_R$=3.12, (UV, ELSD) 84%, 99%.

The following compounds were prepared analogously:

4h {2,6-Dimethyl-4-[(6-p-tolyloxy-pyridin-3-ylmethyl)-amino]-phenyl}-carbamic acid propyl ester Yield: 25%. LC-MS (m/z) 420 (MH$^+$); $t_R$=2.90, (UV, ELSD) 83%, 99%.

4i {4-[(6-Methoxy-pyridin-3-ylmethyl)-amino]-2,6-dimethyl-phenyl}-carbamic acid propyl ester Yield: 22%. LC-MS (m/z) 344 (MH$^+$); $t_R$=2.02, (UV, ELSD) 66%, 95%.

4j {4-[(3-Fluoro-4-trifluoromethyl-benzyl)-methyl-amino]-2,6-dimethyl-phenyl}-carbamic acid propyl ester

[4-(3-Fluoro-4-trifluoromethyl-benzylamino)-2,6-dimethyl-phenyl]-carbamic acid propyl ester (4f, 22 mg) and formaldehyde (0.1 mL) were refluxed in methanol (1 mL) for 3 hours. Sodium cyanoborohydride (35 mg) was added and the reaction mixture was stirred for 16 hours at 25° C., followed by addition of water (3 mL). The product was extracted with ethyl acetate (3×3 mL) and the combined organic phases were washed with brine (5 mL), dried over magnesium sulfate and concentrated in vacuo. The crude product was subjected to preparative LC-MS purification to furnish 9.7 mg (43% yield) of the title compound as a solid. LC-MS (m/z) 413 (MH$^+$); $t_R$=3.68, (UV, ELSD) 88%, 96%.

4k 2-Cyclopentyl-N-[2,6-dimethyl-4-(4-trifluoromethyl-benzylamino)-phenyl]-acetamide N-(4-Amino-2,6-dimethyl-phenyl)-2-cyclopentyl-acetamide (207 mg) and 4-trifluoromethyl-benzaldehyde (125 uL) were dissolved in acetonitrile (2 mL) and heated to 150° C. for 5 minutes in a sealed microwave process vial. Sodium cyanoborohydride (0.7 M in methanol, 5 mL) and acetic acid (500 uL) were added and the reaction mixture was stirred at 25° C. for 16 hours. Aqueous sodium carbonate (10%, 25 mL) was added, and the product was collected by filtration to furnish 0.31 g (91% yield) of the title compound as a white solid. LC-MS (m/z) 405 (MH$^+$); $t_R$=3.19, (UV, ELSD) 97%, 99%. $^1$H NMR (500 MHz, DMSO-d$_6$): 1.19 (m, 2H), 1.51 (m, 2H), 1.60 (m, 2H), 1.75 (m, 2H), 1.96 (s, 6H), 2.22 (m, 3H), 4.34 (d, 2H), 6.18 (t, 1H), 6.25 (s, 2H), 7.55 (d, 2H), 7.67 (d, 2H), 8.76 (s, 1H).

4l 2-Cyclopentyl-N-{2,6-dimethyl-4-[methyl-(4-trifluoromethyl-benzyl)-amino]-phenyl}-acetamide To 2-cyclopentyl-N-[2,6-dimethyl-4-(4-trifluoromethyl-benzylamino)-phenyl]-acetamide (4k, 150 mg) dissolved in methanol (20 mL) and acetic acid (2 mL) were added sodium cyanoborohydride (175 mg) and formaldehyde (200 uL) and the reaction mixture was stirred at 25° C. for 70 minutes. The reaction was quenched with saturated aqueous sodium bicarbonate and the product collected by filtration to furnish 151 mg (97% yield) of the title compound as a white solid. LC-MS (m/z) 419 (MH$^+$); $t_R$=3.39, (UV, ELSD) 99%, 99%. $^1$H NMR (500 MHz, DMSO-d$_6$): 1.20 (m, 2H), 1.51 (m, 2H), 1.61 (m, 2H), 1.75 (m, 2H), 2.02 (s, 6H), 2.24 (m, 3H), 2.97 (s, 3H), 4.63 (s, 2H), 6.42 (s, 2H), 7.41 (d, 2H), 7.68 (d, 2H), 8.83 (s, 1H).

4m 2-Cyclopentyl-N-{2,6-dimethyl-4-[(6-trifluoromethyl-pyridin-3-ylmethyl)-amino]-phenyl}-acetamide N-(4-Amino-2,6-dimethyl-phenyl)-2-cyclopentyl-acetamide (204 mg) and 6-trifluoromethyl-pyridine-3-carbaldehyde (163 mg) were dissolved in acetonitrile (3 mL) and heated to 150° C. for 10 minutes in a sealed microwave process vial. The reaction mixture was concentrated in vacuo, redissolved in methanol (5 mL) followed by addition of acetic acid (0.5 mL) and sodium cyanoborohydride (244 mg) and stirred at 25° C. for 16 hours. Aqueous sodium carbonate (10%, 25 mL) was added, and the product was collected by filtration to furnish 0.311 g (92% yield) of the title compound as a white solid. LC-MS (m/z) 406 (MH$^+$); $t_R$=2.90, (UV, ELSD) 98%, 99%. $^1$H NMR (500 MHz, DMSO-d$_6$): 1.20 (m, 2H), 1.51 (m, 2H), 1.60 (m, 2H), 1.75 (m, 2H), 1.97 (s, 6H), 2.22 (m, 3H), 4.39 (d, 2H), 6.20 (t, 1H), 6.28 (s, 2H), 7.85 (d, 1H), 7.99 (d, 1H), 8.75 (s, 1H), 8.77 (s, 1H).

The following compound was prepared analogously:

4n N-{2,6-Dimethyl-4-[(6-trifluoromethyl-pyridin-3-ylmethyl)-amino]-phenyl}-3,3-dimethyl-butyramide Yield: 91%. LC-MS (m/z) 394 (MH$^+$); $t_R$=2.87, (UV, ELSD) 98%, 99%. $^1$H NMR (500 MHz, DMSO-d$_6$): 1.03 (s, 9H), 1.99 (s, 6H), 2.13 (s, 2H), 4.39 (d, 2H), 6.21 (t, 1H), 6.29 (s, 2H), 7.85 (d, 1H), 7.99 (d, 1H), 8.73 (s, 1H), 8.75 (s, 1H).

4o N-{2-Bromo-4-[(5-chloro-thiophen-2-ylmethyl)-amino]-6-trifluoromethyl-phenyl}-3-cyclohexyl-propionamide.

N-(4-Amino-2-bromo-6-trifluoromethyl-phenyl)-3-cyclohexyl-propionamide (1.03 g) and 5-chloro-thiophene-2-carbaldehyde (310 uL) were dissolved in methanol (16 mL) and heated to 130° C. for 8 minutes in a sealed microwave process vial. Sodium cyanoborohydride (800 mg) was added and the reaction mixture was heated to 130° C. for 5 minutes in a sealed microwave process vial. Saturated aqueous sodium bicarbonate (100 mL) was added, the product was extracted with ethyl acetate (3×50 mL) and the combined organic phases were washed with water (2×100 mL) and brine (100 mL), dried over sodium sulfate and concentrated in vacuo. The crude product was purified by flash chromatography to furnish 517 mg (33% yield) of the title compound as a yellow solid. LC-MS (m/z) 524 (MH$^+$); $t_R$=4.09, (UV, ELSD) 99%, 99%. $^1$H NMR (500 MHz, DMSO-d$_6$): 0.86 (q, 2H), 1.15 (m, 3H), 1.26 (m, 1H), 1.46 (q, 2H), 1.65 (m, 5H), 2.24 (t, 2H), 4.89 (d, 2H), 6.94 (d, 1H), 6.95 (d, 1H), 6.98 (d, 1H), 7.04 (t, 1H), 7.13 (d, 1H), 9.32 (s, 1H).

The following compound was prepared analogously:

4p N-{2-Chloro-6-methyl-4-[(6-trifluoromethyl-pyridin-3-ylmethyl)-amino]-phenyl}-2-(3-fluoro-phenyl)-acetamide LC-MS (m/z) 452 (MH$^+$); $t_R$=3.06, (UV, ELSD) 96%, 98%. $^1$H NMR (500 MHz, DMSO-d$_6$): 1.95 (s, 3H), 3.60 (s, 2H), 4.40 (d, 2H), 6.40 (s, 1H), 6.55 (s, 1H), 6.60 (m, 1H), 7.05 (m, 1H), 7.15 (s, 2H), 7.35 (m, 1H), 7.85 (m, 1H), 8.05 (m, 1H), 8.75 (s, 1H), 935 (s, 1H).

4q N-[2-Chloro-6-trifluoromethyl-4-(4-trifluoromethylbenzylamino)-phenyl]-2-cyclopentylacetamide LC-MS (m/z) 481 (MH$^+$); $t_R$=3.52, (UV, ELSD) 99%, 99%. $^1$H NMR (500 MHz, DMSO-d$_6$): 1.15 (m, 2H), 1.45 (m, 2H), 1.55 (m, 2H), 1.75 (m, 2H), 2.15 (m, 1H), 2.20 (m, 2H), 4.55 (d, 2H), 6.90 (m, 2H), 7.15 (m, 1H), 7.55 (d, 2H), 7.75 (d, 2H).

EXAMPLE 5

5a {4-[(3-Fluoro-phenylamino)-methyl]-2,6-dimethyl-phenyl}-carbamic acid ethyl ester To (4-formyl-2,6-dimethyl-phenyl)-carbamic acid ethyl ester (230 mg) and 3-fluoroaniline (122 mg) dissolved in dry ethanol (25 mL) was added 3 Å molecular sieves (0.5 g) and the reaction mixture was refluxed for 16 hours under argon. Upon cooling to 25° C., sodium cyanoborohydride (320 mg) and acetic acid (3 mL) were added and stirred for 1 hour. A second batch of sodium cyanoborohydride (320 mg) was added and the mixture stirred for 1 additional hour. Saturated aqueous sodium carbonate (5 mL) was added and the mixture stirred for 1 hour, water (50 mL) was added and the mixture was extracted with ethyl acetate (3×25 mL). The combined organic phases were dried over magnesium sulfate, concentrated in vacuo and purified by flash chromatography to furnish 95 mg (29% yield) of the title compound as a white solid. LC-MS-TOF (m/z) 317 (MH$^+$); $t_R$=3.37, (UV, ELSD) 99%, 96%. $^1$H NMR (500 MHz, CDCl$_3$): 1.31 (b, 3H), 2.25 (s, 6H), 4.20 (m, 5H), 5.98 (b, 1H), 6.30 (dt, 1H), 6.39 (m, 2H), 7.06 (s, 2H), 7.08 (q, 1H).

The following compounds were prepared analogously:

5b {2,6-Dimethyl-4-[(4-trifluoromethyl-phenylamino)-methyl]-phenyl}-carbamic acid ethyl ester Yield: 20%. LC-MS-TOF (m/z) 367 (MH$^+$); $t_R$=3.62, (UV, ELSD) 98%, 99%. $^1$H NMR (500 MHz, CDCl$_3$): 1.31 (b, 3H), 2.25 (s, 6H), 4.21 (d, 2H), 4.25 (b, 2H), 4.37 (b, 1H), 5.99 (b, 1H), 6.61 (d, 2H), 7.05 (s, 2H), 7.38 (d, 2H).

5c 2-Cyclopentyl-N-{4-[(3-fluoro-phenylamino)-methyl]-2,6-dimethyl-phenyl}-acetamide Yield: 33%. LC-MS (m/z) 355 (MH$^+$); $t_R$=3.22, (UV, ELSD) 99%, 99%. $^1$H NMR (500 MHz, CDCl$_3$): 1.25 (m, 2H), 1.59 (m, 2H), 1.67 (m, 2H), 1.91 (m, 2H), 2.20 (s, 6H), 2.36 (m, 1H), 2.40 (d, 2H), 4.14 (b, 1H), 4.18 (b, 2H), 6.29 (dt, 1H), 6.38 (dt, 2H), 6.77 (b, 1H), 7.04 (s, 2H), 7.08 (q, 1H).

5d N-{4-[(3-Chloro-phenylamino)-methyl]-2,6-dimethyl-phenyl}-2-cyclopentyl-acetamide Yield: 46%. LC-MS (m/z) 371 (MH$^+$); $t_R$=3.43, (UV, ELSD) 99%, 99%. $^1$H NMR (500 MHz, CDCl$_3$): 1.24 (m, 2H), 1.58 (m, 2H), 1.66 (m, 2H), 1.90 (m, 2H), 2.19 (s, 6H), 2.35 (m, 1H), 2.38 (d, 2H), 4.11 (b, 1H), 4.16 (b, 2H), 6.46 (dd, 1H), 6.58 (m, 1H), 6.65 (dd, 1H), 6.84 (b, 1H), 7.02 (s, 2H), 7.05 (m, 1H).

5e 2-Cyclopentyl-N-{4-[(3-methoxy-phenylamino)-methyl]-2,6-dimethyl-phenyl}-acetamide Yield: 32%. LC-MS (m/z) 367 (MH$^+$); $t_R$=2.73, (UV, ELSD) 96%, 99%. $^1$H NMR (500 MHz, CDCl$_3$): 1.25 (m, 2H), 1.58 (m, 2H), 1.66 (m, 2H), 1.90 (m, 2H), 2.20 (s, 6H), 2.35 (m, 1H), 2.39 (d, 2H), 3.75 (s, 3H), 3.99 (b, 1H), 4.19 (b, 2H), 6.18 (m, 1H), 6.25 (dq, 2H), 6.76 (b, 1H), 7.06 (s, 2H), 7.07 (m, 1H).

5f N-{4-[(4-Chloro-phenylamino)-methyl]-2,6-dimethyl-phenyl}-2-cyclopentyl-acetamide Yield: 25%. LC-MS (m/z) 371 (MH$^+$); $t_R$=3.31, (UV, ELSD) 98%, 99%. $^1$H NMR (500 MHz, CDCl$_3$): 1.26 (m, 2H), 1.59 (m, 2H), 1.67 (m, 2H), 1.92 (m, 2H), 2.21 (s, 6H), 2.36 (m, 1H), 2.40 (d, 2H), 4.03 (b, 1H), 4.18 (b, 2H), 6.53 (d, 2H), 6.72 (b, 1H), 7.04 (s, 2H), 7.09 (d, 2H).

5g 2-Cyclopentyl-N-{4-[(3,4-difluoro-phenylamino)-methyl]-2,6-dimethyl-phenyl}-acetamide Yield: 31%. LC-MS (m/z) 373 (MH$^+$); $t_R$=3.27, (UV, ELSD) 97%, 99%. $^1$H NMR (500 MHz, CDCl$_3$): 1.25 (m, 2H), 1.59 (m, 2H), 1.67 (m, 2H), 1.92 (m, 2H), 2.20 (s, 6H), 2.36 (m, 1H), 2.39 (d, 2H), 4.02 (b, 1H), 4.14 (b, 2H), 6.26 (m, 1H), 6.37 (m, 1H), 6.78 (b, 1H), 6.92 (q, 1H), 7.03 (s, 2H).

5h 2-Cyclopentyl-N-{2,6-dimethyl-4-[(4-trifluoromethyl-phenylamino)-methyl]-phenyl}-acetamide Yield: 22%. LC-MS (m/z) 405 (MH$^+$); $t_R$=3.56, (UV, ELSD) 96%, 99%. $^1$H NMR (500 MHz, CDCl$_3$): 1.26 (m, 2H), 1.61 (m, 2H), 1.68 (m, 2H), 1.93 (m, 2H), 2.21 (s, 6H), 2.37 (m, 1H), 2.40 (d, 2H), 4.24 (d, 2H), 4.38 (t, 1H), 6.61 (d, 2H), 6.72 (b, 1H), 7.04 (s, 2H), 7.38 (d, 2H).

5i 2-Cyclopentyl-N-[2,6-dimethyl-4-(p-tolylamino-methyl)-phenyl]-acetamide

Yield: 10%. LC-MS (m/z) 351 (MH$^+$); $t_R$=2.23, (UV, ELSD) 78%, 91%.

5j 2-Cyclopentyl-N-{2,6-dimethyl-4-[(3-trifluoromethyl-phenylamino)-methyl]-phenyl}-acetamide Yield: 10%. LC-MS (m/z) 405 (MH$^+$); $t_R$=3.60, (UV, ELSD) 75%, 99%.

5k 2-Cyclopentyl-N-{4-[(3,5-difluoro-phenylamino)-methyl]-2,6-dimethyl-phenyl}-acetamide Yield: 10%. LC-MS (m/z) 373 (MH$^+$); $t_R$=3.44, (UV, ELSD) 73%, 99%.

5l {4-[(4-Fluoro-phenylamino)-methyl]-2,6-dimethyl-phenyl}-carbamic acid propyl ester Yield: 86%. LC-MS (m/z) 331 (MH$^+$); $t_R$=2.53, (UV, ELSD) 95%, 99%. $^1$H NMR (500 MHz, CDCl$_3$): 0.99 (t, 3H), 1.70 (m, 2H), 2.26 (s, 6H), 3.95 (b, 1H), 4.11 (t, 2H), 4.19 (s, 2H), 5.97 (b, 1H), 6.56 (m, 2H), 6.88 (dt, 2H), 7.07 (s, 2H).

5m {4-[(4-Chloro-phenylamino)-methyl]-2,6-dimethyl-phenyl}-carbamic acid propyl ester Yield: 64%. LC-MS (m/z) 347 (MH$^+$); $t_R$=3.43, (UV, ELSD) 98%, 99%. $^1$H NMR (500 MHz, CDCl$_3$): 0.99 (b, 3H), 1.70 (b, 2H), 2.25 (s, 6H), 4.11 (m, 3H), 4.20 (b, 2H), 5.97 (b, 1H), 6.54 (d, 2H), 7.06 (s, 2H), 7.10 (d, 2H).

5n {2,6-Dimethyl-4-[(4-trifluoromethyl-phenylamino)-methyl]-phenyl}-carbamic acid propyl ester Yield: 61%. LC-MS (m/z) 381 (MH$^+$); $t_R$=3.56, (UV, ELSD) 97%, 99%. $^1$H NMR (500 MHz, CDCl$_3$): 0.99 (b, 3H), 1.70 (b, 2H), 2.26 (s, 6H), 4.12 (m, 3H), 4.27 (b, 2H), 5.98 (b, 1H), 6.62 (d, 2H), 7.06 (s, 2H), 7.39 (d, 2H).

5o {4-[(3,5-Difluoro-phenylamino)-methyl]-2,6-dimethyl-phenyl}-carbamic acid propyl ester Yield: 42%. LC-MS (m/z) 349 (MH$^+$); $t_R$=3.39, (UV, ELSD) 94%, 99%. $^1$H NMR (500 MHz, CDCl$_3$): 0.99 (b, 3H), 1.70 (b, 2H), 2.26 (s, 6H), 4.11 (m, 3H), 4.19 (b, 2H), 5.99 (b, 1H), 6.11 (m, 3H), 7.04 (s, 2H).

5p {4-[(3-Fluoro-phenylamino)-methyl]-2,6-dimethyl-phenyl}-carbamic acid propyl ester Yield: 62%. LC-MS (m/z) 331 (MH$^+$); $t_R$=3.22, (UV, ELSD) 96%, 99%. $^1$H NMR (500 MHz, CDCl$_3$): 0.99 (b, 3H), 1.70 (b, 2H), 2.26 (s, 6H), 4.11 (b, 2H), 4.21 (b, 2H), 5.97 (b, 1H), 6.31 (m, 1H), 6.38 (m, 1H), 7.06 (s, 2H), 7.09 (m, 1H).

5q {4-[(4-Methoxyphenylamino)-methyl]-2,6-dimethylphenyl}-carbamic acid propyl ester Yield: 41%. LC-MS (m/z) 341 (MH$^+$); $t_R$=1.94, (UV, ELSD) 89%, 99%. $^1$H NMR (500 MHz, CDCl$_3$): 1.00 (m, 3H), 1.70 (m, 2H), 2.25 (s, 6H), 3.75 (s, 3H), 3.80 (broad, 1H), 4.10 (broad s, 2H), 4.35 (s, 2H), 5.95 (broad, 1H), 6.60 (d, 2H), 6.80 (d, 2H), 7.10 (s, 2H).

5r Pentanoic acid {4-[(4-chlorophenylamino)-methyl]-Z 6-dimethylphenyl}-amide Yield: 64%. LC-MS (m/z) 345 (MH$^+$); $t_R$=3.10, (UV, ELSD) 98%, 99%. $^1$H NMR (500 MHz, CDCl$_3$): 1.00 (t, 3H), 1.45 (m, 2H), 1.72 (m, 2H), 2.20 (s, 6H), 2.43 (t, 2H), 4.20 (s, 2H), 6.51 (d, 2H), 6.65 (b, 1H), 7.06 (s, 2H), 7.15 (d, 2H).

5s 2-(4-Chlorophenyl)-N-{4-[(4-chlorophenylamino)-methyl]-2,6-dimethylphenyl}-acetamide Yield: 43%. LC-MS (m/z) 415 (MH$^+$); $t_R$=3.52, (UV, ELSD) 97%, 98%. $^1$H NMR (500 MHz, DMSO-d$_6$): 2.00 (s, 6H), 4.15 (broad, 5H), 6.62 (d, 2H), 7.05 (s, 2H), 7.13 (d, 2H), 7.40 (m, 4H).

5t {2,6-Dimethyl-4-[(4-trifluoromethylphenylamino)-methyl]-phenyl}-carbamic acid 2-methoxyethyl ester Yield: 42%. LC-MS (m/z) 397 (MH$^+$); $t_R$=3.22, (UV, ELSD) 97%, 96%. $^1$H NMR (500 MHz, CDCl$_3$): 2.25 (s, 6H), 3.40 (b, 3H), 3.65 (b, 2H), 4.27 (s, 2H), 4.35 (b, 3H), 6.10 (b, 1H), 6.60 (d, 2H), 7.05 (s, 2H), 7.40 (d, 2H).

5u N-{4-[(5-Chloro-pyridin-2-ylamino)-methyl]-2,6-dimethylphenyl}-2-cyclopentylacetamide Yield: 63%. LC-MS (m/z) 372 (MH$^+$); $t_R$=1.93, (UV, ELSD) 97%, 100%. $^1$H NMR (500 MHz, CDCl$_3$): 1.25 (m, 2H), 1.55 (m, 4H), 1.92 (m, 2H), 2.20 (s, 6H), 2.35 (m, 1H), 2.45 (d, 2H), 4.45 (d, 2H), 4.95 (broad t, 1H), 6.35 (d, 1H), 6.75 (s, 1H), 7.05 (s, 2H), 7.35 (d, 1H), 8.05 (s, 1H).

5v 2-Cyclopentyl-N-{4-[(2,6-dichloro-pyridin-4-ylamino)-methyl]-2,6-dimethylphenyl}-acetamide Yield: 47%. LC-MS (m/z) 406 (MH$^+$); $t_R$=3.18, (UV, ELSD) 96%, 96%. $^1$H NMR (500 MHz, CDCl$_3$): 1.25 (m, 2H), 1.60 (m, 2H), 1.65 (m, 2H), 1.95 (m, 2H), 2.20 (s, 6H), 2.35 (m, 1H), 2.45 (d, 2H), 4.25 (d, 2H), 4.60 (s, 1H), 6.40 (s, 2H), 6.85 (broad, 1H), 7.10 (s, 2H).

5w 2-Cyclopentyl-N-{2,6-dichloro-4-[(4-fluorophenylamino)-methyl]-phenyl}-acetamide Yield: 52%. LC-MS (m/z) 395 (MH$^+$); $t_R$=3.31, (UV, ELSD) 96%, 99%. $^1$H NMR (500 MHz, CDCl$_3$): 1.25 (m, 2H), 1.63 (m, 4H), 1.95 (m, 2H), 2.35 (m, 1H), 2.45 (d, 2H), 4.05 (broad, 1H), 4.25 (broad, 2H), 6.50 (m, 2H), 6.87 (m, 2H), 7.40 (s, 2H).

5x 2-Cyclopentyl-N-{2,6-dichloro-4-[(5-trifluoromethylpyridin-2-ylamino)-methyl]-phenyl}-acetamide Yield: 47%. LC-MS (m/z) 446 (MH$^+$); $t_R$=3.10, (UV, ELSD) 95%, 98%. $^1$H NMR (500 MHz, CDCl$_3$): 1.30 (m, 2H), 1.65 (m, 4H), 1.90 (m, 2H), 2.35 (m, 1H), 2.45 (d, 2H), 4.50 (broad, 1H), 4.65 (broad, 2H), 6.50 (d, 1H), 6.90 (s, 1H), 7.40 (s, 2H), 7.60 (d, 1H), 8.40 (s, 1H).

EXAMPLE 6

6a N-(4-Bromo-2-methyl-6-morpholin-4-yl-phenyl)-3,3-dimethyl-butyramide

N-(2-Amino-4-bromo-6-methyl-phenyl)-3,3-dimethyl-butyramide (1v, 1.01 g), N,N-diisopropyl-ethylamine (1.80 mL) and bis(2-bromoethyl)ether (0.50 mL) were dissolved in dry N,N-dimethylformamide (5 mL) and heated to 180° C. for 50 minutes in a sealed microwave process vial. Saturated aqueous sodium bicarbonate (20 mL) was added and the mixture was extracted with ethyl acetate (3×20 mL), the combined organic phases were dried over sodium sulfate and concentrated in vacuo. The crude product was purified by flash chromatography to furnish 0.740 g (60% yield) of the title compound as a white solid. LC-MS (m/z) 370 (MH$^+$); $t_R$=3.05, (UV, ELSD) 95%, 99%. $^1$H NMR (500 MHz, DMSO-d$_6$): 1.05 (s, 9H), 2.09 (s, 3H), 2.23 (s, 2H), 2.80 (t, 4H), 3.69 (t, 4H), 7.03 (d, 1H), 7.15 (d, 1H), 8.99 (s, 1H).

TABLE 1

Reagents used for the preparation of compounds in Example 1-6

| Name | Supplier | CAS no. | Cat. no. |
| --- | --- | --- | --- |
| (2'-dicyclohexylphosphanyl-biphenyl-2-yl)-dimethyl-amine | STREM | 213697-53-1 | 15-1145 |
| (3-acetylaminophenyl)boronic acid | Lancaster | 78887-39-5 | 14023 |
| [(2-methylsulfonyl)aminophenyl]boronic acid pinacol ester | Combiblocks 2000 | | BB-2172-500 |
| 1,10-phenanthroline | Avocado | 66-71-7 | 13163 |
| 2,3-dihydro-1,4-benzodioxin-6-ylboronic acid | Maybridge | 164014-95-3 | CC01312 |
| 2,4,6-Trifluoronitrobenzene | Aldrich | 315-14-0 | 26,180-7 |
| 2,6-dimethylaniline | Fluka | 87-62-7 | 39520 |
| 2-[4-(trifluoromethyl)phenyl]pyrrolidine | Array | | 2AAX-Q07-0 |
| 2-Amino-5-chloropyridine | Aldrich | 1072-98-6 | A4,680-3 |
| 2-Amino-5-(trifluoromethyl)pyridine | Acros | 74784-70-6 | RF04702DA |
| 2-Bromo-4,6-dichloroaniline | Aldrich | 697-86-9 | 29,769-0 |
| 2-Amino-5-nitrobenzotrifluoride | Aldrich | 121-01-7 | 19,657-6 |
| 2-Bromo-4,6-dimethylaniline | Aldrich | 41825-73-4 | 52,886-2 |
| 2-methoxy-4-(4,4,5,5-tetramethyl-1,3,2-dioxaborolan-2-yl)phenol | Aldrich | | 51,878-6 |
| 2-methoxyphenylboronic acid | Aldrich | 5720-06-9 | 44,523-1 |
| 2-Methoxypyridine-5-carboxaldehyde | Aldrich | 65873-72-5 | 53,306-8 |
| 2-Methyl-4-nitroaniline | Aldrich | 99-52-5 | 14,643-9 |
| 3-(4,4,5,5-tetramethyl-1,3,2-dioxaborolan-2-yl)phenol | Aldrich | 214360-76-6 | 52,256-2 |
| 3-(trifluoromethoxy)benzeneboronic acid | Frontier Scientific | 179113-90-7 | T3636 |
| 3,4-difluoroaniline | Aldrich | 3863-11-4 | 27,023-7 |
| 3,5-bis(trifluoromethyl)benzeneboronic acid | Aldrich | 73852-19-4 | 47,107-0 |
| 3,5-difluoroaniline | Aldrich | 372-39-4 | 26,353-2 |
| 3-aminobenzeneboronic acid | ABCR | 30418-59-8 | AV18189 |
| 3-chloroaniline | Aldrich | 108-42-9 | C2,240-7 |
| 3-cyanophenylboronic acid | Aldrich | 150255-96-2 | 51,301-6 |
| 3-fluoro-4-trifluoromethylbenzaldehyde | ABCR | 204339-72-0 | AV20008 |
| 3-fluoroaniline | Fluorochem | 372-19-0 | 1438 |
| 3-methoxy-aniline | Fluka | 536-90-3 | 10480 |

TABLE 1-continued

Reagents used for the preparation of compounds in Example 1-6

| Name | Supplier | CAS no. | Cat. no. |
|---|---|---|---|
| 3-quinolineboronic acid | Frontier Scientific | 191162-39-7 | Q5061 |
| 3-trifluoromethylaniline | Fluka | 98-16-8 | 07060 |
| 4-(dimethylamino)phenylboronic acid | Aldrich | 28611-39-4 | 48,353-2 |
| 4-(trifluoromethyl)benzylamine | Aldrich | 3300-51-4 | 26,350-8 |
| 4-Amino-2,6-dichloropyridine | Aldrich | 2587-02-2 | 56,534-2 |
| 4-Bromo-2,6,-dichloroaniline | Avocado | 697-88-1 | A14884.14 |
| 4-Bromo-2,6-dimethylaniline | Aldrich | 24596-19-8 | 19,237-6 |
| 4-Bromo-2-methyl-6-nitro-phenylamine | Maybridge | 77811-44-0 | BTB 07466 |
| 4-chloroaniline | Aldrich | 106-47-8 | C2,241-5 |
| 4-Chlorophenylacetyl chloride | Lancaster | 25026-34-0 | 6317 |
| 4-fluoroaniline | Fluorochem | 371-40-4 | F03410 |
| 4-fluorobenzaldehyde | Aldrich | 459-57-4 | 12,837-6 |
| 4-Fluorophenylacetyl chloride | Aldrich | 459-04-1 | 46,695-6 |
| 4-fluorophenylboronic acid | Aldrich | 1765-93-1 | 41,755-6 |
| 4-isopropylphenylboronic acid | Lancaster | 16152-51-5 | 17459 |
| 4-methyl-2-phenyl-5-pyrimidinecarbaldehyde | Maybridge | 342405-36-1 | CC20204 |
| 4-methylaniline | Fluka | 106-49-0 | 89632 |
| 4-nitro-2-trifluoromethyl-phenylamine | Aldrich | 121-01-7 | 19,657-6 |
| 4-trifluoromethylaniline | Aldrich | 455-14-1 | 22,493-6 |
| 4-trifluoromethylbenzaldehyde | Aldrich | 455-19-6 | 22,494-4 |
| 4-vinylphenylboronic acid | Aldrich | 2156-04-9 | 41,758-0 |
| 5-chloro-2-thiophenecarboxaldehyde | Aldrich | 7283-96-7 | 44,323-9 |
| 6-(4-methylphenoxy)nicotinaldehyde | Bionet Research | | 5L-355S |
| 6-(trifluoromethyl)pyridine-3-carboxaldehyde | Fluorochem | | 9397 |
| azacycloheptane | Aldrich | 111-49-9 | H1,040-1 |
| Bicyclo[2.2.1]hept-2-yl-acetic acid | Aldrich | 1007-01-8 | 12,726-4 |
| Bis-(2-bromoethyl)ether | Aldrich | 5414-19-7 | 38,220-5 |
| Bis(dibenzylideneacetone)palladium | Acros | 32005-36-0 | 29197-0050 |
| Bromine | Aldrich | 7726-95-6 | 20,788-8 |
| cesium carbonate | Aldrich | 534-17-8 | 44,190-2 |
| Chloroformic acid 2-methoxyethyl ester | Aldrich | 628-12-6 | 59,229-3 |
| copper(II) trifluoromethanesulfonate | Aldrich | 34946-82-2 | 28,367-3 |
| Cyclohexanecarbonyl chloride | Aldrich | 2719-27-9 | 15,696-5 |
| 3-cyclohexylpropionyl chloride | Acros | 39098-75-4 | 35071-0250 |
| Cyclopentylacetyl chloride | Lancaster | 1122-99-2 | 14562 |
| Dibenzylideneacetone | Lancaster | 35225-79-7 | 2181 |
| ethyl chloroformate | Merck | 541-41-3 | 8.00881.2500 |
| Heptanoyl chloride | Aldrich | 2528-61-2 | 14,724-9 |
| Hexanoyl chloride | Aldrich | 142-61-0 | 29,465-9 |
| isopropylmagnesium chloride (2M in THF) | Aldrich | 1068-55-9 | 23,011-1 |
| Morpholine | Aldrich | 110-91-8 | 25,236-0 |
| N-[(Dimethylamino)-1H-1,2,3-triazolo[4,5-b]pyridin-1-ylmethylene]-N-methylmethanaminium hexafluorophosphate N-oxide | Fluka | 148893-10-1 | 11373 |
| n-Propyl chloroformate | Aldrich | 109-61-5 | 24,946-7 |
| Octanoyl chloride | Fluka | 111-64-8 | 21700 |
| p-Anisidine | Aldrich | 104-94-9 | A8,825-5 |
| palladium(II) acetate | Aldrich | 3375-31-3 | 20,586-9 |
| Pentanoyl chloride | Aldrich | 638-29-9 | 15,714-7 |
| phenylboronic acid | Aldrich | 98-80-6 | P2,000-9 |
| pyrrole | Aldrich | 109-97-7 | 13,170-9 |
| tert-butyl lithium (1.7M in heptane) | Aldrich | 594-19-4 | 18,619-8 |
| Tert-butylacetyl chloride | Aldrich | 7065-46-5 | B8,880-2 |
| Tert-butyloxycarbonyl-L-leucine | Aldrich | 13139-15-6 | 13,454-6 |
| Tert-butyloxycarbonyl-L-valine | Aldrich | 13734-41-3 | 35,972-6 |
| thiophene-2-acetyl chloride | Aldrich | 39098-97-0 | 19,599-5 |
| Trans-2-phenyl-1-cyclopropanecarbonyl chloride | Aldrich | 939-87-7 | 13,430-9 |

In vitro and in vivo Testing

The compounds of the invention have been tested and shown effect in one or more of the below models:

Relative Efflux Through the KCNQ2 Channel.

This exemplifies a KCNQ2 screening protocol for evaluating compounds of the present invention. The assay measures the relative efflux through the KCNQ2 channel, and was carried out according to a method described by Tang et al. (Tang, W. et. al., *J. Biomol. Screen.* 2001, 6, 325-331) for hERG potassium channels with the modifications described below.

An adequate number of CHO cells stably expressing voltage-gated KCNQ2 channels were plated at a density sufficient to yield a mono-confluent layer on the day of the experiment. Cells were seeded on the day before the experiment and loaded with 1 µCi/ml [$^{86}$Rb] over night. On the day of the experiment cells were washed with a HBSS-containing buffer. Cells were pre-incubated with drug for 30 minutes and the $^{86}$Rb$^+$ efflux was stimulated by a submaximal concentration of 15 mM KCl in the continued presence of drug for additional 30 minutes. After a suitable incubation period, the supernatant was removed and counted in a liquid scintillation counter (Tricarb). Cells were lysed with 2 mM NaOH and the amount of $^{86}Rb^+$ was counted. The relative efflux was calculated $((CPM_{super}/(CPM_{super}+CPM_{cell}))_{Cmpd}/(CPM_{super}/(CPM_{super}+CPM_{cell}))_{15\ mM\ KCl})*100-100$.

The compounds of the invention have an $EC_{50}$ of less than 20000 nM, in most cases less than 2000 nM and in many cases less than 200 nM. Accordingly, the compounds of the invention are considered to be useful in the treatment of diseases associated with the KCNQ family potassium channels.

Electrophysiological Patch-Clamp Recordings.

Voltage-activated KCNQ2 currents were recorded from mammalian CHO cells by use of conventional patch-clamp recordings techniques in the whole-cell patch-clamp configuration (Hamill O P et. al. *Pflügers Arch* 1981; 391: 85-100). CHO cells with stable expression of voltage-activated KCNQ2 channels were grown under normal cell culture conditions in $CO_2$ incubators and used for electrophysiological recordings 1-7 days after plating. KCNQ2 potassium channels were activated by voltage steps up to +80 mV in increments of 5-20 mV (or with a ramp protocol) from a membrane holding potential between −100 mV and −40 mV (Tatulian L et al. *J Neuroscience* 2001; 21 (15): 5535-5545). The electrophysiological effects induced by the compounds were evaluated on various parameters of the voltage-activated KCNQ2 current. Especially effects on the activation threshold for the current and on the maximum induced current were studied.

Some of the compounds of the invention have been tested in this test. A left-ward shift of the activation threshold or an increase in the maximum induced potassium current is expected to decrease the activity in neuronal networks and thus make the compounds useful in diseases with increased neuronal activity-like epilepsia.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. Pharmacology Biochemistry and Behavior 1993, 45, 321-325).

Electrical Seizure-Threshold Test

A modification of the up-and-down method (Kimball et al. Radiation Research 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure-Threshold Test

The threshold dose of pentylenetetrazole required to induce a clonic convulsion was measured by timed infusion of pentylenetetrazole (5 mg/mL at 0.5 mL/minute) into a lateral tail vein of groups of male mice (Nutt et al. *J Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold +25 µA daily for 3-5 weeks and on each occasion seizure severity, seizure duration, and duration of electrical after discharge were noted. (Racine. *Electroencephalography and Clinical Neurophysiology* 1972, 32, 281-294).

Side Effects

Central nervous system side-effects were measured by measuring the time mice would remain on rotarod apparatus (Capacio et al. *Drug and Chemical Toxicology* 1992, 15, 177-201); or by measuring their locomotor activity by counting the number of infra-red beams crossed in a test cage (Watson et al. *Neuropharmacology* 1997, 36, 1369-1375). Hypothermic actions on the animals core body temperature of the compound were measured by either rectal probe or implanted radiotelemetry transmitters capable of measuring temperature (Keeney et al. *Physiology and Behaviour* 2001, 74, 177-184).

Pharmacokinetics

The pharmacokinetic properties of the compounds were determined via. i.v. and p.o. dosing to Sprague Dawley rats, and, thereafter, drawing blood samples over 20 hours. Plasma concentrations were determined with LC/MS/MS.

The invention claimed is:
1. A compound having formula I:

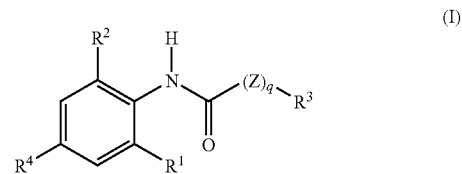

wherein:
Z is O or S;
q is 0;
$R^1$ and $R^2$ are each independently selected from the group consisting of halogen, cyano, amino, $C_{1-6}$-alk(en/yn)yl, $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy, and $C_{3-8}$-cycloalk(en)yl-$C_{1-6}$-alk(en/yn)yloxy;
$R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, amino-$C_{1-6}$-alk(en/yn)yl, amino-$C_{3-8}$-cycloalk(en)yl, amino-$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl; and
$R^4$ is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, Aryl, Aryl-$C_{3-8}$-cycloalk(en)yl, Aryl-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $NR^5R^6$ and $R^7NH$—$C_{1-6}$-alk(en/yn)yl;

wherein:
R⁵ and R⁶ are each independently selected from the group consisting of hydrogen, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{1-6}$-alk(en/yn)yl, $C_{3-8}$-cycloalk(en)yl, and $C_{3-8}$-cycloalk(en)yl-$C_{1-6}$alk(en/yn)yl, with the proviso that R⁵ and R⁶ can not both be hydrogen; and R⁷ is selected from the group consisting of $C_{1-6}$-alk(en/yn)yl; $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Aryl-$C_{1-6}$-alk(en/yn)yl, and Aryl-$C_{3-8}$-cycloalk(en)yl;

with the proviso that the compound of formula I is not N-(4-Bromo-2,6-dimethyl-phenyl)-2-cyclopentyl-acetamide;
or a pharmaceutically acceptable salt thereof.

2. The compound according to claim 1, wherein R¹ and R² are each independently selected from the group consisting of halogen, amino, $C_{1-6}$-alk(en/yn)yl, Aryl, and halo-$C_{1-6}$-alk(en/yn)yl.

3. The compound according to claim 1, wherein R³ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, and amino-$C_{1-6}$-alk(en/yn)yl.

4. The compound according to claim 1, wherein R⁴ is selected from the group consisting of halogen, $C_{1-6}$-alk(en/yn)yl, NR⁵R⁶ and R⁷NH—$C_{1-6}$-alk(en/yn)yl, wherein R⁵, R⁶ and R⁷ are as previously defined.

5. The compound according to claim 4, wherein R⁴ is NR⁵R⁶, wherein R⁵ and R⁶ are independently selected from the group consisting of hydrogen, Aryl-$C_{1-6}$-alk(en/yn)yl, and $C_{1-6}$-alk(en/yn)yl, with the proviso that R⁵ and R⁶ cannot both be hydrogen.

6. The compound according to claim 4, wherein R⁴ is R⁷NH—$C_{1-6}$-alk(en/yn)yl, wherein R⁷ is Aryl.

7. The compound according to claim 1, wherein any Aryl is optionally substituted with one or more substituents independently selected from the group consisting of amino, halogen, cyano, $C_{1-6}$-alk(en/yn)yl, halo-$C_{1-6}$-alk(en/yn)yl, hydroxy, $C_{1-6}$-alk(en/yn)yloxy, halo-$C_{1-6}$-alk(en/yn)yloxy, di-($C_{1-6}$-alk(en/yn)yl)amino, $C_{1-6}$-alk(en/yn)yl-CO—NH— and $C_{1-6}$-alk(en/yn)yl-sulfonamide; or two adjacent substituents may together with the Aryl group to which they are attached form a 4-8 membered ring, which is optionally substituted with one or more $C_{1-6}$-alk(en/yn)yl groups.

8. The compound according to claim 1, wherein the compound is selected from the group consisting of:
Hexanoic acid (4-bromo-2,6-dimethyl-phenyl)-amide,
N-(4-Bromo-2,6-dimethyl-phenyl)-2-(4-fluoro-phenyl)-acetamide,
N-(2-Bromo-4,6-dimethyl-phenyl)-2-(4-fluoro-phenyl)-acetamide,
N-(2-Bromo-4,6-dimethyl-phenyl)-3,3-dimethyl-butyramide,
N-(2-Bromo-4,6-dimethyl-phenyl)-2-cyclopentyl-acetamide,
N-(2-Bromo-4,6-dichloro-phenyl)-3,3-dimethyl-butyramide,
N-(2-Bromo-4,6-dichloro-phenyl)-2-(4-fluoro-phenyl)-acetamide,
N-(2-Bromo-4,6-dichloro-phenyl)-2-cyclopentyl-acetamide,
Heptanoic acid (4-bromo-2,6-dimethyl-phenyl)-amide,
Cyclohexanecarboxylic acid (4-bromo-2,6-dimethyl-phenyl)-amide,
2-Phenyl-cyclopropanecarboxylic acid (4-bromo-2,6-dimethyl-phenyl)-amide,
N-(4-Bromo-2,6-dimethyl-phenyl)-2-(4-chloro-phenyl)-acetamide,
Pentanoic acid (4-bromo-2,6-dimethyl-phenyl)-amide,
Octanoic acid (4-bromo-2,6-dimethyl-phenyl)-amide,
(S)-2-Amino-N-{2,6-dimethyl-4-[methyl-(4-trifluoromethyl-benzyl)-amino]-phenyl}-3-methyl-butyramide,
(S)-2-Amino-4-methyl-pentanoic acid {2,6-dimethyl-4-[methyl-(4-trifluoromethyl-benzyl)-amino]-phenyl}-amide,
N-(2-Amino-4-bromo-6-methyl-phenyl)-3,3-dimethyl-butyramide,
N-(3'-Amino-3,5-dimethyl-biphenyl-2-yl)-2-(4-fluoro-phenyl)-acetamide,
N-(4'-Dimethylamino-3,5-dimethyl-biphenyl-2-yl)-2-(4-fluoro-phenyl)-acetamide,
2-(4-Fluoro-phenyl)-N-(4'-hydroxy-3'-methoxy-3,5-dimethyl-biphenyl-2-yl)-acetamide,
2-(4-Fluoro-phenyl)-N-(3'-hydroxy-3,5-dimethyl-biphenyl-2-yl)-acetamide,
2-(4-Fluoro-phenyl)-N-(2'-methanesulfonylamino-3,5-dimethyl-biphenyl-2-yl)-acetamide,
N-(4'-Isopropyl-3,5-dimethyl-biphenyl-2-yl)-3,3-dimethyl-butyraniide,
2-Cyclopentyl-N-(3,5-dimethyl-biphenyl-2-yl)-acetamide,
N-(4'-Fluoro-3,5-dimethyl-biphenyl-2-yl)-2-(4-fluoro-phenyl)-acetamide,
N-(3,5-Dimethyl-3',5'-bis-trifluoromethyl-biphenyl-2-yl)-2-(4-fluoro-phenyl)-acetamide,
N-(3'-Acetylamino-3,5-dimethyl-biphenyl-2-yl)-2-(4-fluoro-phenyl)-acetamide,
2-(4-Fluoro-phenyl)-N-(2'-methoxy-3,5-dimethyl-biphenyl-2-yl)-acetamide,
N-(3,5-Dimethyl-4'-vinyl-biphenyl-2-yl)-2-(4-fluoro-phenyl)-acetamide,
N-(3'-Gyano-3,5-dimethyl-biphenyl-2-yl)-2-(4-fluoro-phenyl)-acetamide,
N-(3,5-Dimethyl-3'-trifluoromethoxy-biphenyl-2-yl)-2-(4-fluoro-phenyl)-acetamide,
N-[2,6-Dimethyl-4-(4-trifluoromethyl-benzylamino)-phenyl]-acetamide,
N-{2,6-Dimethyl-4-[methyl-(4-trifluoromethyl-benzyl)-aminol-]phenyl}-acetamide,
2-Cyclopentyl-N-[2,6-dimethyl-4-(4-trifluoromethyl-benzylamino)-phenyl]-acetamide,
2-Cyclopentyl-N-{2,6-dimethyl-4-[methyl-(4-trifluoromethyl-benzyl)-amino]-phenyl}-acetamide,
2-Cyclopentyl-N-{4-[(3-fluoro-phenylamino)-methyl]-2,6-dimethyl-phenyl }-acetamide,
N-{4-[(3-Chloro-phenylamino)-methyl]-2,6-dimethyl-phenyl}-2-cyclopentyl-acetamide,
2-Cyclopentyl-N-{4-[(3-methoxy-phenylamino)-methyl]-2,6-dimethyl-phenyl}-acetamide,
N-{4-[(4-Chloro-phenylamino)-methyl]-2,6-dimethyl-phenyl}-2-cyclopentyl-acetamide,
2-Cyclopentyl-N-{4-[(3,4-difluoro-phenylamino)-methyl]-2,6-dimethyl-phenyl}-acetamide,
2-Cyclopentyl-N-{2,6-dimethyl-4-[(4-trifluoromethyl-phenylamino)-methyl]-phenyl}-acetamide,
2-Cyclopentyl-N-[2,6-dimethyl-4-(p-tolylamino-methyl)-phenyl]-acetamide,
2-Cyclopentyl-N-{2,6-dimethyl-4-[(3-trifluoromethyl-phenylamino)-methyl]-phenyl}-acetamide,
2-Cyclopentyl-N-{4-[(3,5-difluoro-phenylamino)-methyl]-2,6-dimethyl-phenyl}-acetamide, (R)-2-Amino-4-methylpentanoic acid [2,6-dimethyl-4-(4-trifluoromethylbenzylamino)-phenyl]-amide,
Pentanoic acid {4-[(4-chlorophenylamino)-methyl]-2,6-dimethylphenyl}-amide,
2-(4-Chlorophenyl)-N-{4-[4(4-chlorophenylamino)-methyl]-2,6-dimethylphenyl}-acetamide,
N-[2-Chloro-6-trifluoromethyl-4-(4-trifluoromethylbenzylamino)-phenyl]-2-cyclopentylacetamide,
2-Cyclopentyl-N-{2,6-dichloro-4-[(4-fluoro-phenylamino)-methyl]phenyl}-acetamide; or
a pharmaceutically acceptable salt thereof.

9. A pharmaceutical composition comprising (i) a compound of formula I:

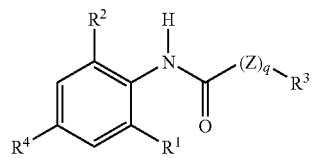

(I)

wherein:
Z is O or S;
q is 0;
$R^1$ and $R^2$ are each independently selected from the group consisting of halogen, cyano, amino, $C_{1-6}$-alk(en/yn)yl, $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy, and $C_{3-8}$-cycloalk(en)yl-$C_{1-6}$-alk(en/yn)yloxy;
$R^3$ is selected from the group consisting of $C_{1-8}$-alk(en/yn)yl, $C_{3-8}$-cycloalk(en)yl, $C_{3-8}$-cycloalk(en)yl-$C_{1-6}$-alk(en/yn)yl, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, amino-$C_{1-6}$-alk(en/yn)yl, amino-$C_{3-8}$-cycloalk(en)yl, amino-$C_{3-8}$-cycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{3-8}$-cycloalk(en)yl-$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl; and
$R^4$ is selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, Aryl, Aryl-$C_{3-8}$-cycloalk(en)yl, Aryl-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $NR^5R^6$ and $R^7NH$—$C_{1-6}$-alk(en/yn)yl; wherein:
$R^5$ and $R^6$ are each independently selected from the group consisting of hydrogen, Aryl-$C_{1-6}$-alk(en/yn)yl, Aryl-$C_{3-8}$-cycloalk(en)yl, Aryl-$C_{3-8}$-cycloalk(en)yl-$C_{1-6}$-alk(en/yn)yl, $C_{1-6}$-alk(en/yn)yl, $C_{3-8}$-cycloalk(en)yl, and $C_{3-8}$-cycloalk(en)yl-$C_{1-6}$-alk(en/yn)yl, with the proviso that $R^5$ and $R^6$ cannot both be hydrogen; and
$R^7$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Aryl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, Aryl-$C_{1-6}$-alk(en/yn)yl, and Aryl-$C_{3-8}$-cycloalk(en)yl;
with the proviso that the compound of formula I is not N-(4-Bromo-2,6-dimethyl-phenyl)-2-cyclopentyl-acetamide; or a pharmaceutically acceptable salt thereof; and
(ii) a pharmaceutically acceptable carrier or diluent.

* * * * *

UNITED STATES PATENT AND TRADEMARK OFFICE
CERTIFICATE OF CORRECTION

PATENT NO. : 7,601,870 B2  
APPLICATION NO. : 11/312664  
DATED : October 13, 2009  
INVENTOR(S) : Tornøe et al.

Page 1 of 1

It is certified that error appears in the above-identified patent and that said Letters Patent is hereby corrected as shown below:

On The Title Page

Item [*] Notice: Subject to any disclaimer, the term of this patent is extended or adjusted under 35 USC 154(b) by 340 days Delete the phrase "by 340 days" and insert -- by 637 days --

Signed and Sealed this

Fifteenth Day of June, 2010

David J. Kappos
*Director of the United States Patent and Trademark Office*